(12) United States Patent
Baarman

(10) Patent No.: US 11,173,222 B2
(45) Date of Patent: Nov. 16, 2021

(54) DISINFECTION BEHAVIOR TRACKING AND RANKING

(71) Applicant: UV Partners, Inc., Grand Haven, MI (US)

(72) Inventor: David W. Baarman, Fennville, MI (US)

(73) Assignee: UV Partners, Inc., Grand Haven, MI (US)

(*) Notice: Subject to any disclaimer, the term of this patent is extended or adjusted under 35 U.S.C. 154(b) by 0 days.

(21) Appl. No.: 17/044,136

(22) PCT Filed: Mar. 25, 2019

(86) PCT No.: PCT/US2019/023842
§ 371 (c)(1),
(2) Date: Sep. 30, 2020

(87) PCT Pub. No.: WO2019/190967
PCT Pub. Date: Oct. 3, 2019

(65) Prior Publication Data
US 2021/0052757 A1 Feb. 25, 2021

Related U.S. Application Data

(60) Provisional application No. 62/650,340, filed on Mar. 30, 2018.

(51) Int. Cl.
*A61L 2/10* (2006.01)
*G16H 40/20* (2018.01)
(Continued)

(52) U.S. Cl.
CPC ............ *A61L 2/10* (2013.01); *A61L 2/24* (2013.01); *A61L 2/28* (2013.01); *G16H 40/20* (2018.01);
(Continued)

(58) Field of Classification Search
None
See application file for complete search history.

(56) References Cited

U.S. PATENT DOCUMENTS 8,680,496 B2   3/2014  Leben
9,242,018 B2   1/2016  Cole et al.
(Continued)

FOREIGN PATENT DOCUMENTS

CN   102284139   12/2011
CN   104736261    6/2015
(Continued)

OTHER PUBLICATIONS

International Search Report and the Written Opinion of the International Searching Authority for International Application No. PCT/US2019/023842 dated Jul. 29, 2019.

*Primary Examiner* — Regina M Yoo
(74) *Attorney, Agent, or Firm* — Warner Norcross + Judd LLP

(57) ABSTRACT

A low dose disinfection and control system that utilizes empirical and theoretical data to compare performance, sensor data, stored patterns, historical usage, use intensity indexes over time and tracking information to provide a sophisticated data collection system for disinfection. The data can be used to dynamically control UV treatment parameters. This tracking is designed to enable a learning and feedback tool that helps to modify behavior and the understanding of infection. The present invention provides a system for integrating UV treatment into products. The product may include an outer layer of UV transmissive material forming an external touch surface. The UV disinfection system includes a UV source internal to the product. In use, the internal UV source produces UV-C light that passes into and permeates the outer layer to treat the touch (Continued)

surface. A UV reflective layer may be disposed beneath the outer layer.

10 Claims, 26 Drawing Sheets

(51) Int. Cl.
*A61L 2/24* (2006.01)
*A61L 2/28* (2006.01)

(52) U.S. Cl.
CPC ........ *A61L 2202/11* (2013.01); *A61L 2202/25* (2013.01)

(56) References Cited

U.S. PATENT DOCUMENTS

| | | | |
|---|---|---|---|
| 9,603,956 B2 | 3/2017 | Newham | |
| 9,615,884 B2 | 4/2017 | Armour et al. | |
| 9,974,873 B2 * | 5/2018 | Cole | A61L 2/10 |
| 2006/0188389 A1 | 8/2006 | Levy | |
| 2009/0117001 A1 | 5/2009 | Hyde et al. | |
| 2009/0191100 A1 | 7/2009 | Deal | |
| 2011/0256019 A1 | 10/2011 | Gruen et al. | |
| 2012/0282135 A1 | 11/2012 | Trapani | |
| 2012/0313014 A1 | 12/2012 | Stibich et al. | |
| 2013/0045132 A1 | 2/2013 | Tumanov | |
| 2013/0062534 A1 * | 3/2013 | Cole | A61N 5/0624 250/454.11 |
| 2013/0234041 A1 | 9/2013 | Deal | |
| 2014/0060094 A1 | 3/2014 | Shur et al. | |
| 2014/0183377 A1 | 7/2014 | Bettles et al. | |
| 2015/0090903 A1 * | 4/2015 | Cole | A61L 2/10 250/492.1 |
| 2016/0000953 A1 * | 1/2016 | Bettles | A61L 2/24 250/455.11 |
| 2016/0121007 A1 | 5/2016 | Dayton | |
| 2016/0151521 A1 | 6/2016 | Nathan et al. | |
| 2016/0296649 A1 | 10/2016 | Ramanand et al. | |
| 2017/0115826 A1 * | 4/2017 | Pryor | G06F 3/011 |
| 2017/0173195 A1 | 6/2017 | Stibich | |
| 2017/0296686 A1 | 10/2017 | Cole | |
| 2018/0117201 A1 * | 5/2018 | Bettles | A61L 2/24 |
| 2018/0154029 A1 | 6/2018 | Shr et al. | |
| 2018/0238846 A1 * | 8/2018 | Shim | G01N 33/0001 |

FOREIGN PATENT DOCUMENTS

| | | |
|---|---|---|
| CN | 106847663 | 6/2017 |
| JP | 2009-532092 | 9/2009 |
| JP | 2014-177742 | 9/2014 |
| JP | 2016-506274 | 3/2016 |
| JP | 2017-528258 | 9/2017 |
| JP | 2019-030635 | 2/2019 |
| KR | 10-0740903 | 7/2007 |
| WO | 2011/143265 | 11/2011 |
| WO | 2015/080768 | 6/2015 |
| WO | 2015/184428 | 12/2015 |
| WO | 2017/020028 | 2/2017 |
| WO | 2017/042662 | 3/2017 |
| WO | 2017/185138 | 11/2017 |
| WO | 2017/216533 | 12/2017 |
| WO | 2018/126034 | 7/2018 |

* cited by examiner

TABLE 1: ALL DATA (HIGHEST TO LOWEST ATP VALUES FOR EACH DEVICE IN ALPHABETICAL ORDER)

| DEVICE | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| BED BUTTONS | 3473 | 3278 | 523 | 443 | 275 | 193 | 161 | 157 | 143 | 122 | 84 | 79 | 71 | 61 | 56 | 51 | 50 | | | | |
| BED RAILS | 3244 | 995 | 550 | 362 | 288 | 209 | 203 | 195 | 165 | 164 | 164 | 155 | 141 | 85 | 82 | 33 | | | | | |
| IN-ROOM KEYBOARD | 4887 | 454 | 406 | 373 | 286 | 267 | 247 | 219 | 192 | 177 | 146 | 139 | 136 | 86 | 60 | 58 | 55 | 26 | | | |
| IN-ROOM MOUSE | 457 | 321 | 319 | 256 | 238 | 207 | 206 | 203 | 162 | 155 | 151 | 84 | 80 | 68 | 67 | 38 | 23 | | | | |
| IV PUMP | 6806 | 2654 | 2517 | 2493 | 2028 | 1546 | 1218 | 1064 | 810 | 673 | 623 | 614 | 542 | 479 | 356 | 342 | 236 | 191 | 191 | 171 | 141 |
| PATIENT ROLL-UP TABLE | 1792 | 663 | 329 | 212 | 189 | 182 | 159 | 134 | 108 | 75 | 54 | 37 | 36 | 35 | 18 | | | | | | |
| TOILET | 2713 | 268 | 257 | 254 | 131 | 124 | 101 | 80 | 47 | 39 | 37 | 36 | 32 | 30 | 29 | 12 | | | | | |
| VENTILATOR BUTTONS | 2349 | 1649 | 627 | 486 | 444 | 287 | 274 | 156 | 103 | 84 | | | | | | | | | | | |
| VENTILATOR SCREEN | 484 | 94 | 91 | 58 | 57 | 32 | 20 | 8 | 1 | | | | | | | | | | | | |
| VITALS CONTROL MODULE | 2746 | 761 | 720 | 681 | 599 | 579 | 505 | 459 | 442 | 273 | 213 | 193 | 164 | 162 | 160 | 105 | 61 | | | | |
| VITALS MONITOR | 567 | 401 | 283 | 177 | 143 | 127 | 115 | 45 | 43 | 42 | 41 | 34 | 29 | 24 | 10 | | | | | | |

Fig. 1A

DATA SUMMERY (RANKED FROM DIRTIEST TO CLEANEST DEVICE)

| | RANK | MEDIAN | SD | MAX | MIN |
|---|---|---|---|---|---|
| IV PUMP | 1 | 623 | 1523 | 6806 | 141 |
| VITALS CONTROL MODULE | 2 | 442 | 619 | 2746 | 61 |
| VENTILATOR BUTTONS | 3 | 366 | 752 | 2349 | 84 |
| IN-ROOM KEYBOARD | 4 | 185 | 1113 | 4887 | 26 |
| BED RAILS | 5 | 180 | 783 | 3244 | 33 |
| IN-ROOM MOUSE | 6 | 162 | 117 | 457 | 23 |
| BED BUTTONS | 7 | 143 | 1075 | 3473 | 50 |
| PATIENT ROLL-UP TABLE | 8 | 134 | 452 | 1792 | 18 |
| TOILET | 9 | 64 | 659 | 2713 | 12 |
| VENTILATOR SCREEN | 10 | 57 | 150 | 484 | 1 |
| VITALS MONITOR | 11 | 45 | 161 | 567 | 10 |

Fig. 1B

- DOCTORS
- NURSES
- RESIDENTS
- MAINTENANCE
- IT
- TECHNICIANS
- LAB
- VISITORS
- EQUIPMENT

DISINFECTION LANGUAGE
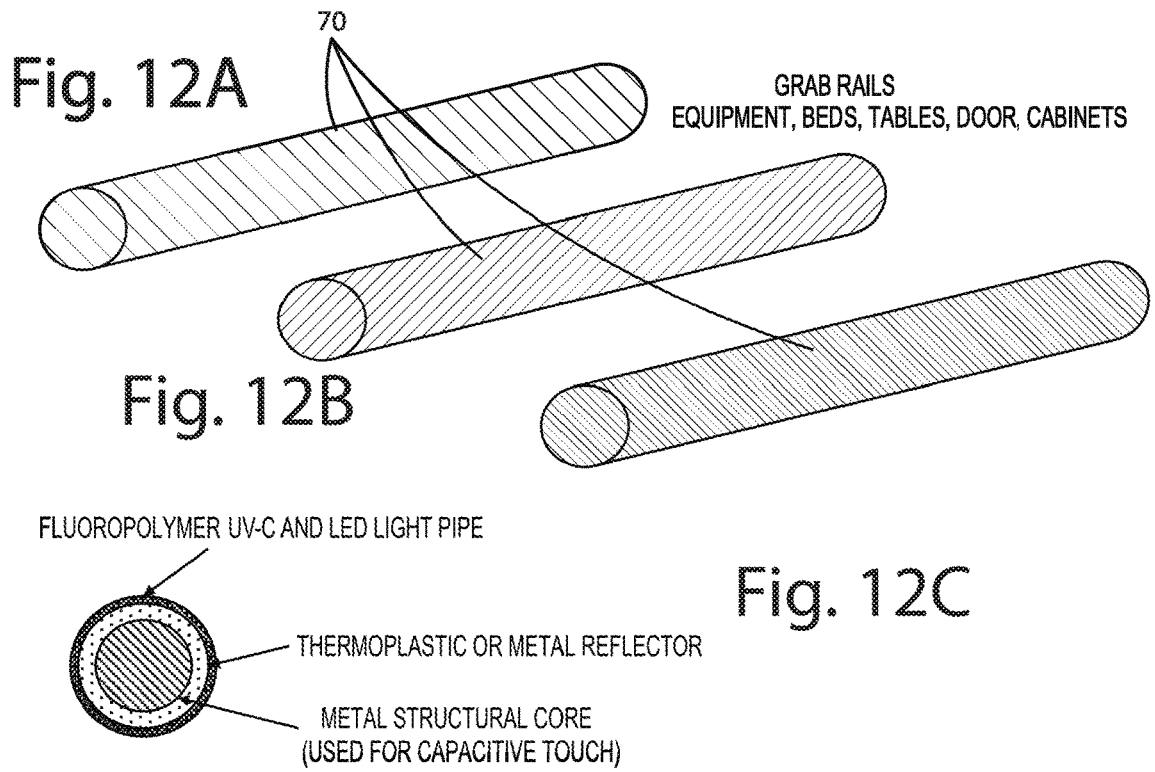
DISINFECTION LANGUAGE
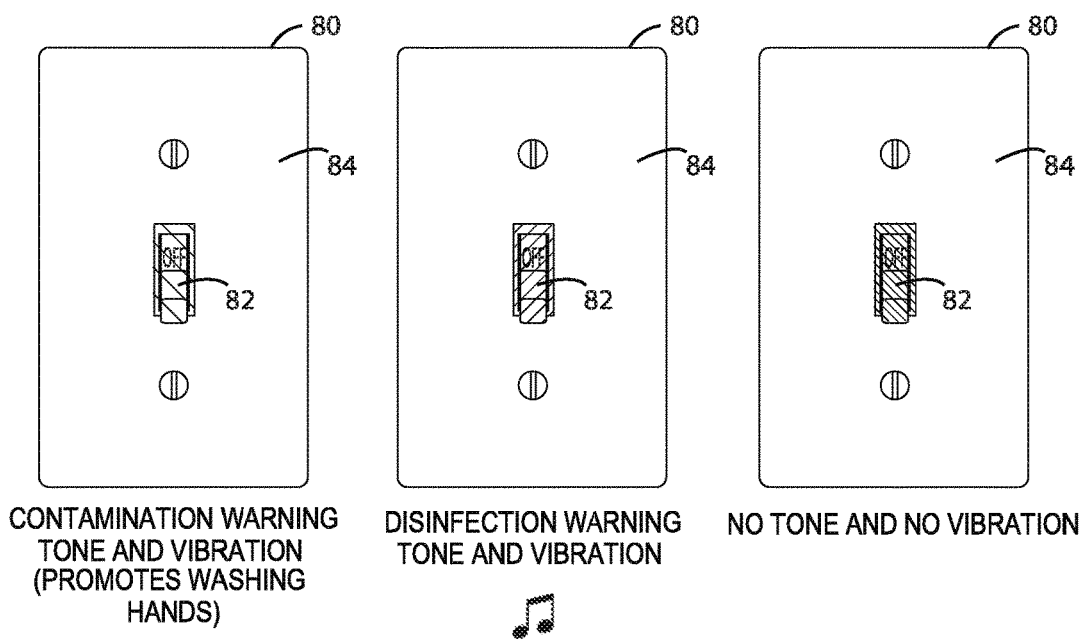

DISINFECTION LANGUAGE

DISINFECTION LANGUAGE

Workflow Analysis by Room by time

| UTC Time Stamp | ID | Device | Status | Consumable | Consumable Type | Associated Room | Paitient |
|---|---|---|---|---|---|---|---|
| 8:00 | 2776-10021-HWS-F-242 | Hand Wash | Operational | 80% | Purifier Liquid | 242 | 33781121 |
| 8:01 | 1675-10021-HLWS-F-243 | Light Switch | Off to On | 100% | Lamp Life | 242 | 33781121 |
| 8:03 | 3467-67555-UVD-E-445 | EMR Keyboard | Clean | 50% | Lamp Life | 242 | 33781121 |
| 8:10 | 02345-67885-IVD-E-221 | IV Pump | Clean | 90% | Lamp Life | 242 | 33781121 |
| 8:12 | 3467-67555-UVD-E-445 | EMR Keyboard | Partial | 50% | Lamp Life | 242 | 33781121 |
| 8:15 | 98776-056512-SCD-S-122 | Scanner | Clean | 78% | Lamp Life | 242 | 33781121 |
| 8:21 | 98776-056512-SCD-S-123 | Blood Pressure | Clean | 95% | Lamp Life | 242 | 33781121 |
| 8:26 | 98776-056512-SCD-S-124 | Temperature | Clean | 76% | Lamp Life | 242 | 33781121 |
| 8:30 | 3467-67555-UVD-E-445 | EMR Keyboard | Clean | 50% | Lamp Life | 242 | 33781121 |
| 8:33 | 90876-454-BED23-301 | Bed | Clean | 88% | Lamp Life | 242 | 33781121 |
| 8:35 | 02345-67885-IVD-E-221 | IV Pump | Partial | 90 | Lamp Life | 242 | 33781121 |
| 8:39 | 3467-67555-UVD-E-445 | EMR Keyboard | Clean | 50% | Lamp Life | 242 | 33781121 |
| 8:40 | 1675-10021-HLWS-F-243 | Light switch | On to Off | 100% | Lamp Life | 242 | 33781121 |
| 8:40 | 2776-10021-HWS-F-242 | Hand Wash | Operational | 80% | Purifier Liquid | 242 | 33781121 |

Fig. 19B

DISINFECTION BEHAVIOR TRACKING AND RANKING

BACKGROUND OF THE INVENTION

The present invention relates to disinfection, and more particularly to systems and methods associated with disinfection.

It is well known that hospital acquired infections continue to present a significant health risk. A variety of efforts have been made to reduce the risks presented by hospital acquired infections. For example, there is increasing interest in performing germicidal activities in a hospital environment. This includes the growing use of UV disinfection systems to perform repeated disinfection of a wide range of objects. There are currently a number of different types of UV disinfection products available on the commercial market. Many conventional UV disinfection products suffer from a variety of shortcomings. For example, UV energy has a tendency to degrade plastics and other materials. As a result, conventional UV disinfection treatment regimens may have the unintended consequence of causing excessive undesirable damage to objects in and around the treatment ranges.

There has been dramatic growth in the use of networks to collect data relating to a range of activities in and around hospitals and other medical environments. Although some of these systems are already gathering data relating to personnel, asset tracking, EMR's (Electronic Medical Records) and patient health, these workflows have not been combined to understand the path of infection.

Some known issues with present systems includes the limitation of not connecting the data from multiple workflows, understanding the high touch areas and the infection impact and understanding how to create a device that can be connected to all of these areas of impact and have an impact.

Another issue with the present treatment and monitoring is to create a secure network that is secure enough to use for electronic medical records.

SUMMARY OF THE INVENTION

In one aspect, the prevent invention provides a low-dose method of treating surfaces in which the UV intensity and exposure time of a UV treatment device are uniquely adjusted based on an initial calibration using a UV intensity meter. The lower minimal dose rate is compensated with the cycle times to provide that same effect as overdosing but with better results in surface breakdown. Providing the lower doses does not break down the plastics in the same way that higher dosages do. The low dose is generally safer for users' eyes and other forms of human contact. Low dose is defined in user environments. Terminal cleaning robots have a stipulation of not allowing operation if users present, as they will receive more than the allowed dosage as required by NIOSH CDC—National Institute of Occupational Safety and Health. In defining low dose we are measuring reflected and direct light for eye and skin exposure requirements. We are treating surfaces in ways that we protect users by first having the lowest allowable dose within the allowable exposure limits. We track both the proximity exposures to accumulate dose allowances over time. UV-C radiation has a short wavelength and contains more energy than UV-A- and UV-B radiation. It includes the greater part of the entire UV range and has a strong germicidal effect in the range of 254 nm. Like the visible wavelength of light, UV-C radiation radiates directly and loses its intensity in proportion to the distance from the source. UV-C radiation in lower dosages does not penetrate cloth or window glass. In the case of a higher radiation dosage, UV-C radiation causes red skin (erythms) and painful eye infection (conjunctivitis) to humans. This is why the threshold value of 6 mJ/cm$^2$, and/or 60 J/m$^2$ daily radiation dosage respectively, is recommended by the EU (EU Directive 2006-25-EC) (with 254 nm), which should not be exceeded. Sufficient lock outs and proximity detection interlocks can provide additional protections.

In one embodiment, the UV treatment device may include a disinfection control system that adjusts the UV treatment parameters to provide adequate disinfection despite interruptions in UV treatment cycles. For example, the UV treatment parameters of cycle time and/or UV light intensity may be varied as needed to provide the desired level of UV exposure. In one embodiment, the UV light cycle time and/or the UV light intensity is increased to compensate for interruptions. The system may track a plurality of factors relating to UV treatment and analyze those factors to make dynamic adjustments to the UV treatment parameters over time. The algorithm adjustment parameters are driven by several key aspects of the design and interaction. The first aspect is the interval of interaction and disinfection. Experience has revealed that, generally speaking, the more sick a patient is the more interactions are required. This may include an increased number of interactions with hospital personnel and medical equipment, as well as an increase in the length of interactions. Higher interaction frequency and/or durations required more disinfection cycles with shorter opportunities between touches. It is in these times where the probability for infection becomes statistically greater. One misstep in procedure can lead to infection spread. Typically a UV disinfection system would be designed to deliver maximum dose and intensity all the time. This approach is also limiting in multiple ways as the intensity is directly proportional to UV life, material degradation and OSHA human exposure rates. The algorithm described here utilizes the interval times to calculate average time between touches and may adjust to a higher power during cycles that are not of sufficient duration to allow a complete cycle at a normal intensity level. Any cycle time can be interrupted when the user reaches back into the treatment area. The system may also track the interruptions and the iteration timing of those interruptions, such as touches, to build a rolling average. The system may then adjust to that dose time and power for that time period. If the required dose time is less than the opportunity period, the power level is stepped up for that series of cycles. It should be noted that, in one embodiment, the system may have several classifications of cycles. A first cycle classification may be a touch or primary cycle. This is in direct response to a touch or contamination. A second cycle classification may be a secondary cycle that is assistive to help sterilize the area by hitting that surface with additional cycles. A third cycle classification may be one or more protocol cycles that are initiated based on interaction with terminal cleaning equipment or initiated by the understanding of cyclic infections, direct understanding of an outbreak or a deep cleaning cycle. In one embodiment, increasing UV light intensity, for example, by increasing power supplied to light source, are used sparingly as the OSHA safety limits and the UV life accumulators are affected accordingly. If the system gets above a preset level of interruptions and incomplete cycles this information may be sent to servers for analysis and reporting. This indicates an opportunity statistically for infection spread. Life and exposure per day are two separate accumulators in non-volatile memory. These accumulator registers may, in some embodiments, have back up registers as this information is important and there is a need to avoid corruption. The exposure accumulator tracks daily exposure and reports that information to the network server(s), for example, via the cloud. This information allows the hospital to report to OSHA the requirement for employee safety requirements. The UV source life accumulator accounts for the hours of on time, the UV source cycles and the extended power cycles at a 50% premium to UV source life. However, the premium higher intensities have a higher impact on UV source life so that number was chosen based on cycles and time tested.

In one embodiment, the UV treatment device is installed adjacent to the surface to be treated and then calibration is performed to ensure that the UV treatment parameter are accurate for that particular arrangement. The calibration measurements provide actual UV intensity measurements immediately adjacent the surface to be treated, and these measurements are used to adjust the UV intensity and/or exposure time, for example, in accordance with the algorithm provided above. The measured calibration number is stored in a non-volatile register and is set at installation by communicating to a custom calibration tool. Once set that system has the details for that surface, distance and measured dose and can reference that number for treating and reporting about that surface and employee exposure accordingly.

In one embodiment, the UV treatment device may include a control system that increases contact time and/or power supplied to the UV lamp to compensate for decrease in UV intensity output resulting from degradation of the UV lamp over time. For example, the control system may adjust the amount of power supplied to the UV lamp and/or the amount of time the UV lamp as a function of the frequency, length and distribution of touches or other interactions that interrupt the UV treatment cycle. For example, the system may determine the appropriate UV treatment parameters by selecting a cycle UV intensity value that is low enough to minimize UV exposure risks and reduce UV degradation, and a cycle duration that is sufficient to provide adequate UV treatment at the selected cycle intensity. During use, the system monitors a number of real life parameters, such as number of attempted treatment cycles, complete treatment cycles, interruptions to treatment cycles, duration of partial cycles, as well as the frequency, length and distribution of treatment cycles. The system analyzes the collected data and dynamically adjusts the UV treatment parameters to compensate for actual measured data. For example, the system may increase cycle duration, cycle intensity or make adjusts to the cycle frequency or cycle distribution. Calibration values from the most intense under the UV source and the outer reach of the treated surface are stored in non-volatile memory. The intensity change is allowed to change as long as it is allowable for the UV source and also meets the exposure criteria for OSHA eye and skin. In one example of where there is a need to adjust intensity when seeing short touch iterations, intensity is adjusted upwardly to enable proper dosage within the target iteration time. In one embodiment, the intensity was adjusted to 134% of the design intensity when the target touch iteration interval is optimally accounted for with dose. We managed the proper exposure limit within a safety margin (20%) to allow the maximum dose while protecting the user. Although this example includes a safety margin of 20%, the safety margin may vary from application to application, as desired. The surface is accounted for with the two intensity measurements allowing the system to understand the lowest dose area and maximum dose areas. The boost criteria can be variable or set for a preset value or percentage. The ratio is then dynamic based on the interval rates where 0 time between touches cannot be treated or disinfected. These times when the disinfection cycle is incomplete this information of incomplete cycles is accumulated and stored in non-volatile memory. The information it then uploaded to the cloud for reporting.

In one embodiment, the contact time and/or power (e.g. magnitude or duty cycle) supplied to the UV lamp may be increased progressively over time as desired to cause the UV treatment to remain substantially equivalent over the life of the UV lamp. In one embodiment, the contact time is increased until actual use data indicates that the frequency of use of the device does not, on average, provide sufficient time between uses to allow proper UV treatment. Once that point is reached, the control system may begin to increase the power supplied to the UV lamp so that the intensity of the UV lamp is increased to compensate for UV lamp degradation. The control system may be included with a maximum power output to the UV lamp to prevent UV lamp output from exceeding a threshold selected for user safety and/or UV lamp protection. The OSHA and ICNRP guidelines for electromagnetic radiation are listed below. The radiant exposure on unprotected eyes and skin within any 8 hour period for a wavelength of 200 to 315 nm is limited to values which depend on the wavelength of the radiation. For a broad band UV source the effective irradiance may be measured or calculated and the maximum permissible exposure determined from the table below. However, the system may be adapted to implement other exposure limitations.

| Effective Irradiance (Wm-2) | Maximum Permissible Exposure in an 8 hour period |
|---|---|
| 0.001 | 8 hours |
| 0.008 | 1 hour |
| 0.05 | 10 minutes |
| 0.5 | 1 minute |
| 3 | 10 seconds |
| 30 | 1 Second |
| 300 | 0.1 Second |

The main reason to limit UV source intensity and time is to assure that the safety limits are well below the standards for employee exposure while also increasing the UV source life and lessening the UV source maintenance periods. In one embodiment, a similar algorithm may be implemented to compensate for actual UV intensity measurements taken during calibration. For example, the control system may be configured to first increase contact time if calibration measurements indicate that UV intensity is lower than the standard. The increase is selected to compensate for the reduction in UV treatment caused by the lower UV intensity. If the control system determines that there is not likely to be sufficient time between uses to allow an increase in contact time to compensate for the decrease in UV intensity, the control system may additionally or alternatively increase the power supplied to the UV lamp, thereby increasing the intensity of the UV lamp.

The table below indicates a typical cycle time and interval for a system. The interruption rate indicates the typical percentage when the cycle cannot be shortened to meet dose. It also shows the exposure concerns and timing for the interruptions when the time of the exposure is accumulated.

| UVC exposure calculation | |
|---|---|
| Metric | 6-min cycle/90-s delay |
| Average daily cycles initiated | 83.51 cycles |
| Average cycle interruption rate, % | 54.64 |
| Average daily interruptions | 45.63 cycles |
| Average interruptions per 8-h period | 15.21 cycles |
| Maximum UVC exposure per interruption, s | 1 |
| Average UVC exposure per 8-h period, s | 15.21 |
| NIOSH UVC (60 µW/cm$^2$) limit per 8-h period, s | 100 |
| Percent of NIOSH limit | 15.21% of NIOSH limit |

NIOSH, National Institute for Occupational Safety and Health; UVC, ultraviolet-C.

In another aspect, an item to be treated is manufactured with a touchable surface having a UV reflective substrate layer and a UV transmissive over-layer. The over-layer has an exposed exterior surface that forms a touchable surface of the item. A UV light may be positioned adjacent to the UV transmissive over-layer so that UV light is transmitted into and travels along the over-layer progressively exiting over the exterior surface of the over-layer to treat the exterior surface. The reflective layer resists penetration of the UV light into substrate which not only protects the substrate from UV degradation, but also reflects that UV light back into the UV transmissive over-layer where it can contribute to UV treatment of the exterior surface. The UV transmissive over-layer facilitates transmission of the UV light along the over-layer with UV light exiting through the exterior surface. The UV transmissive over-layer may be configured to provide generally uniform escape of UV light and therefore provide generally uniform treatment of the exterior surface. For example, the thickness of the over-layer may diminish away from the UV light source and/or the over-layer may be textured to provide controlled escape of UV light.

In one embodiment, the item to be treated includes a thermoplastic substrate with reflective particles as a reflector material and a Teflon over-layer as a light-pipe to transmit UV-C 254 nm light over that touchable surface. The over-layer can be provided with UV light by the disinfection control system. The control system may operate the UV light based in part on contact with the exterior surface. For example, the disinfection system may use capacitive, PIR, contacts or other methods to detect touch on that surface, and use that touch information to determine when to apply a UV treatment and what parameters to use during treatments (e.g. UV exposure time and UV light intensity parameters).

In another aspect, the present invention provides a method for controlling the UV disinfection parameters of a UV disinfection system integrated into an item to be treated. In one embodiment, the method includes the step of measuring UV light intensity at a location on the surface of the item and adjusting the UV light intensity or exposure time to adjust for the specific transmissivity characteristics of the item. For example, when the item includes a substrate with lower reflectivity or an over-layer with lower transmissivity, the control system of the integrated UV treatment system may increase the power supplied to the UV lamp or increase the exposure times to compensate for the loss. It should be noted that the UV disinfection system may treat overall around 3-6 hours of around 6 minute low dose UV treatments per day. This accumulated dose provides a higher log reduction of disinfection and can be tuned by required cycles over a period to get the log reduction required by health agencies for specific pathogens.

In one embodiment, a disinfection control system with a combination of reflective and transmissive layers is integrated into a glove box, a vitals monitor, a bed rail, a table grab rail, door and cabinet pulls and an elevator buttons, as well as other items to be treated. In each of these implementations, exterior surface that will be touched by a person will include a UV transmissive over-layer disposed over a UV reflective substrate or under-layer.

In one embodiment, the present invention provides a method of construction for keyboards and touch displays that utilize the switches and the disinfection control system to enable low dose disinfection on a display or keyboard. In the context of a keyboard, the keyboard may include a printed circuit board that supports a plurality of push button switches, a plurality of UV reflective keys that are individually mounted to the push button switches and a UV transmissive overlay that covers the UV reflective keys. The keyboard also includes UV disinfection system that include control system and a UV light source. The UV light source is positioned adjacent to the UV transmissive overlay so that, when illuminated by the control system, UV light is transmitted into the overlay. If desired, the UV light source may be positioned behind a louver that directs the UV light into the overlay and shields it from the eyes of nearby individuals. The louver may be an integral part of the keyboard housing. In the context of a touch display kiosk, the kiosk may include a touch display contained within a kiosk enclosure. The touch display may be covered by a UV reflective film and a UV transmissive overlay. The kiosk also includes a UV disinfection system that includes a control system and a pair of UV light sources. The UV light sources are positioned adjacent to the UV transmissive overlay so that, when illuminated by the control system, UV light is transmitted into the overlay from opposed sides. If desired, the UV light source may be positioned behind a louver that directs the UV light into the overlay and shields it from the eyes of nearby individuals. The louver may be an integral part of the kiosk enclosure.

In one embodiment, the present invention provides a design and method to produce a mouse and/or keyboard using low dose UV-C that enable long life plastics with high chemical resistance. The PFA with a UV-C lamp that travels along the treated surfaces combined with the low dose method enables a solution that would typically self destruct over exposure. This system not only teaches how to disinfect a mouse but enables a system to enables the long life expected in the consumer electronics market.

In another aspect, the present invention provides a disinfection network with secure communications. This network can track assets and other items relating to disinfection probabilities and statistics for process feedback and control as well as driving training feedback. This network utilizes several layers of data to track hand washing compliance and disinfection compliance and control. In one embodiment, the system includes at least one server, a plurality of hubs capable of communicating with the server and a plurality of assets capable of communicating with the hubs. In one embodiment, a variety of assets to be tracked are provided with electronic communication capabilities. This may include equipment (e.g. mobile equipment and immobile equipment) and individuals (e.g. doctors, nurses, hospital staff and visitors). In one embodiment, each room (or separate region for which separate tracking is desired) includes a hub that is capable of communicating with both the assets and the server. The hub may collect and process data and/or it may function as a relay for routing communications between the server and the assets. In use, the hubs may communicate with each assets that is present (permanently or temporarily) to understand its UV treatment-related information, such as UV treatment activity and UV lamp life, and to track movement of that asset within the facilities. For example, the hub may collect information that allows the network to understand and control UV treatment activities of those assets that have integrated UV treatment capabilities. The hubs may also log when an asset enters a location and when it leaves. Asset location information may be transmitted to the server. The hubs may also be capable of communicating information to the assets, for example, to change the UV treatment parameters of a device (e.g. extend UV contact time or increase UV intensity when a particular infection has occurred) or reduce treatment when a location is not in use (e.g. a patient room that is unoccupied).

In another aspect, the present invention provides a contact interface or user interface that can be integrated into assets to assist in informing a user when contact with an asset occurs. The contact interface is configured to provide feedback when a user makes undesired contact with an enabled device. In one embodiment, the contact interface is incorporated into an asset that includes an associated UV treatment system that is configured to treat only a region of the asset intended for user contact. The contact interface is configured to sense when a user contacts the asset outside the user contact region. In response, the contact interface creates an alarm, such as tactile feed (e.g. haptic feedback), audible feedback, and/or visual feedback. In this way, the contact interface enables behavior change and immediate feedback. Additionally, the contact interface can initiate a supplemental treatment process intended to provide UV or other treatment of the asset in view of the contact outside the user contact region where the integrated UV treatment system is not capable of treating. In one embodiment, the contact interface of the asset communicates the undesired contact to the server, for example, through the hub managing communications in the corresponding region. This includes accumulators for the exposure incidents per 24 hours within our touch proximity and the short duration of exposure when reaching in for a touch to build an accumulated dosage per 24 hours per day of less than 60 mJ/cm2 for users. It is assumed that the reaction between the sensor and the touch happens within 1.2 seconds. This is a conservative average based on measurements and each touch is an accumulated dose. In one embodiment, the system may collect and maintain data indicative of accumulated overall dose for every touch within 24 hours. By connecting this data with user ID's using the network interface, the system can report on each individual dosage accumulations. The system tracks this accumulated exposure data for safety and available dose adjustment reasons and the ratio of compliance for safety and reporting. The available exposure data may be used for calculating an upward intensity adjustment window within safe limits with a safety ratio of 20%. Safety numbers on exposure by unit may be part of the scoring and proof of safety compliance with each unit deployed to easily meet the 6 mJ/cm2 eye contact thresholds and the 60 mJ/cm2 for skin exposure within a 24 hour period. Each touch event that occurs when a UV disinfection system is operating results in UV exposure time of about 0.15 seconds per touch (e.g. the approximate amount of time required for the touch/proximity sensor to sense the event and turn off the UV source). With a known exposure in uW/cm2, the system can accumulate this dosage over a period of time. Some requirements are 8 hours and others are 24 hours. We can validate that the exposure was well below the exposure limits of 60 mJ/cm2 for that device over that period of time and also calculate all the devices used for an entire hospital or building for that period. The 6 mJ/cm2 is a limit set for eye contact. The proximity area is configured to accommodate exposure levels that are barely measurable to assure very safe use and exposure to international standards.

In another aspect, the present invention provides a method for ranking and tracking disinfection based on exposure and probabilities on contact. In this embodiment, the disinfection network collects touches and other room details to provide dynamic and intelligent control over individual assets in the disinfection network. The network may collect infection data and compare with asset data collected by the network. In one embodiment, the disinfection network may track the location of infections within a location or region, compare this information with asset movement data (e.g. individuals, medical equipment and other mobile objects) to determine potential opportunities for infection to spread to additional regions, and make desired adjustments to the UV treatment parameters of UV treatment devices that might be within the region of the infection or any region in which it had the potential to spread by virtue of asset movement. For example, if the network determines that an asset, such as an IV pole or vitals monitor, was exposed to an infection in a room, the network may direct the UV disinfection system in that asset to perform an appropriate disinfection cycle. Further, if the network determines through location data that an asset, such as an IV pole or vitals monitor, that was exposed to an infection in one room is moved to a new room (or other new location), the network may cause the devices in that new room (or new location) to perform an appropriate disinfection cycle. If the new location is a patient room, the network may also maintain data concerning movement of the IV pole into that patient's room.

In one embodiment, the disinfection network may utilize hospital workflow data to enable additional information on personnel and patient status to inform and enable learning in order to control infections and provide optimal disinfection. For example, the workflow data may provide additional information of movement of individuals, such as doctors, nurses and other hospital staff, to understand and assess the potential for infection to spread through movement of individuals within the environment.

In one embodiment, the present invention may include a social media system for recognizing patterns and behaviors that can push information and messages based on conditions, events and patterns recognized in social media content. This content management system can continuously evolve to enable better and better practices that will help to change disinfection behavior and training. In one embodiment, the disinfection system may search for and identify health related messages on social media, including pre-existing social media platforms, such as Facebook. In one embodiment, the disinfection system may have a message transmission section that is capable of sending health and safety related messages using a social media platform. Using web crawlers for regional news articles, Twitter firehose and Facebook API interfaces the social media system can watch and search for terms relating to health, disease types (flue, cold season, out breaks etc.) and accumulate incident rates. The occurrence frequency of these terms are compared to a running distribution of occurrence's over time of year and weather conditions to build a predictive base. When these events increase as it relates to the system's base data or elevate, the system can push additional health protocols and notifications forcing additional cleanings based on the severity and type of the recorded event. Artificial intelligence learning algorithms assist in the statistical probabilities of location, weather, like temperature, humidity and temperature degree days as a probability element of the statistical references. These can be suggested events or automated with specific preset protocols or timing based from historical hospital infection data. Combined this data informs the relevance of when these probabilities may increase or decrease. The timing may be based on time of year where some of these are expected based on historical data. Severity of the response may be proportional to the severity of the outbreak and increase the time and frequency of cleaning accordingly.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components. Any reference to claim elements as "at least one of X, Y and Z" is meant to include any one of X, Y or Z individually, and any combination of X, Y and Z, for example, X, Y, Z; X, Y; X, Z; and Y, Z.

BRIEF DESCRIPTION OF THE DRAWINGS

FIG. 1A is a table showing ATP testing results.

FIG. 1B illustrates a list of the top 11 areas tested in hospital intensive care rooms relating to high touch bioloading areas of interest.

FIG. 12A-C shows a how the disinfection language might be used in a grab rail. The diagram shows the color feedback and interaction.

FIG. 13A-C shows an example of a light switch solution with lighted colors tactile and sound feedback.

FIG. 19B is a table of workflow analysis by room type.

DESCRIPTION OF THE CURRENT EMBODIMENT

A. Overview

Figure 2:
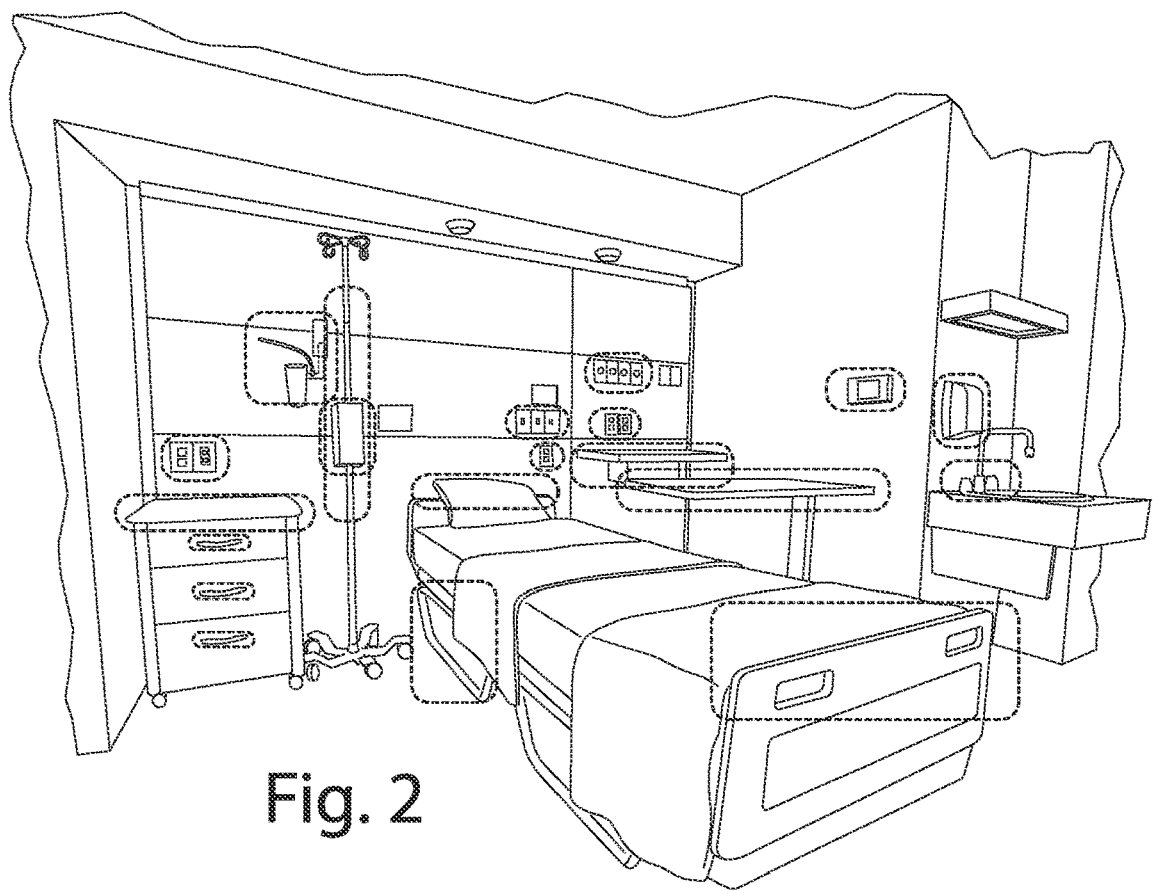
FIG. 2 illustrates areas that are touched frequently by staff and the patient and that are opportunities for disinfection.

The present invention relates to improvements associated with tracking and reducing the spread of infections, including without limitation systems and methods for collecting data and other information that might be relevant to understanding and addressing infections, systems and methods for implementing a disinfection language with instructive user interface devices, systems and methods for providing improved calibration and control of UV disinfection systems, as well as a range of integrated, internal UV disinfection systems.

The first inventive aspect of this disclosure is the low dose method of treating surfaces. The lower minimal dose rate is compensated with extended cycle times to provide that same effect as overdosing but with better results in surface breakdown. Providing the lower doses does not break down the plastics in the same way that higher dosages do. The low dose is safer for users' eyes and contact.

The second inventive aspect of this disclosure is directed to integrated UV disinfection systems and may involve using a UV transmissive outer layer that allows an internally disposed UV source to disinfect the outer layer. The device may include a thermoplastic substrate disposed below the outer layer with reflective particles as a reflector material. For example, a device may include a fluoropolymer, such as perfluoroalkoxy ("PFA"), over layer as a light-pipe to transmit UV-C 254 nm light over that touchable surface. A DuPont Teflon can be used but some good results have been with Daikin NEOFLON PFA AP201SH is a copolymer of tetrafluoroethylene and perfluoroalkylvinylether. It is a perfluoropolymer consisting of only carbon atoms and fluorine atoms without any hydrogen atom.

It has the same excellent performance as PTFE in a wide range from extremely low to high temperatures. In addition, it has excellent transparency, mechanical strength at high temperature. It can be molded in the same molding method as general thermoplastic resins. PTFE is used as a reflector material in conjunction with the UV-C light distribution material like TEFLON and PFA. The light-pipe layer may be illuminated driven by the disinfection control system and can use capacitive, PIR, contacts or other methods to detect touch on that surface. In some applications, a device may include one or more lenses that allow UV light to be transmitted on a plurality of surfaces to be treated. This may include internal or external illumination of surfaces. For example, a device may include a quartz lens used for projecting light externally on a first surface and internally on a second surface. A quartz lens may provide some advantages when it is desirable to protect the lamp from touching or it is desirable to clean the assembly. An example would be treating the handles of a cart internally for touch treatment while using a quartz lens to treat a surface like a keyboard below with one light source. The third inventive aspect of this disclosure involves a disinfection network with secure communications. This network can track assets of items relating to disinfection probabilities and statistics for process feedback and control as well as driving training feedback. This network may utilize several layers of data to track interactions, hand washing compliance and disinfection compliance and control.

The fourth inventive aspect of this disclosure relates to a disinfection language and feedback system that provide a form of user interface that enables behavior change and immediate feedback. This system utilizes tactile feedback, audible feedback, visual feedback with colors and a social feedback system and training application.

The fifth inventive aspect of this disclosure is the various applications for the disinfection control system including a glove box, vitals monitor bed rails, table grab rails, door and cabinet pulls, elevator buttons and more.

The sixth inventive aspect of this disclosure is a method of construction for keyboards and touch displays that may utilize the switches and the UV-C 254 disinfection control system to enable low dose disinfection on a display or keyboard.

The seventh inventive aspect of this disclosure is method for ranking and tracking disinfection based on exposure and probabilities on contact.

The eighth inventive aspect of this disclosure is utilizing hospital workflow to enable additional information on personnel and patient status to inform and enable learning in order to control infections and provide optimal disinfection The ninth inventive aspect of this disclosure is a social feedback system for recognizing patterns and behaviors that can push information and messages based on conditions, events and patterns. This content management system can continuously evolve to enable better and better practices that will help to change disinfection behavior and training.

The tenth inventive aspect of this disclosure is the design and method to produce a mouse and keyboard using low dose UV-C that enable long life plastics with high chemical resistance. The PFA with a UV-C lamp that travels along the treated surfaces combined with the low dose method enables a solution that would typically self-destruct as a result of over-exposure to UV energy. This system not only teaches how to disinfect a mouse but enables a system to enables the long life expected in the consumer electronics market.

The present invention is described in the context of various exemplary networks, devices, materials and constructions. It should be understood that the various aspects of the present invention are not limited to illustrative examples provided in this disclosure. Instead, the various aspects of the invention can be implemented in a wide variety of alternative embodiments as described in more detail below. Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

U.S. Pat. No. 9,242,018 B2 to Cole et al., which is entitled "Portable Light Fastening Assembly" and issued on Jan. 26, 2016; US Publication No. 2017/0296686 A1 to Cole, which is entitled "UV GERMICIDAL DEVICES, SYSTEMS, AND METHODS" and published Oct. 19, 2017; US Publication No. 2015/0090903 A1 to Cole, which is entitled "UV GERMICIDAL SYSTEM, METHOD, AND DEVICE THEREOF" and published Apr. 2, 2015, are incorporated herein by reference in their entireties.

B. Ranking of Touch Surfaces

Given the fragile nature of patients in the intensive care units, the cleaning of this hospital environment benefits from strict adherence to rigorous decontamination protocols. Despite this, the ICU remains a frequent site for the acquisition of hospital-acquired infections. An analysis was conducted to identify and objectively rank those surfaces in the ICU with the highest level of bioburden as determined by ATP testing. Special attention was paid to the identification of surfaces that could be fitted with a UV disinfection light for sterilization.

In order to rank various surfaces within the ICU, an ATP meter was used to collect numerical measurements. The instrument derives its output through the aqueous reaction of ATP, obtained from swabbing the environment, with the enzyme luciferase, from the firefly (Photinus pyralis). The emitted light is converted by a spectrophotometer to a voltage output and finally to a relative light unit (RLU) number on a digital display. Because of its relative nature, the ATP meter is better suited for the rank order comparisons of various surfaces than it is for the absolute determination of cleanliness. However, ATP meters are routinely used in and outside of the hospital for the purpose of the later. In total, eleven different surfaces were swabbed in twenty-two different patient rooms (FIG. 1A). A total of 171 samples were obtained as not all surfaces were available in all rooms. Because all eleven surfaces were of different sizes and ATP load is proportional to the amount of surface swabbed, precut stencils were used to standardize the swabbing area and allow for the accurate comparison of various surfaces. Four stencil shapes were cut, all of which allowed a swabbing surface of 4 square inches. The stencils were cleaned with bleach wipes in between each swabbing to reduce cross contamination of the surface by the stencil.

After obtaining all samples, the data was imported and analyzed in Minitab and exported to Excel for display purposes. Significant variations were seen between various devices in the same room and between the same devices in different rooms. The resulting non-normal data points were compared via the ranking of their median values, in accordance with statistical guidelines, to remove the effects of outliers on the averages. The data points are recorded in ranked order for each device in FIG. 1.

The ATP testing results are summarized in FIG. 1A. As can be seen, bioburden loads were a full order of magnitude higher on the dirtiest device (intravenous pumps, median RLU 623) as compared to the cleanest (touch screen vitals monitors, RLU 45).

FIG. 1B is a list of high touch surfaces ranked from dirtiest to cleanest based on the ATP bioloading tests. The high level of bioloading suggests that these surfaces present a greater risk of contamination, if not properly disinfected. It should be understood that this list represents the results of the test described above. While these test results may be helpful is prioritizing UV disinfection efforts, the result should not be interpreted to exclude any touch surfaces or classes of touch surfaces from the scope of the invention.

FIG. 2 shows a variety of touch surfaces in one exemplary high touch ecosystem. For example, wall switches WS, wall ports WP, table tops TT, drawer pulls DP, wall mounted medical instruments WMI, IV poles IP, pole mounted medical instruments PMI, bed rails BR, bed headboards BH, bed footboards BF, overbed tables OT, bedside electronics BE, wall mounted user interfaces WUI, hand soap dispensers HSD and sinks S are objects that are likely to see repeated touches and may be candidates for tracking and disinfection. Although there are many opportunities to provide disinfection in this environment, it may be desirable to focus disinfection and tracking efforts on the key opportunities for convenience touches. A convenience touch would be, for example, touching an IV pump or vitals monitor to reset an alarm. In these applications, there is an opportunity in the field to push these resets without gloving up or washing hands. These also present opportunities for learning and training if tracked and presented properly. It also leads to potential behavior modification if we teach and notify users of these activities as they happen.

C. UV Disinfection Network

Figure 3:
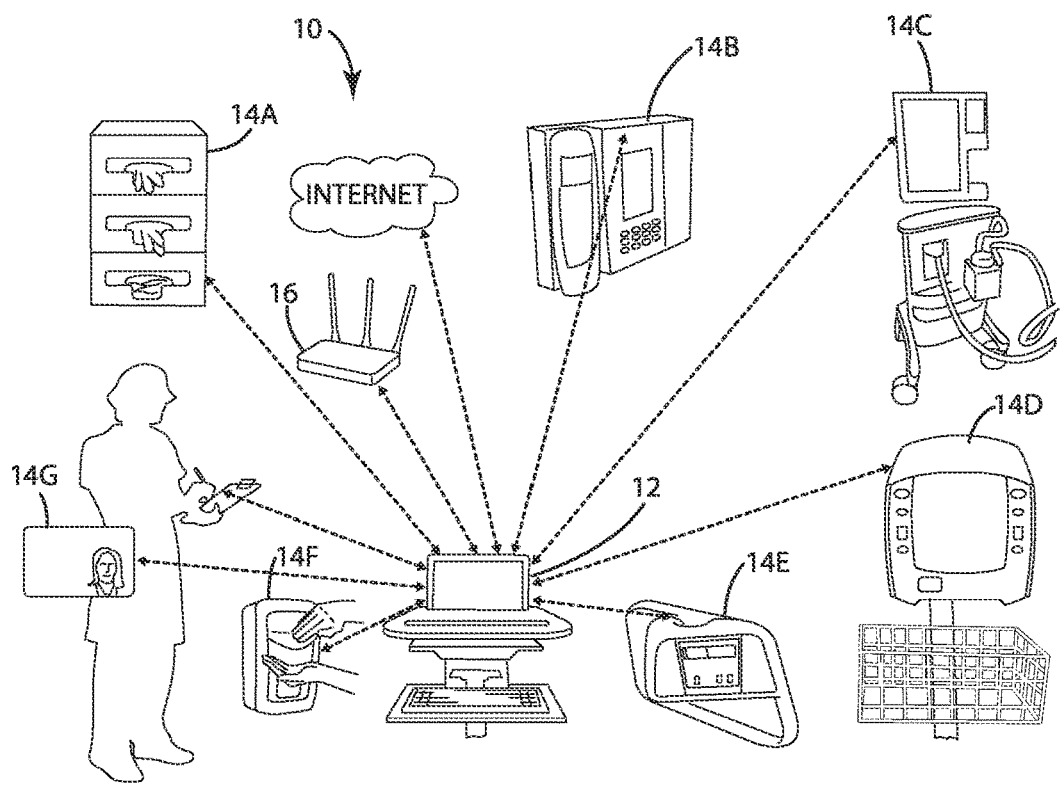
FIG. 3 illustrates one embodiment of a secure disinfection network that communicates to the glove box, the soap dispenser, the disinfectant dispenser, various equipment and then the hub accumulates the data and connected to the cloud.

In one aspect, the present invention provides a system and method for collecting data and other information that may be relevant to tracking infection and controlling disinfection opportunities. This may include tracking interactions with high touch surfaces, as well as other workflow (e.g. physical interactions within the monitored environment) or events that might be relevant to understanding and/or addressing the spread of infection. For example, FIG. 3 illustrates an exemplary system for tracking high touch areas and looking for specific workflow. An unwanted outcome of safe surfaces is that it may cause some individuals to assume that hand washing is not as important. We do not want to modify this behavior so we connect that information into our network when possible to enable and indicate proper workflow. That is also reinforced when a surface is touched by indication discussed later in this disclosure. By connecting these systems we can encourage proper hygiene and enable better disinfection in an effort to reduce HAI's. By tracking a chain of usages over time that workflow becomes very clear and this can be ranked and scores also described later in this disclosure. FIG. 3 also shows the network of devices 10 that are joined to produce this level of information. In this embodiment, the network 10 generally includes a disinfection hub 12, a plurality of enable devices 14a-g and a router 16 configured to access the Internet (or other local or wide area network) to allow communication between the network components in the room and the network components outside the room. As shown, the enabled devices may include a glove box 14a, an IV pump (and control) 14b, a ventilator 14c, a vitals monitor 14d, a bed components (such as rails and remote) 14e, a soap dispenser 14f and an ID tag 14g for an individual. Each of these devices 14a-g may have the ability to collect device-appropriate data and communicate that data to the disinfection hub 12. The disinfection hub 12 which relays the collected information via the router 16 to one or more remote components of the system, such as a remote server or collection of servers. In some applications, the disinfection hub 12 may have the ability to return communications to the enabled device. For example, the hand soap dispenser 14f can be touched relatively frequently so that the bioburden associated with the soap dispenser could be high. The soap dispenser 14f may include one or more desired sensors, such as a sensor capable of senses touches to the soap dispenser and/or a sensor capable of senses uses of the soap dispenser. The sensors may be coupled to a control circuit that collect sensor data and communicates that data to the disinfection hub 12 using wireless communication. To illustrated, the soap dispenser may have a WiFi or Bluetooth transceiver capable of exchanging communications with the disinfection hub 12. Other devices not have a sensor, but may simply communicate presence data. For example, an ID tag 14g may not be provided with any sensors, but may be used to determine presence of the individual in a location, such as a room. ID tags 14g may be provided to and carried by doctors, staff, patients and guests to allow movement of individuals within the hospital or other environment to be tracked. Movement data can, for example, be used to determine exposure to and potential spread of infections. The ID tag 14g may be an externally-powered device in that it may not have an onboard power supply, but may instead be activated by an external power supply. For example, the ID tag 14g may include an RFID tag that is activated and powered by an external electromagnetic field. It has been determined that device or sequence of use can be analyzed to tell much about the disinfection process. For example, the data obtained through the device can be considered alone and in combination to understand sequences or other workflows. For example, ID tag 14g information can be used to determine when an individual entered/exited a room and the soap dispenser data can be used to determine if that person washed their hands upon entry and/or exit. Similarly, the glove box 14a may include sensors to indicate when gloves are taken from the box. The glove box data could be combined with individual location data to determine if an individual put on gloves when entering a room. In the illustrated embodiment, each of the disinfection control devices or monitoring devices may be connected via a network interface. This information is used over the workflow to research and understand infection outcomes and becomes a tool for learning, training and behavior modification.

Figure 4:
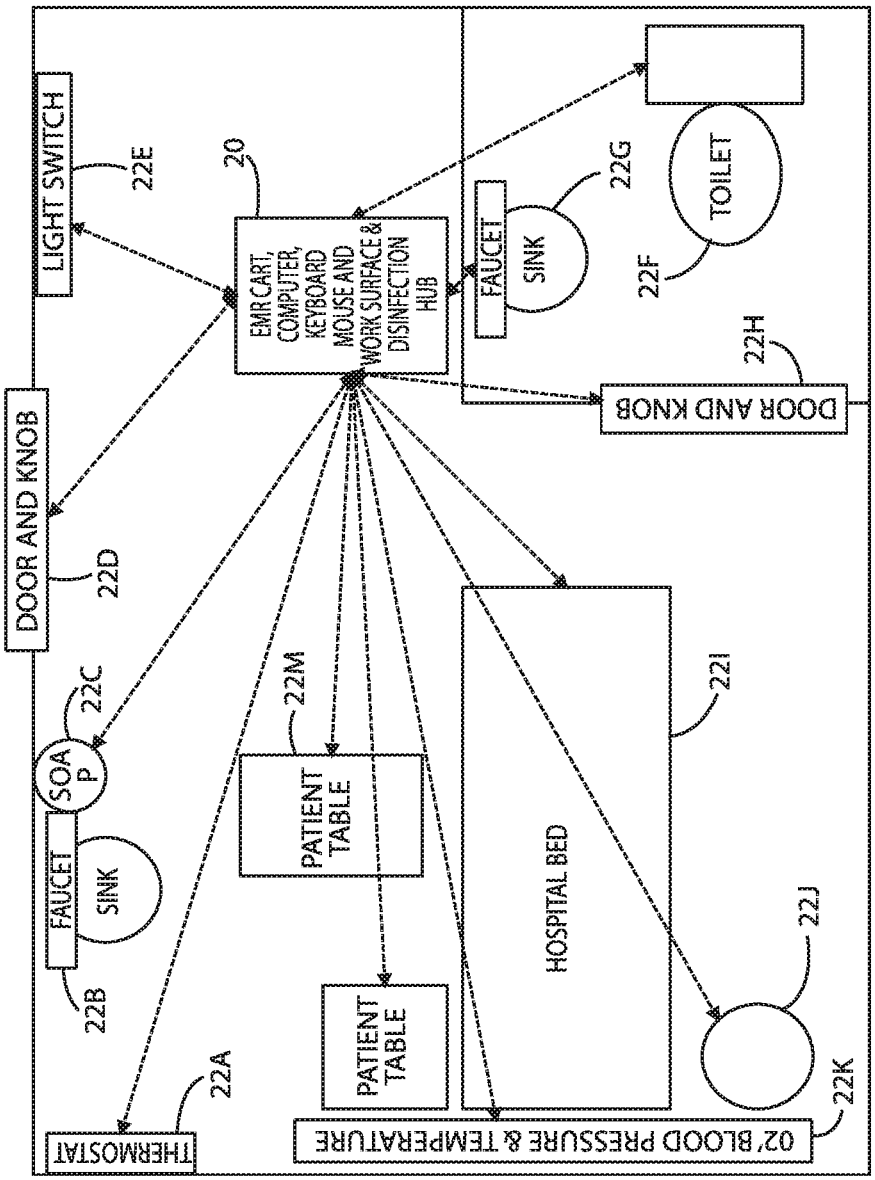
FIG. 4 illustrates an embodiment of the network within a room and what devices could communicate to the hub.

FIG. 4 gives a similar perspective in an alternative room (e.g. a patient room in a hospital or medical center) in which a central computer located in the room is selected for the disinfection hub. In this embodiment, the room may be divided into a treatment room TR and a bathroom BR. The network of enable devices may include a computer 20 that functions as a disinfection hub, a thermostat 22a, a faucet 22b, a soap dispenser 22c, a door knob 22d, a light switch 22e, a toilet 22f, a sink 22g, a bathroom door knob 22h, a bed 22i, an IV pump 22j, medical instruments 22k, a stationary patient table 22l, and a patient overbed table 22m. Although the central computer 20 functions as the disinfection hub in this room, essentially any standard room device can become the disinfection hub. For example, essentially any device in the room with the ability to communicate electronically (e.g. wirelessly) with other devices and with the network may provide the function of a disinfection hub. This may include devices that include electronics with associated communications transceivers or devices that are provided with electronics and associated communications transceivers for the purpose of functioning as a hub. To illustrate, the central computer or another electronic device with network communication capability could be provided with software that allows existing hardware to be used as a hub. Alternatively, a device without electronics or network communications, such as a soap dispenser, could be provided with a controller and communications capabilities to permit that device to function as a hub.

Figure 5:
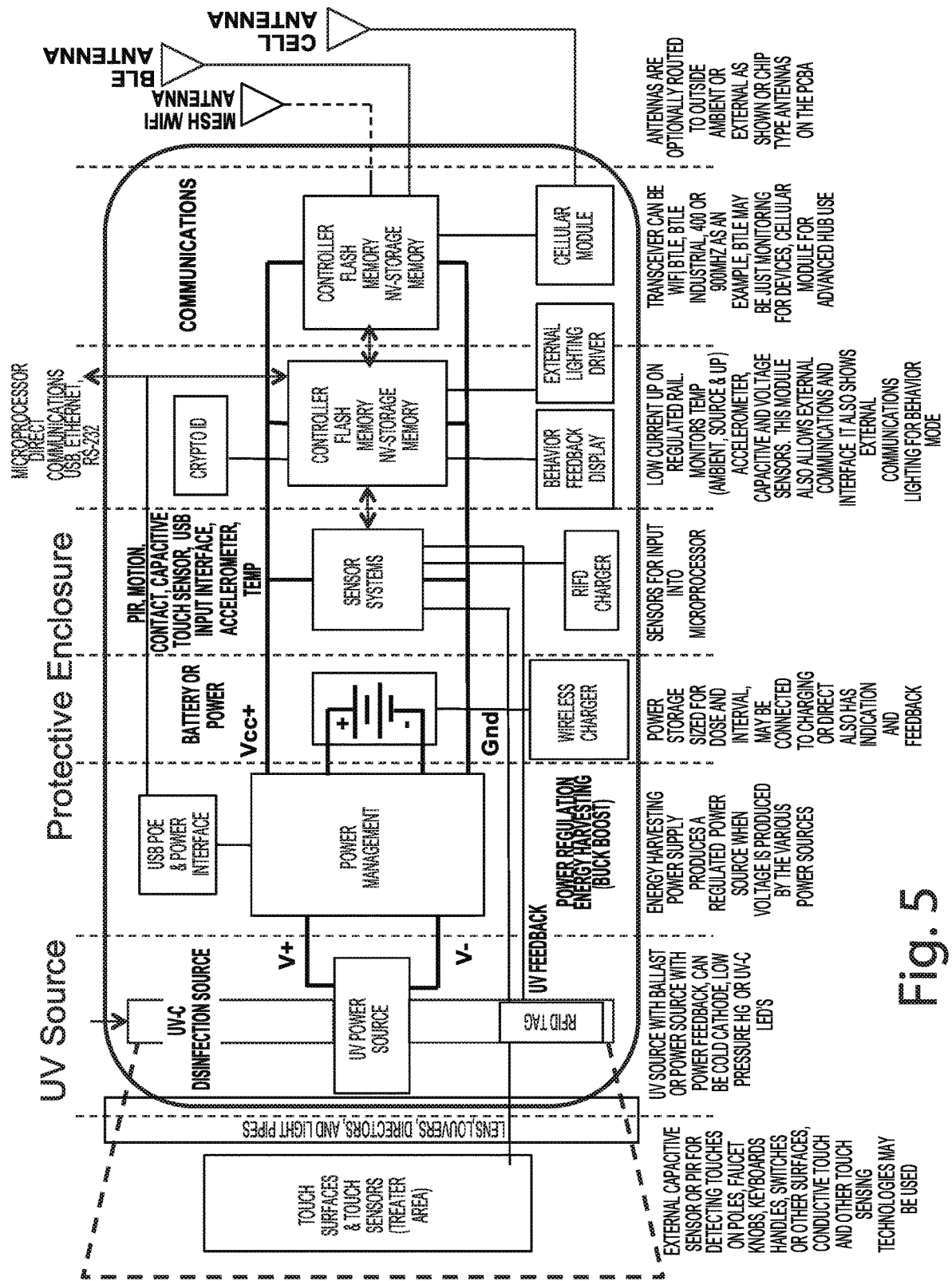
FIG. 5 illustrates an embodiment of the electronics of the disinfection control system. It includes communications, source UV and control, RFID to track lamp EOL, control and drivers for a user feedback and hub functions that may be implemented when used as a hub.

FIG. 5 shows an exemplary disinfection control system 30 that can be configured as an Internet-of Things ("IOT") hub or node within the network, such as network 10 discussed above. The UV disinfection control system 30 of this embodiment has a UV-C power source 32 that enables UV-C intensity control and contact time control. The UV-C source 34 may be essentially any UV-C source capable of generating UV-C light at the desired intensities. For example, the UV-C source may be a cold cathode lamp, a low pressure mercury lamp or UV-C light emitting diodes. The control system 20 of this embodiment also includes a controller 36 that performs various functions. In this embodiment, the controller 36 is coupled to a sensor system 24 that provides the system 30 with various sensor inputs, such as PIR sensors, motion sensors, capacitive touch sensors, accelerometer and temperature sensors, and may provide an interface for RFID reader 26. The data collected by these sensors may assist in controlling operation of the system 30 and in collecting data that may be relevant to tracking on infection-related events. The touch sensing aspect of this design provides desirable functionality because touch events can be used to trigger UV source activation, to interrupt disinfection cycles and to provide valuable data in making dynamic adjustments to the UV parameters, such as cycle time and source intensity. Although the PIR solution for heat and motion may be popular today, capacitive touch sensing is another solution for grab handles, and non-switch surfaces.

The controller 36 of this embodiment also monitors the current and voltage within preset ranges for proper operation and lamp diagnostics. Sources can be open, shorted, impedance can change causing different operating voltages that the controller 36 identifies and sends to a remote network component, such as a network server on the cloud, as a service request. In this embodiment, the UV-C power source 32 monitors the current and voltage to the UV source 34 and feeds that information back to the controller 36. The controller 36 may also include volatile and and/or non-volatile storage memory. For example, the controller may include flash memory.

Figure 8:
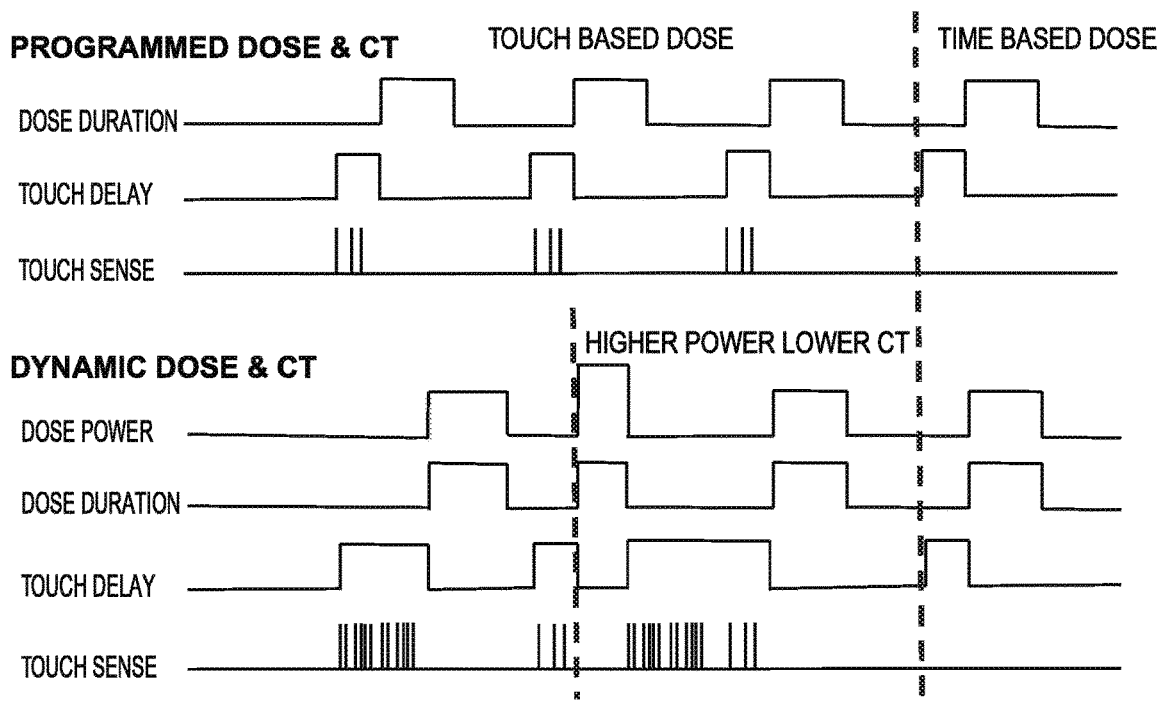
FIG. 8 illustrates an example of a low dose UV-C drive signal, the top control shows the timed dose for continued dosing of the surface at an interval. The bottom drive signals show adjusting lamp power to compensate for faster touch intervals by increasing lamp power.
Figure 9:
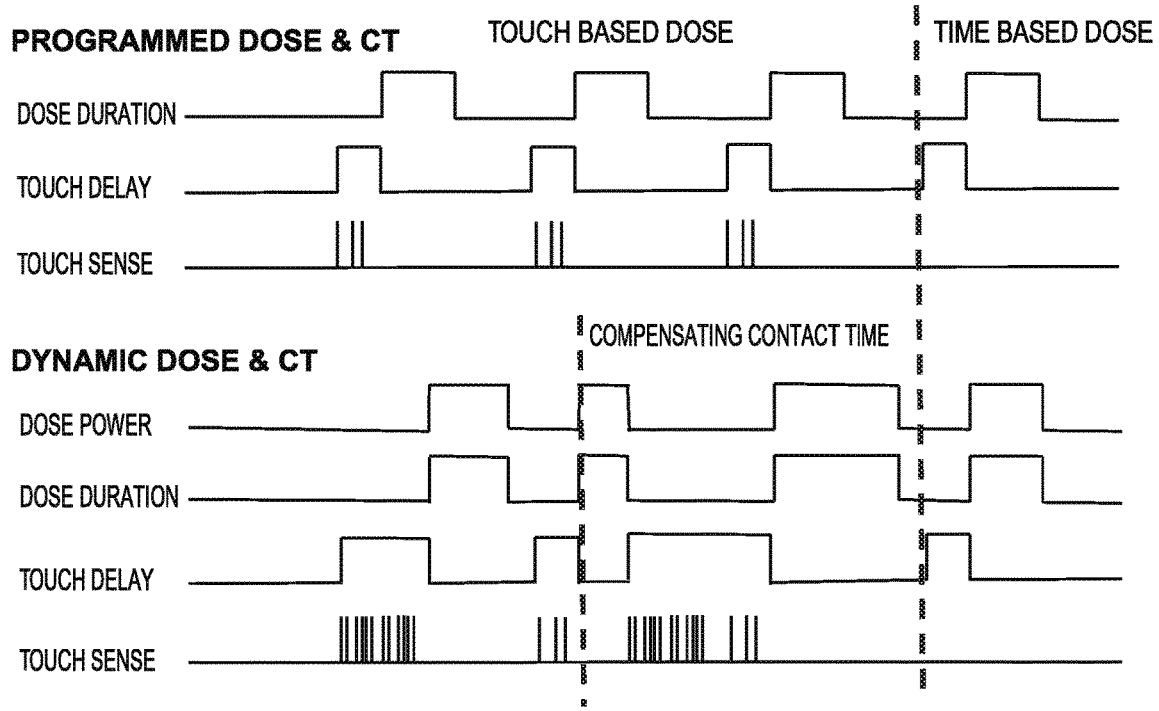
FIG. 9 illustrates low dose UV-C drive signal, the top control shows the timed dose for continued dosing of the surface at an interval. The bottom drive signals show adjusting contact time for faster intervals by increasing contact time.
Figure 42:
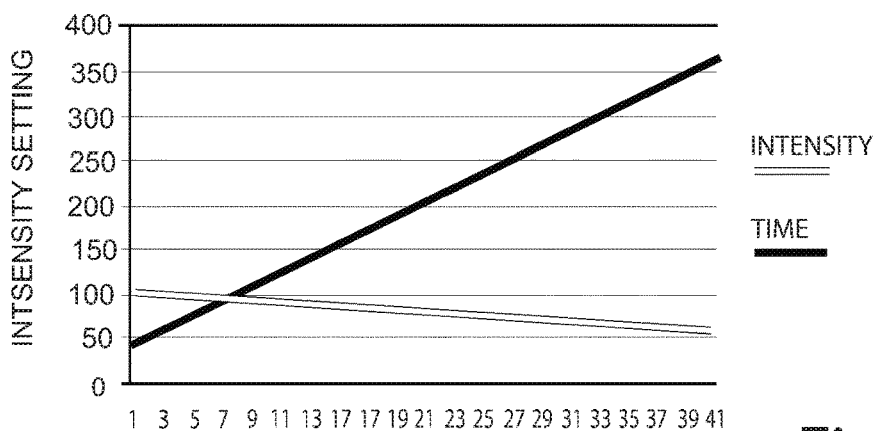
FIG. 42 is a graph of calibrated dynamic time versus intensity.

In this embodiment, the UV source 34 and UV disinfection control system 30 have integrated RFID capabilities. The RFID tag 38 located on the UV source 34 allows the controller 36 to uniquely identify the UV source 34 using the RFID reader 26. This allows the control system 30 to properly validate the UV-C source and also allows new thresholds (and other operating parameters) to be transferred to the controller for that lamp. These thresholds may change by manufacturer or lamp time and can also be changed over time as learning progresses. The UV power source 32 of this embodiment is an amplifier circuit and the amplifier gain can be changed to increase or decrease intensity. This is essentially changing the lamp voltage within allowed thresholds, higher thresholds will most likely impact source life. These intensity thresholds may also be contained for each lamp. The hours at each intensity level are important as the controller 36 accumulates the time at each intensity to enable total end of life calculations. Adjusting and applying the power to the UV lamp at controlled intervals allows the controller 36 to control the UV-C power output. This allows high speed touch iterations to be treatment compensated dynamically. It is not typically ideal to run at the highest intensity as it impacts the source with shorter life. With lower intensity lamp, longer duration "on" cycle times (or dose times) may be desired to obtain adequate disinfection as shown in FIGS. 8 and 9. This is a dynamic control that increases dose momentarily during busy times. A running average of busy times and expected dose changes can be preprogrammed and the algorithm then modifies these dynamically as touch iterations change. An example of the algorithm requires first having a setting of the required dose. Each unit may, for example, store that required dose as intensity level and contact time at a calibrated distance. The USB interface 42 (or other wired communication interface, such as Ethernet or RS-232) or a BTLE interface (or other wireless communication interface) can be used to allow external electronic devices, such as a smartphone, tablet computer or other mobile electronic device, to automatically write UV parameters and other values relevant values into the control system 30. In some applications, the UV source is fixed at the specific distance from the target disinfection surface and a UV-C intensity meter is used to assure dose for that interval. This can be used to assure that every device has been calibrated to preset standards. Some lamps are manufactured in glass rather than quartz and will not emit UV-C. This type of quality and output calibration can be used in the field and in the production facility. The OEM's manufacturing the device can assure proper installation configurations over many mounting options and distances with a go-no-go answer for limits of performance. The expected lamp life also changes dynamically as these minimum intensity expectations are set. An aging percentage may be added to these numbers to account for source degradation over the expected source life. The chart of FIG. 42 shows a typical curve calculated for the dynamic dose curve. The dose data vs. power is defined and measured in the lab first, stored and averaged over life and then verified at the surface in testing. It should be noted that the range or intensity span is set and designed for optimal lamp life and typically over designed. The starting calibration values include the span of intensity. This sets the range of time allowed and may be limited by, UV exposure limits, such as eye contact thresholds. In the case shown, the thresholds are set by OSHA standards for UV-C contact and exposure. In some applications, it may be desirable to include additional security-related components in the control system 30. For example, in the embodiment of FIG. 5, a crypto chip 44 is included to provide each unit with a unique ID, but other mechanisms for identifying each unit may be provided. The security may also be augmented with a token and SSID for security purposes stored in non-volatile memory set up by installation staff through BTLE or USB program for WiFi interface. This crypto ID is for an additional security measure and is designed to create a disinfection and touch tracking device that can have the security required to write directly into an electronic medical record.

In this embodiment, the disinfection control system 30 has BTLE and Mesh capability; the mesh network can be Zigbee or BACNet to meet specific regulatory requirements or hospital specifications. In extreme monitoring solutions a cellular module may be used to communicate the data to the cloud as an alternative source of information gathering. As shown, the control system 30 may include transceivers and antenna matching circuitry 28a and a cellular module 28b that are coupled to corresponding antennas 29a-c. The controller 36 may also have ports to allow directed wired connections, for example, using USB, Ethernet and RS-232 protocols.

In some applications, the disinfection control system 30 may have the ability to operate on battery power. The battery version may be provided with a battery 48 and a wireless charging circuit 46 for remote solutions and may be recharged when docked. The optional wireless charging 46 and battery 48 is used for mobile applications like remote inventory areas or procedure augmentation and support. An example is a Foley Catheter procedure, the remote disinfection device can be used to further disinfect the package by easily placing the disinfection device nearby the package. Further, crash carts and infrequently used tools may be good applications for these types of systems.

In typical applications, it is beneficial for the control to be versatile to allow embedding into the various applications mentioned in the disclosure. Because disinfection effectiveness is a product of intensity and time at a given distance, the calibrated numbers set the starting point or dose at a given distance. This control system 30 may, however, be dynamic to allow many different distance and mounting options on various devices like vitals monitors, glove boxes, IV pumps etc. Light switches, bed rails all need to know when touch happens to enable the low dose solution.

As noted above, the UV source (e.g. UV-C lamp) may have an RFID tag 38 and the control system may have an RFID reader 26 to understand when the UV-C lamp 34 has reached end-of-life to encourage safe use and maintenance. UV-C devices typically have a life based on hours of life as they self-destruct due to the nature of UV-C. The control system 30, for example, through the controller 36, may keep track of lamp "on time" by reading from and writing to memory resident on the RFID tag 38. The control system 38 may adjust the actual "on time" by a correlation factor to compensate for lamp intensity. For example, the control system 30 may increment the lamp life counter by less than the actual "on time" for operation that occurs when the lamp intensity is reduced and may increase the lamp life counter by more than the actual "on time" for operation when the lamp intensity is increased. The correlation factor (or intensity adjustment factor) may be provided by the lamp manufacturing, may be determined through tests of the UV lamp or may be estimated based on past experience.

The control system 30 may also have USB and Power over Ethernet ("POE") circuitry 37 to enable simple usage without additional power cord requirements for this equipment. The power management circuit 39 of this embodiment is designed as an energy harvesting power supply as to allow inputs from power generating sources and various voltages enabling flexible power adaptation. The circuit is designed to allow AC power to pass through so that the host piece of equipment is undisturbed. This can be helpful in many applications as these environments have stringent electrical drainage requirements for safety. For example, when the UV disinfection system 30 is integrated into another electronic device, the power management circuit 39 allows the UV disinfection system 30 to draw power from the power supply for the host electronic device. This allows only one outlet to be used and minimizes the confusion when plugging in the device(s). The internal power management circuit 39 may be designed to use wireless, USB, DC and battery sources. The harvesting circuit enables the disinfection device to be powered from the current in the power cord of the host device. The battery can be charged if even a small current can be harvested charging the battery over time enabling a good use profile. The UV disinfection control system 30 can be implemented without a harvesting circuit and may instead be powered separately from the host device. For example, the UV disinfection control system 30 may use a dedicated source of power when it is not integrated into a host device.

In this embodiment, the control system 30 includes behavior feedback outputs 43 that drive haptic vibration devices, sound outputs and LED lights that are configured for training and behavior modification (as described in more detail below). Similarly, the control system 30 may include an external lighting driver 45 that enables alternative lighting and could be an RGB LED allowing software configurable surface and indication lighting. This lighting option would allow light patterns and colors to be configurable. This alternative lighting may be used in connection with the disinfection user interface for feedback or may be used to provide supplemental lighting, such as a work light, with all configurable options.

Figure 6:
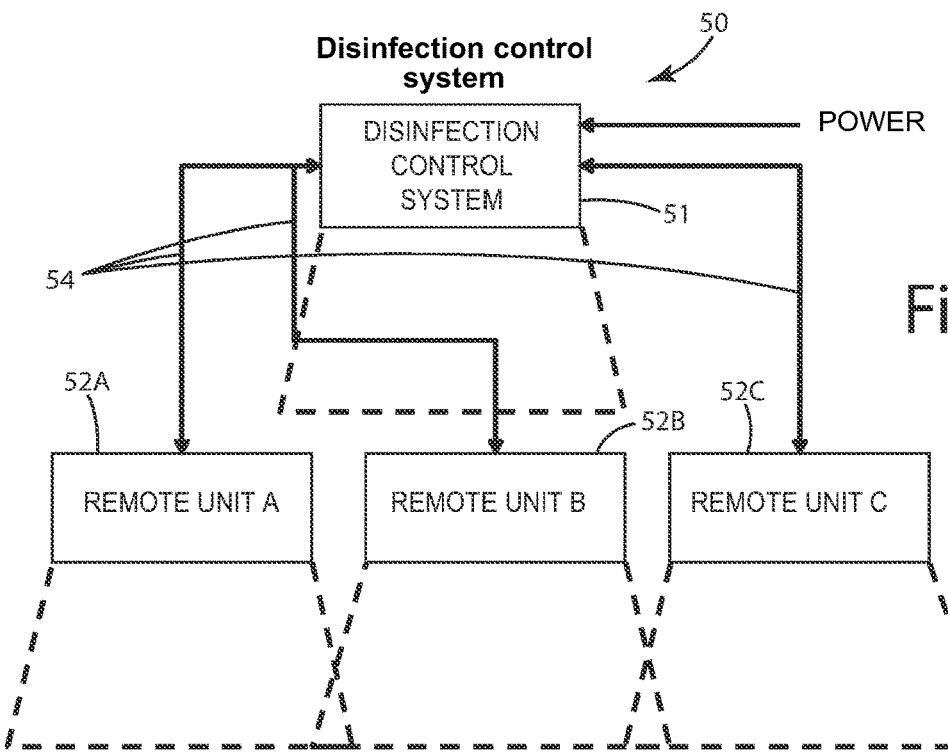
FIG. 6 illustrates a system as depicted in FIG. 5 but with multiple UV-C sources and motion detection devices allowing one control and power supply for multiple disinfection devices.
Figure 39:
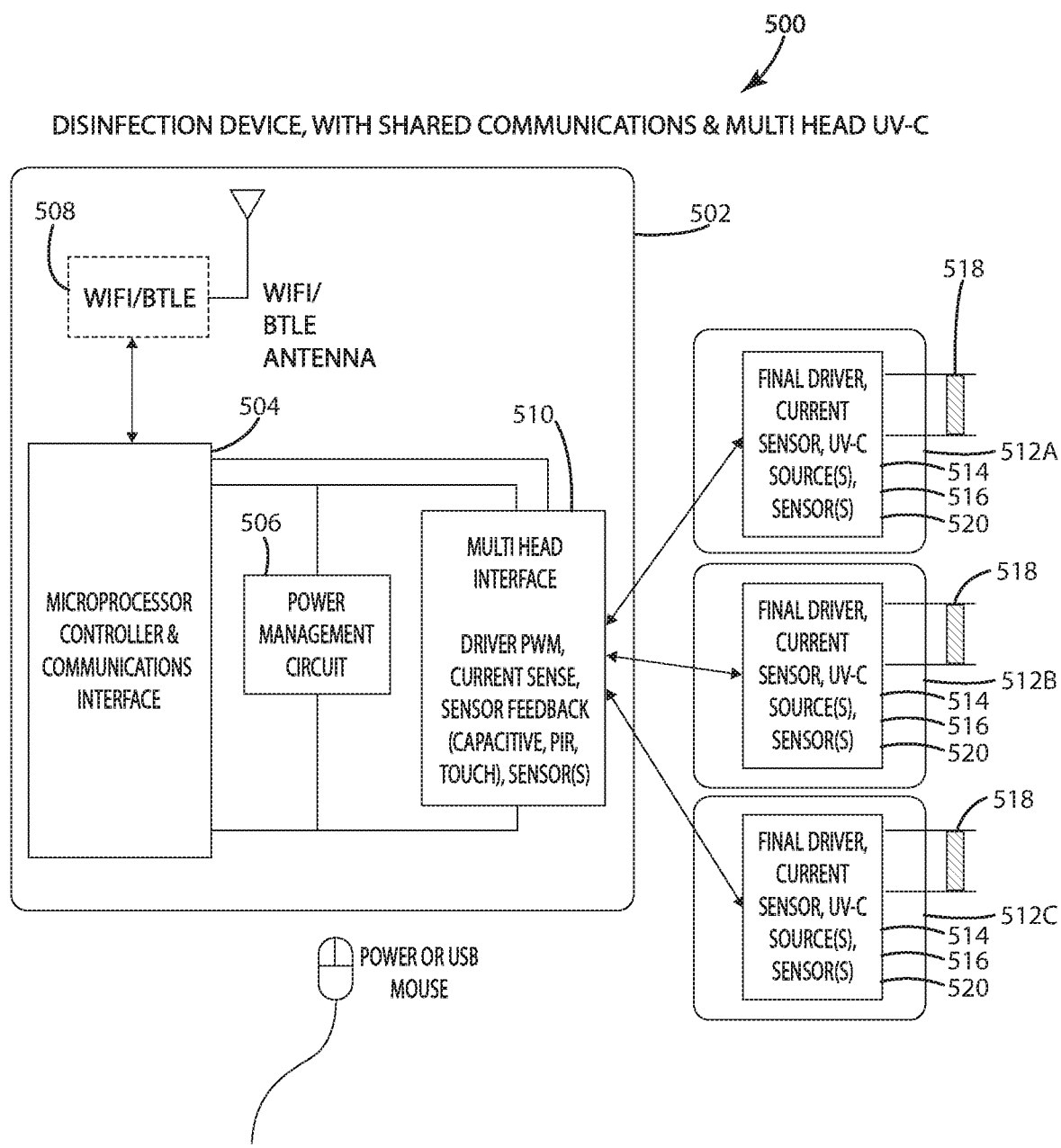
FIG. 39 is a schematic representation of a disinfection device with shared communications and a multiple UV-C heads.

FIG. 6 is a high level schematic representation of a disinfection control system 50 controlling and monitoring several UV-C remote units 52a-c. In this embodiment, disinfection control system 50 includes a primary unit 51 that includes UV-C source and control circuitry capable of controlling operation of UV-C source in the primary unit 51, as well as the remote units 52a-c. In this embodiment, the remote units are connected via a simple harness 54, which may include communication/control wires and, in some applications, power wires that allow the remote units 52a-c to be powered by the primary unit 51. In this embodiment, the touch sensor inputs and UV-C source (not shown) for each remote head unit are located in that remote head units. By using multiple heads with one control, costs can be kept to a minimum and larger and more complicated surfaces can be disinfected. For example, different UV source can be directed toward different regions of a complex surface to help ensure that the entire surface is properly disinfected. Another embodiment of a disinfection control system with multiple UV heads is shown in FIG. 39. In this embodiment, the disinfection control system 500 generally includes a control module 502 having a microcontroller 504, a power management circuit 506, a wireless communications transceiver 508 and a multihead interface 510. The multihead interface 510 may be coupled to a plurality of UV heads 512a-c. Although shown with three UV heads 512a-c, the number of UV heads may vary from application to application. In this embodiment, each UV head 512a-c includes a final driver 514, a current sensor 516, a UV-C source 518 and one or more touch sensors 520. The term touch sensor is used herein to refer to essentially any sensor capable of sensing when a surface is physically touched, when an object come within sufficient proximity of another (even if no physical contact occurs) or when any other form of relevant interaction occurs. In some applications, a capacitive sensor or inductive sensor may be provided to determine when a device has been touched or when an object comes within sufficient proximity to the device. In other applications, a PIR sensor may be provided to sense motion within proximity of a touch surface. These and other types of sensors may be incorporated into devices in accordance with an embodiment of the present invention. In this embodiment, the microcontroller 504 includes a communications interface for communicating with the communications transceiver 508. Although the illustrated embodiment includes a WiFi and/or BTLE transceiver, the present invention may be implemented using essentially any wired or wireless communication protocol. As noted above, the UV disinfection system may be integrated into a primary electronic device, such as a vitals monitor or IV pump. For convenience, the UV disinfection system 500 may be configured to draw power from the preexisting power supply for the primary electronic device. In such cases, the power management circuit 506 may be connected to the preexisting power supply (not shown). In other applications, the UV disinfection system 500 may be a standalone device that is separately connected to main powers. In standalone applications, the power management circuit 506 may be configured to receive power directly, for example, via a power cord or a USB cable.

With the disinfection control system having BTLE we can list the associated MAC addresses and ID's associated with that station. When researching infection, this information will be helpful. It is also helpful when scoring activity and enabling the potential of infection by contact probabilities. With more people the odds of infection will go up and this input helps to identify an aspect of that equation.

Figure 7:
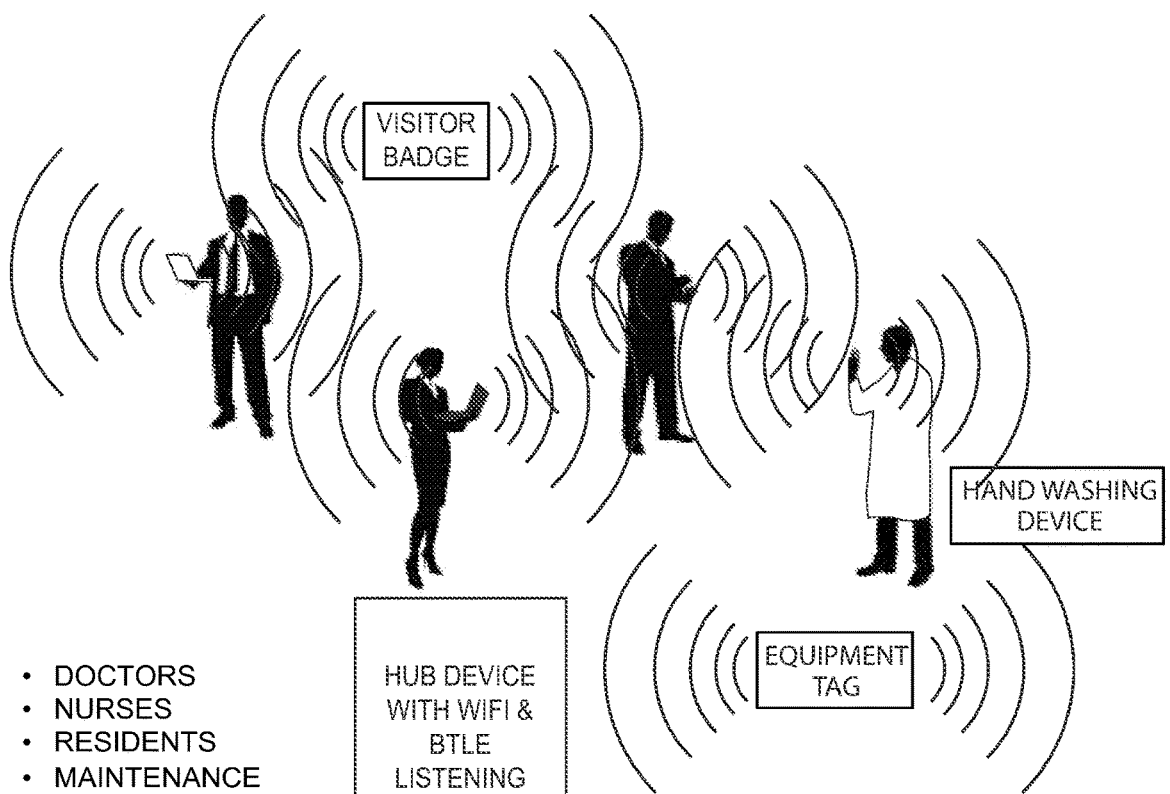
FIG. 7 illustrates a disinfection control system listening to the advertising of electronic devices to track proximity by measuring signal strength.

The UV disinfection network may be configured to track the location of assets within the network. FIG. 7 illustrates an embodiment of the present invention in which certain assets are tracked by listening to the advertising of electronic devices to track proximity by measuring signal strength. For example, the hub device may be provided with WiFi and BTLE listening circuitry that can be used to identify electronic device that are sending advertising transmissions. In this embodiment, other assets may be provided with circuitry capable of transmitting WiFi and/or BTLE advertising transmissions. For example, WiFi and/or BTLE transmitters or transceivers may be incorporated into visitor badges and equipment tags. As an alternative or supplement, the disinfection network may include other types of asset tag or ID tag systems. For example, hubs or other devices in the network may be provided with an asset tag/ID tag reader and each mobile assets may be provide with an asset tag/ID tag that can be read by the reader. In one embodiment, the disinfection network may implement an RFID-based system in which the readers are capable of recognizing the presence of RFID chips incorporated into ID tags or other types of asset tags when the ID tags or asset tags come within sufficient proximity of the readers.

FIG. 8 shows a typical low dose cycle and iteration on the top and a power enhanced dose on the bottom. In both cases, dose is enhanced by the subsequent dose cycles over time but in the power enhanced cycle the touch iterations look to be too close so the control system then increases power to reduce cycle time or contact time. The contact time is calculated by typical touch iterations and a basic timed sequence to enhance the low dose performance FIG. 9 shows a typical low dose UV-C cycle on the top and a time enhanced cycle on the bottom. The bottom shows a period of more touches preventing the unit from turning on and the system compensates by allowing a longer contact time dose for a cycle to catch up. This is then augmented by the subsequent additional dose cycles over time. The present invention may be configured to respond to touch interruptions during a UV disinfection cycle by causing the UV disinfection source to run for an accumulated time that totals the desired cycle time. For example, in a situation where the desired disinfection cycle time is six minutes, the disinfection control system can be configured to run the UV source for a total of six minutes, excluding any time that the UV source is turned off because of a touch interaction or a touch delay. To illustrate, if the UV source has been running for two minutes when a touch event occurs, the control system can turn off the UV source until the touch event has stopped for a period of time that is equal to the touch delay. After that, the control system can run the UV source for an additional four minutes (e.g. the amount of time remaining in the six-minute cycle before the touch interruption). Similarly, if there are two interruptions during a UV disinfection cycle, the control system can have three separate on-times that total to six minutes. In some applications, it may be desirable to extend the total cycle time of a disinfection cycle if that cycle is interrupted by the occurrence of a touch event. For example, if it is determined that additional UV source on-time is required to provide the same level of UV disinfection as a continuous disinfection cycle, then the total cycle time can be increased by the amount of time needed to provide equivalent disinfection. This may occur if, for example, if it takes some time for the UV source to reach an effective intensity or if the touch interruption is of sufficient length to allow some recovery of the bioload. Further, in some applications, each touch interaction may represent additional bioloading and the UV disinfection control system may be configured to respond to a touch event by restarting a full disinfection cycle after each touch event (e.g. the control system attempts to run a full six-minute disinfection cycle after every touch). It should be noted that, in some applications, the maximum allowable exposure is 6 mJ/cm2 for eye contact and overall exposure of 60 mJ/cm2 for 8 hours. However, the maximum allowable exposure may vary and the present invention may be readily modified to comply with any exposure limitations that may apply now or in the future.

Figure 16:
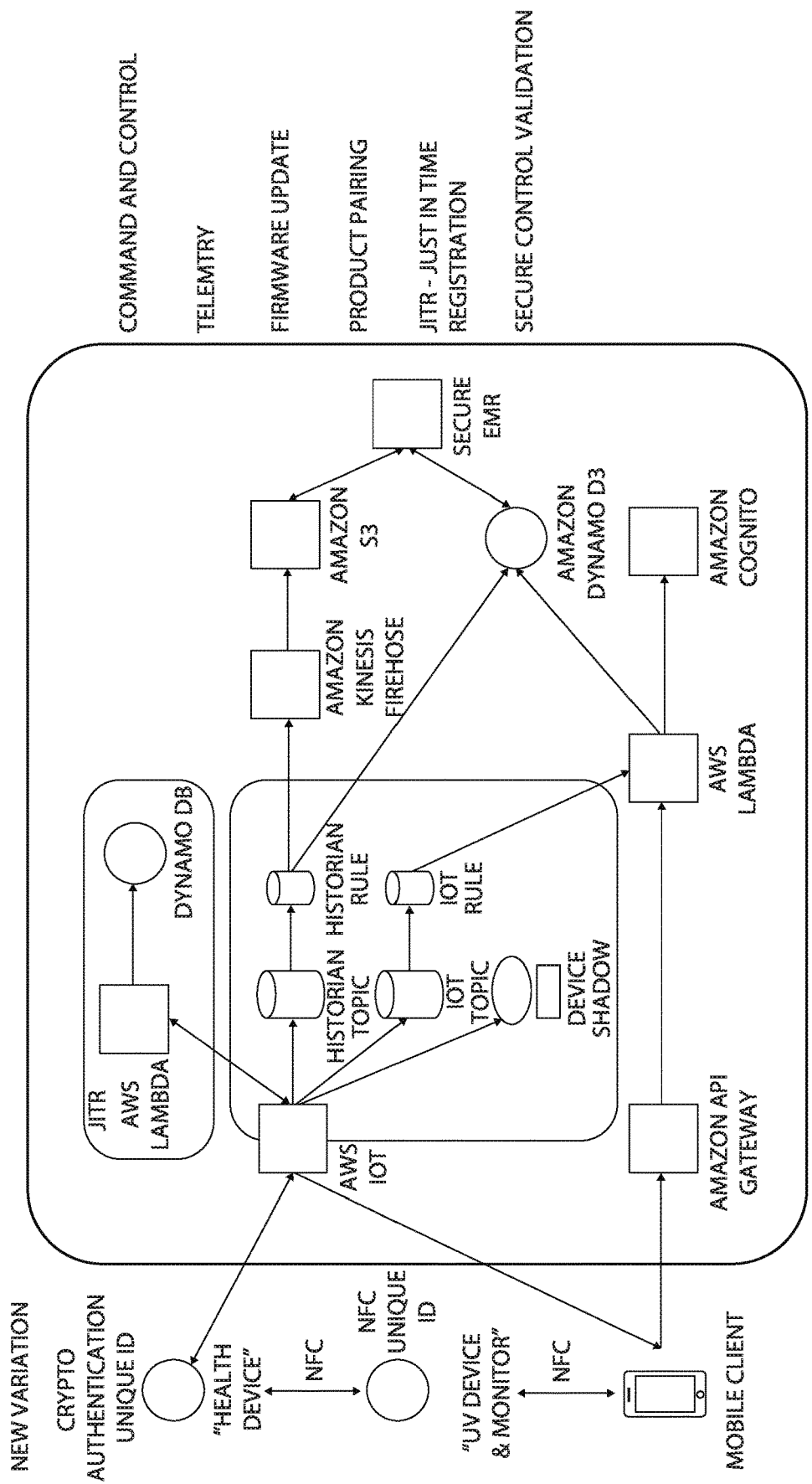
FIG. 16 shows a diagram of a network system that has a secure network and can be used for electronic medical record use.
Figure 17:
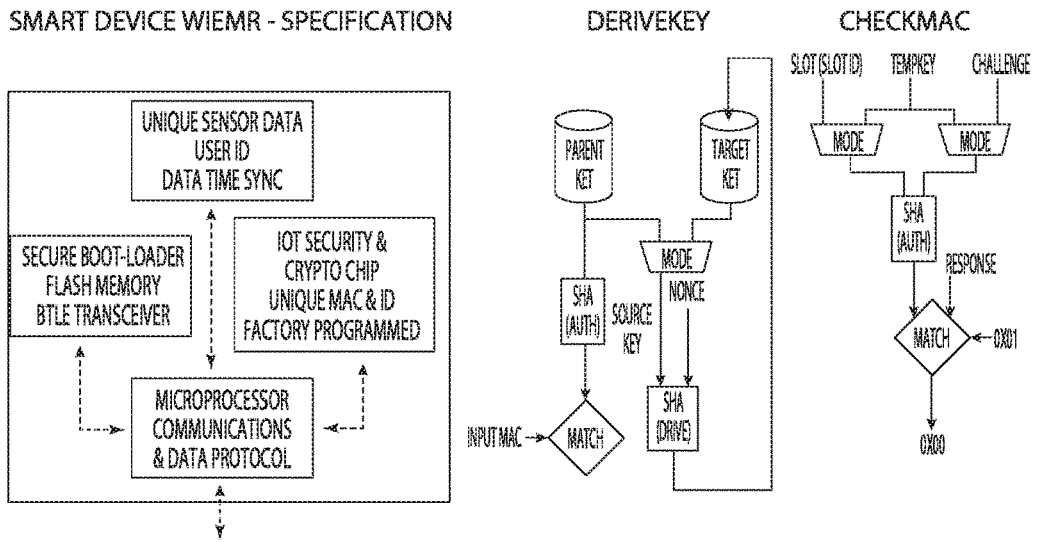
FIG. 17 illustrates one embodiment of the crypto chip from Atmel that enable secure programming and communications for IOT devices, it shows the passage of the crypto key and how the security is handed off to the device.

In some applications, it may be desirable to enable writing secure data into electronic medical records ("EMR"). When writing data into the EMR, it may be desirable to have enhanced security in the network. For example, the embodiment of FIG. 5, the control system 30 includes a crypto chip with a crypto ID. The crypto chip may be an Atmel crypto security chip or essentially any other suitable security chip. Similarly, FIG. 16 shows a network that enables just-in-time registration and maintains a mirror database for your device ID. This connected with the crypto challenges, the system can authorize and verify users and use directly. The importance of this is to enable writing secure data into the EMR (Electronic Medical Record). This database structure enables secure upgrades, easy device adding and recognition, all in a secure format. It should be known that the primary means of expected data transfer is WiFi but the device is configured with multiple communication options. WiFi and mesh along with BTLE for local configuration and calibration is a common configuration. In some applications, wired communications may be employed. FIG. 17 illustrates one embodiment of the crypto chip from Atmel that enable secure programming and communications for IOT devices, it shows the passage of the crypto key and how the security is handed off to the device.

Figure 10:
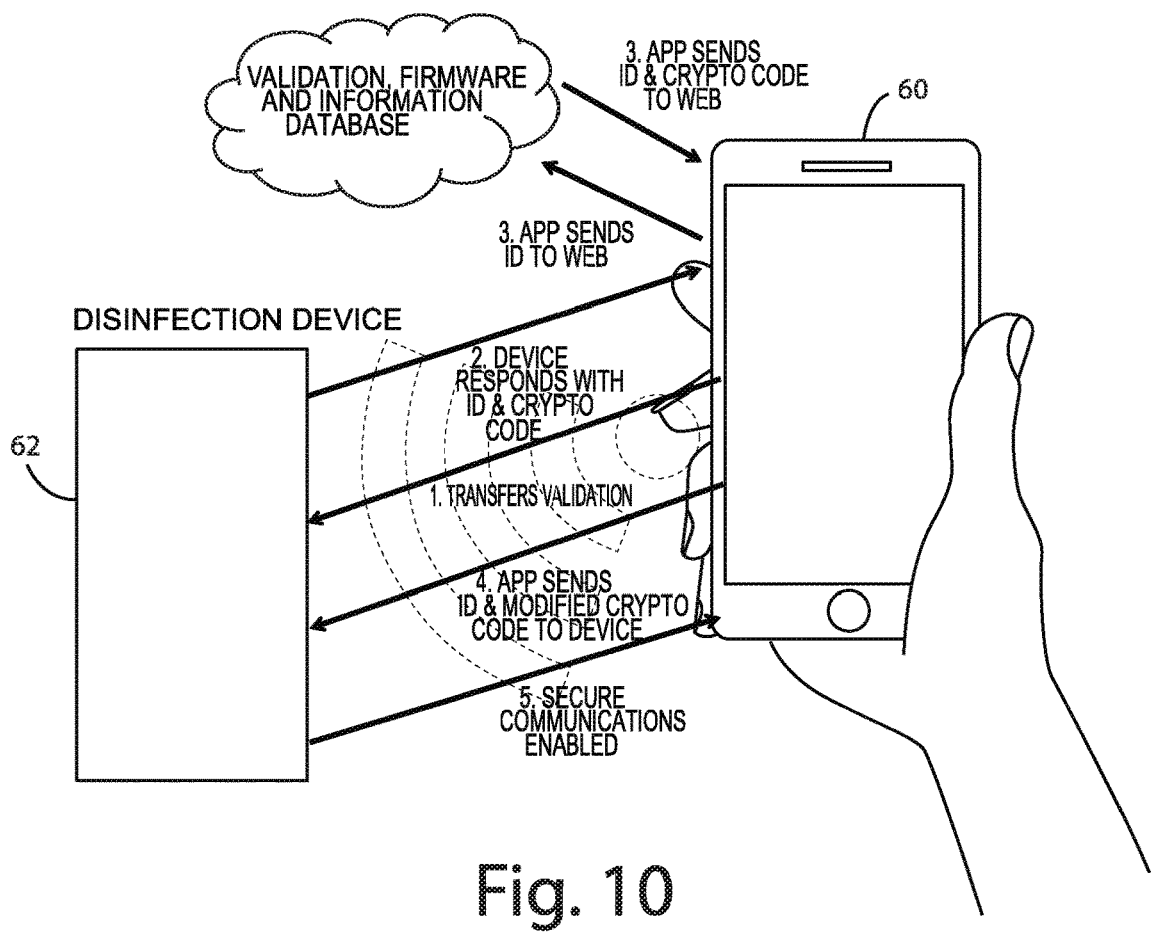
FIG. 10 illustrates a secure network communication using the crypto chip for communications and programming security.

In some applications, a mobile device may be provided to collect information from enabled devices. FIG. 10 is an illustration of a mobile device 60 collecting information from the disinfection or monitoring device 62. The mobile device 60 can be used where networks are difficult to access and can also be used to program and update these devices directly. If desired, the mobile device 60 and the enabled device 62 may communicate securely using the crypto chip ID. This enables an IOT safe communications and programming network for the proper users that can be authenticated for various level of use and interface.

Although the present invention is described in connection with various embodiments that implement conventional network systems and methods, the present invention may be implemented using a wide range of alternative network structures and network protocols. For example, the illustrated embodiments of the disinfection network are implemented using an Internet-based wide area network in which individual devices communicate through a hub to one or more Internet or cloud-based servers that are capable of collecting, analyzing and storing data. Disinfection networks in accordance with the present invention may, however, be implemented using essentially any local area network or wide area network structure, or any combination of local and wide area networks now known or later developed. Further, data storage, data processing and device control may be carried out by and distributed across any number of computers or processors. For example, in some applications, all data storage, data processing and device control may occur in a single computer or collection of computer associated with a local area network. Additionally, illustrated embodiments of the present invention are described in the context of a wide range of known wired and wireless communication protocols. Disinfection networks and disinfection devices in accordance with the present invention may be implemented using essentially any communications systems and methods now known or later developed.

Figure 18:
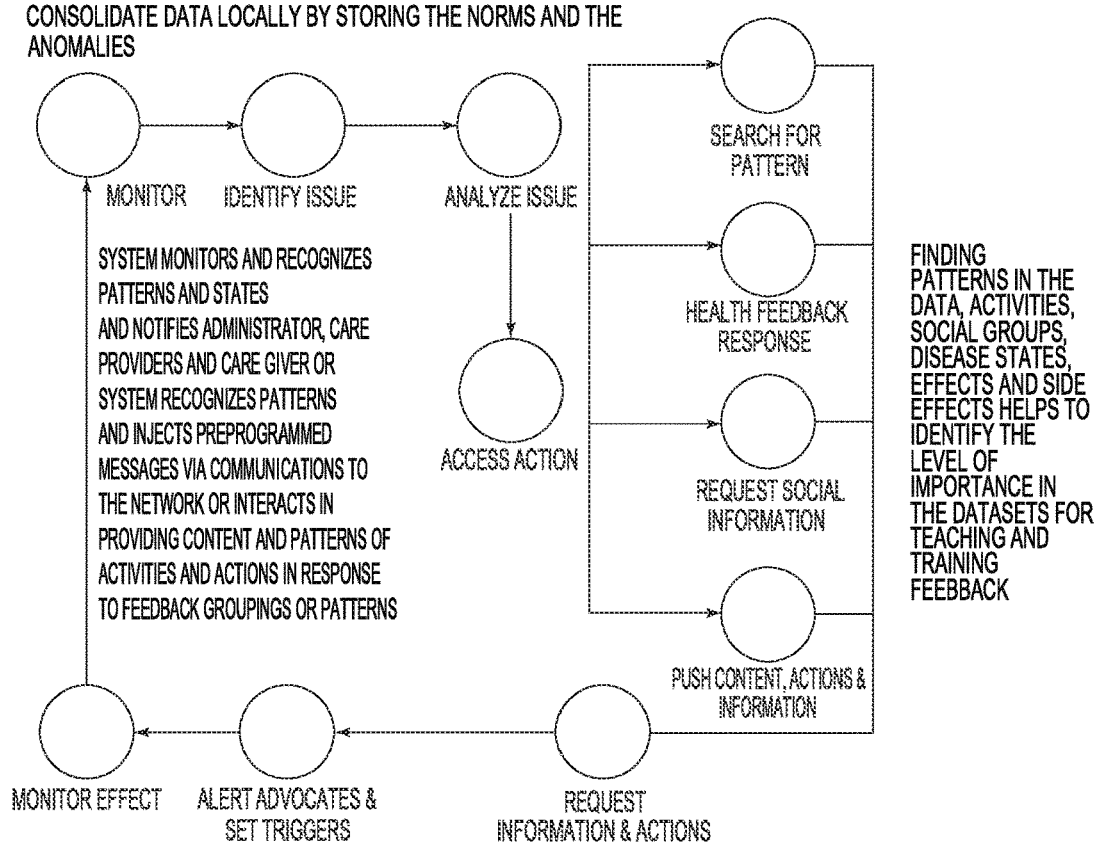
FIG. 18 illustrates a process to push social data to the disinfection network for training and analytics feedback. When a person is not utilizing hand washing or misses steps in the disinfection process this information is relayed to the user for instructional purposes.

In some applications, the UV disinfection network may be configured to monitor individuals' activities within the network and, when appropriate, provide messages to the individuals. The messages may be intended for reporting, instructional and/or training purposes. FIG. 18 illustrates a process to push social data to the disinfection network for training and analytics feedback. In this embodiment, the UV disinfection network may analyze workflows (e.g. actions and interaction between assets in the UV disinfection network) to determine whether a particular individual is following desired protocols. For example, when a person enters a room, but does not promptly interact with the soap dispenser or the faucet, the UV disinfection system may determine that the individual did not wash his or her hands. When an individual is not utilizing hand washing or misses steps in the disinfection process this information is relayed to the user for instructional purposes. If desired, it may also be communicated to the individual's supervisor or to others that might use the information. The workflow information may also be maintained in a database and used to understand the spread of infection or provide accountability.

D. Disinfection Interface

Figure 11:
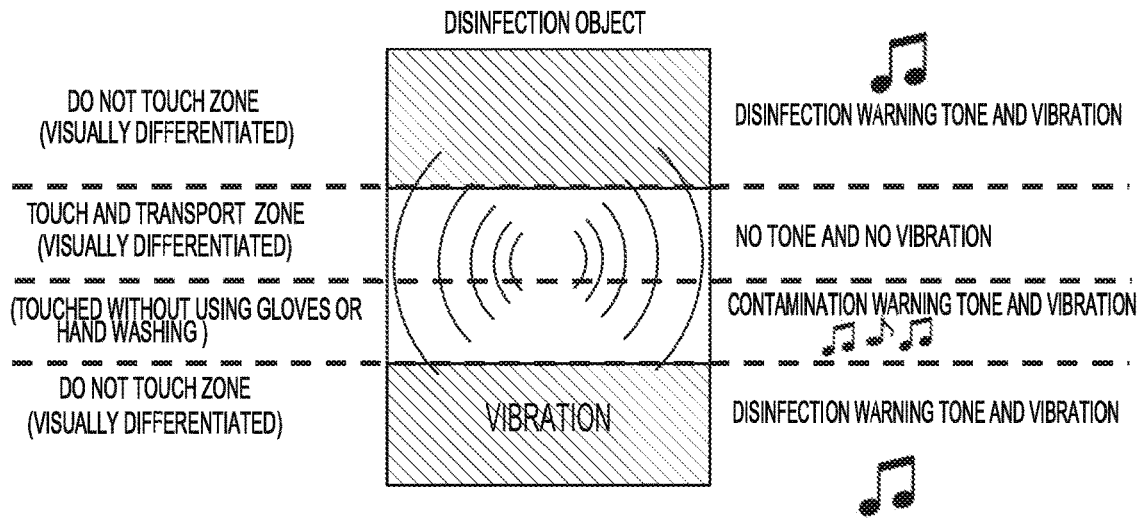
FIG. 11 illustrates a disinfection control language for communicating disinfection health and changing hand washing and disinfection behaviors.
Figure 25:
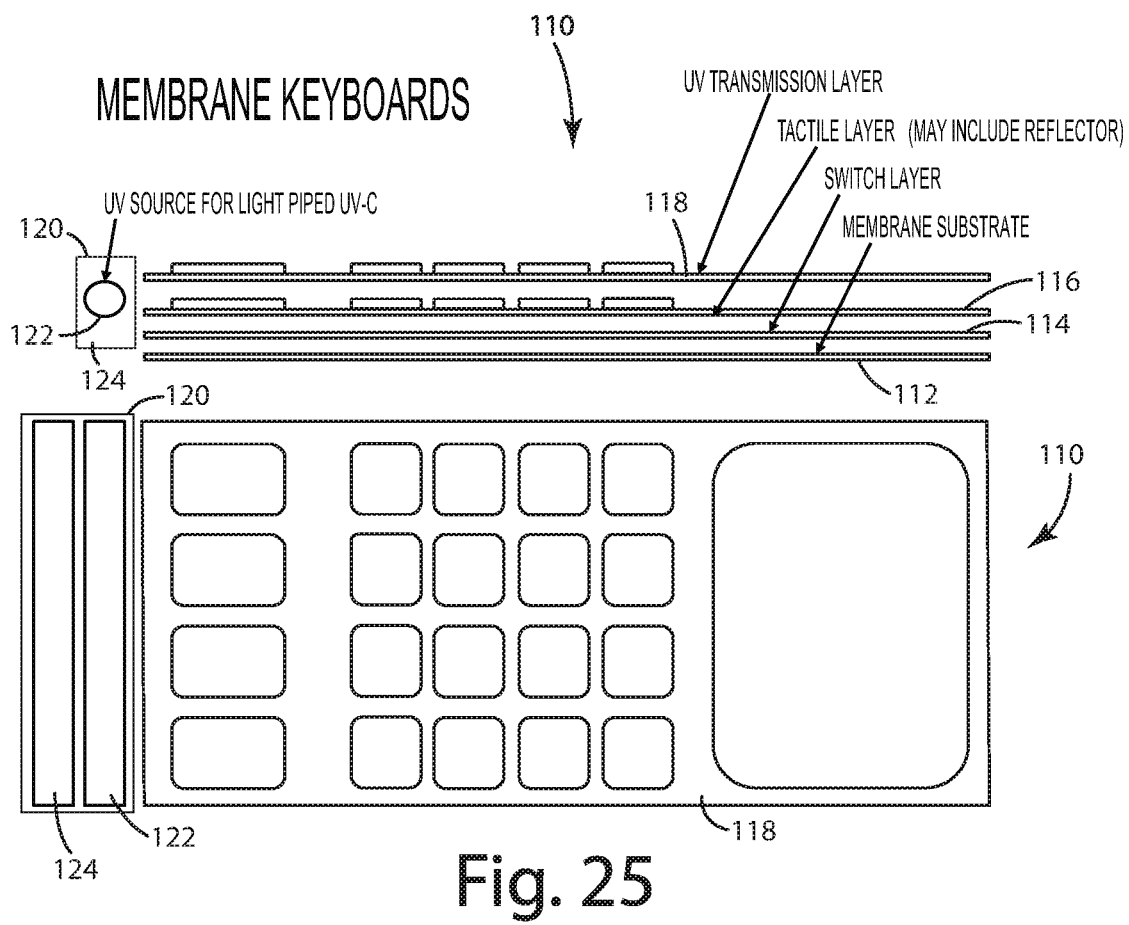
FIG. 25 shows the construction of a keyboard with an outer layer of material that allows UV-C 254 nm transmission. The layer beneath the light pipe has a reflective element and the construction enables a lamp to light the outer surface layer for surface disinfection.

In another aspect, the present invention provides a disinfection language that may be implemented as a contact interface or user interface for UV disinfection enabled devices. FIG. 11 illustrates the basic elements of one embodiment of a disinfection language. This is a design and feedback language that includes visual indication and other queues. At one level, the premise can be to create a safe touch zone for handling and UV disinfection to prevent and control infections while minimizing cleaning cycles. Encouraging staff to touch specific areas can initially be difficult. In use, each touch in specific touch and no-touch zones can be tracked providing immediate feedback and tracking. The statistics of biological transfer enable this information to be calculated in the health score and becomes valuable for best practices and workflow. The first visual queue is to provide the device with a design having specific areas indicated for touching and other areas identified as "no-touch" areas. These areas may include different surface texture, different color and/or any other visual differentiation. "Touch" areas will typically be areas that the UV-C disinfection system is capable of disinfecting, whereas "no-touch" areas will typically be areas that cannot be adequately disinfected by the UV-C disinfection system. When a no-touch area is touched, it will likely trigger the need for a supplemental device disinfection and cleaning (i.e. a disinfection and cleaning that cannot be carried out by an integrated UV disinfection device). In this embodiment, the no-touch areas will be configured to provide negative feedback when a touch or undesirable interaction occurs. The negative feedback may be essentially any form of feedback, such as a visual indication, a haptic buzz (e.g. vibration) and/or an error tone. The system may include additional or alternative forms of negative feedback, such as flashing lights. In this embodiment, the touch data is transferred to the cloud for that device ID and time. An IV pole can, for example, be monitored for touch and can also provide visual, haptic and/or audible feedback. Most medical equipment are shielded and have metal surfaces and can be easily monitored for touch. As a result, existing constructions can provide an area for no touch and an area for proper handling that is already differentiated. A capacitive circuit can be used to detect these touches over a large surface. Alternative circuits capable of recognizing a touch may also be used, such as an inductive circuit or a PIR sensor. Adaptive capacitance sensing like ALSentis can be used for handles and covered surfaces. Moisture sensors like continuity or capacitance across the surface can be used to detect moisture dose loading. Once the health care cleaning process has been initiated a flag is set in software. That flag is not reset until contamination has occurred outside the designated touch areas that can be automatically disinfected. This is a queue for initiating the cleaning priority process by touches and time—again calling on transfer statistics to build a priority list. The areas for touch can be as simple as grab handles and a keyboard as shown in FIGS. 12 and 25. An additional network or mesh layer can be easily enabled for encouraging hand washing by monitoring or interfacing to the data from the glove box and the hand washing or disinfection applicator. The system has built in API's that enable the combination of multiple data systems to better track touches and cleaning processes along with equipment. When an automatic disinfection zone has been touched we can optionally provide audible feedback. That tone would be different and would also be part of the overall score and feedback. These series of feedback tones and haptic responses will easily change behavior. This combined with automatic scoring and notifications by area, person, device etc. will drive behavior change and awareness.

FIG. 12 shows a grab rail 70 with capacitive sensing and integrated UV disinfection. Referring to the cross-sectional view, the grab rail 70 of this embodiment includes an inner metal structural core 72, a thermoplastic or metal reflector intermediate layer 73 surrounding the core 72 and a fluoropolymer outer layer 74. The outer layer 74 is transparent or translucent to UV light and to visible light. In this embodiment, the grab rail 70 can be illuminated in different visible colors, such as red, blue and green. For example, the UV disinfection control system may include visible light sources that are positioned adjacent to the outer layer 74 so that, when a visible light source is energized, the color of that light source permeates through the outer layer 74 and the outer layer 74 takes on the corresponding color. The UV disinfection control system may be configured to produce haptic feedback (e.g. vibration) and to make audible tones when the grab rail 70 is touched. FIG. 12A shows the grab rail 70 illuminated in red to indicate that the grab rail 70 is contaminated and needs to be disinfected. Upon contact with the red-illuminated gab rail 70, the control system may also cause a vibration and an audible tone to give haptic and audible warnings to the individual that touched the grab rail 70. With appropriate training, the warning signals may be used to direct the individual that touched the switch to wash his or her hands. In applications that track workflow, the data associated with the grab rail 70 interaction can also be linked to hand washing and other types of workflow. FIG. 12B shows the grab rail 70 illuminated in blue to indicate that it is currently being disinfected. If the grab rail 70 of this embodiment is touched while disinfection is underway, the UV source will be shut off until a predetermined amount of time has passed since that touch interaction ended. If desired, the grab rail 70 can be configured to emit haptic and/or audible feedback when a grab rail 70 undergoing disinfection is touched. FIG. 12C shows the grab rail 70 illuminated in green to indicate that the grab rail 70 has been disinfected and can be safely touched. The capacitive or touch sensor allows the UV-C source to be turned off when a touch occurs to protect the user from exposure. After the touch has been terminated we then delay for a defined time and then enable a treatment cycle.

The grab rail 70 of FIG. 12 is also monitored and disinfected by a disinfection control unit. As noted above, the outer layer 74 of the grab rail 70 may be manufactured from a plastic material, such as a fluoropolymer. Further, the reflector layer disposed beneath the outer layer 74 may be a thermoplastic. If desired, the plastics used may have carbon or conductive properties like the ones used for static build up and prevention. These conductive properties can be the basis of a capacitive touch indication that detects the touches that enable the disinfection process. Between the reflective materials and the plastics, this technology can be integrated into about any surface. The reflectors or conductive materials are aligned as an input much like a heart rate sensor and the change in impedance produced by grabbing the surface enable the touch indication. For example, in one embodiment, the sensor(s) may be calibrated to have a value in the "not-touched" state and then another reaction in the "touched" state. These values may, in some applications, be calibrated with the smallest interactions and with less mass. An example would be to have free air for bedrails for the "not-touched" state, then using a single finger as a "touched: state value across the surface. This calibration may facilitate recognition of a wide range of touch interactions.

FIGS. 13A-C show a disinfection control system used in a light switch 80 with the behavior feedback. In this embodiment, the switch may be manufactured with an integral UV disinfection system as described elsewhere in this disclosure. The internal UV light source may be configured to transmit UV light into the switch toggle 82 and to the switch cover plate 84. For example, the switch toggle 82 and the switch cover plate 84 may be manufactured from UV transmissive material so that the UV light generated internally can pass through the cover plate and switch toggle to disinfect the outer surfaces. In alternative embodiments, only the switch toggle 82 may be manufactured from UV transmissive material. This may mean that the switch cover plate 84 is not treated or that sufficient UV-C light is emitted from switch toggle 82 to treat the exposed surface of the switch cover plate 84. In this embodiment, the switch 80 may also include a touch sensor (e.g. a capacitive sensor) to determine when the switch has been touched. The sensor may be configured to sense a touch of the switch toggle 82 and possibly the switch cover plate 84. In this embodiment, the switch also has the ability to illuminate in different visible colors, such as red, blue and green, to create haptic feedback (e.g. vibration) and to make audible tones. FIG. 13A shows the switch 80 illuminated in red when the switch 80 is contaminated and needs to be disinfected. Upon contact with the red-illuminated switch 80, the control system may also cause a vibration and an audible tone to give haptic and audible warnings. As noted above, the warning signals may supplement the visible feedback and be used to direct the individual that touched the switch to wash his or her hands. In applications that track workflow, the data associated with the switch interaction can also be linked to hand washing and workflow. FIG. 13B shows the switch illuminated in blue to indicate that the switch is currently being disinfected. If the switch 80 is touched while disinfection is underway, the UV source will be shut off until a predetermined amount of time has passed since the touch interaction ended. If desired, the light switch 80 can be configured to emit haptic and/or audible feedback when a switch 80 undergoing disinfection is touched. FIG. 13C shows the switch illuminated in green to indicate that the switch has been disinfected and can be safely touched. Another function of this switch is to turn off the UV-C source when touched wait a reasonable time to assure the user is clear and then restart the required dose as needed. This touch protection delay is utilized in the on to off and off to on positions.

Figure 14:
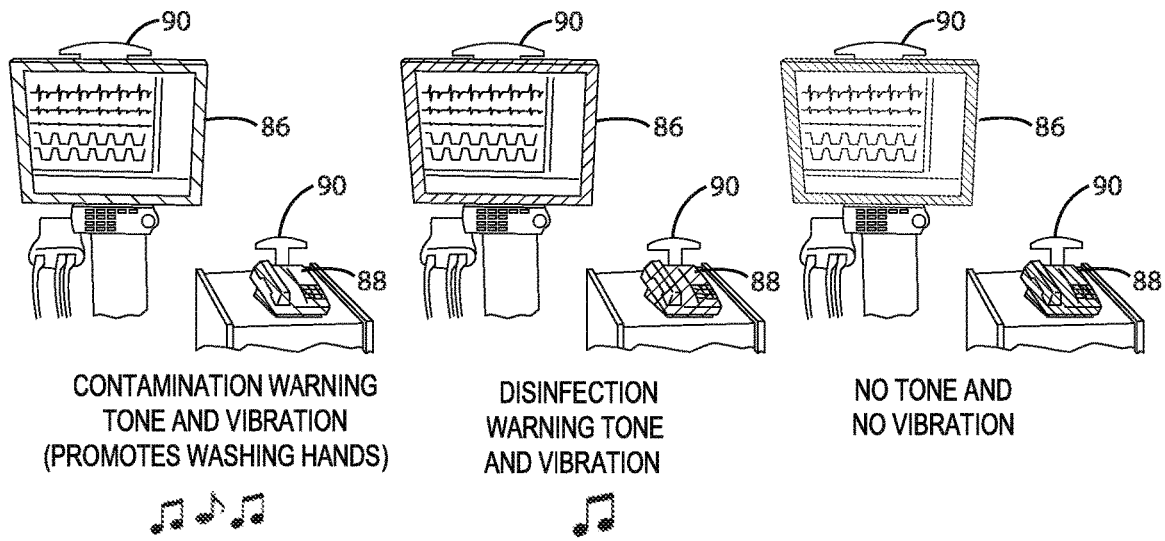
FIG. 14 illustrates other surfaces with the light, tactile and sound feedback.

FIG. 14 shows how the vitals monitor 86 and phone 88 may have the same feedback connected to the disinfection network. For the illustrated vitals monitor 86 and phone 88, UV disinfection is provided by external UV disinfection devices 90 which are positioned externally and broadcast UV light onto the touch surfaces of the vitals monitor 86 and phone 88. In this embodiment, each of the UV disinfection devices 90 may include visible light sources capable of emitting the visible light colors used in the disinfection language (e.g. red, blue and green in the illustrated embodiments). Further, each UV disinfection device 90 may have audible and haptic feedback circuits capable of generating the desired audible and haptic feedback signals when the monitored device is touched when contaminated or during disinfection.

Figure 15:
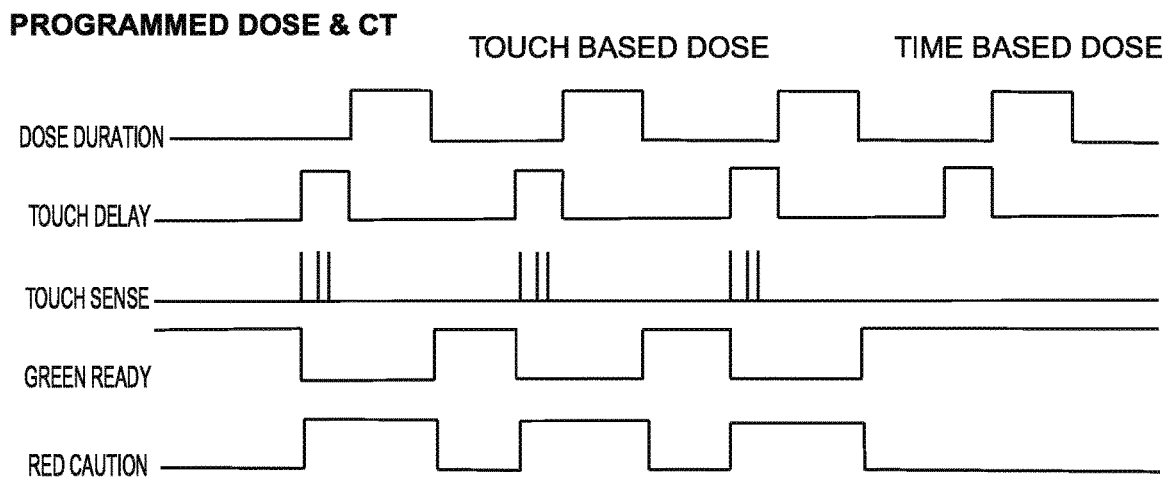
FIG. 15 illustrates the timing sequence of the disinfection cycle feedback.

It should be understood that the red/blue/green color feedback described above is merely exemplary. The number of different visual states and the colors used to designate the different states may vary from application to application. For example, FIG. 15 shows the timing sequence for a visual feedback language that involves two colors—green when the surface is disinfected and red when the surface is not disinfected. The Dose Duration line graph goes high when the UV source is on and goes low when the UV source is off. The Touch Sense line graph shows vertical lines each time a touch occurs. In this embodiment, the UV system implements a touch delay, which may prevent rapid and inefficient on and off cycle of the UV source. The delay is implemented by waiting a predetermined period of time after a touch has occurred before reengaging the UV source. The length of the touch delay may vary from application to application. The Touch Delay line graph goes high when a touch occurs and remains high until the touch delay has expired. The Green Ready line graphs goes high when the green visible light is illuminated and the Red Caution line graphs goes high when the red visible light is illuminated. In this example, the system begins in a disinfected state with the green visible light illuminated. When the first touch occurs, the green light is turned off and the red light is turned on. The red light remains on until the touch interaction (e.g. sequence of touches) has ended, the touch delay has passed and the UV source has completed a full UV disinfection cycle. Once the disinfection cycle is complete, the red visible light is turned off and the green visible light is turned on. The process repeats for additional touches. In some application, the UV disinfection system may be configured to periodically undergo a UV disinfection cycle even if no touch has occurred. This is shown in FIG. 15 in the area identified as Time Based Dose at the right end of the graph. In this application, the visible green light remains on during Time Base Dose, but that may vary from application to application. FIG. 15 shows an additional clean up cycle to assure additional dose based on protocol configuration, although this is optional it can be driven as a measure of additional prevention.

E. Social Media

In another aspect, the present invention may provide a UV disinfection network that is configured to collect data from social media and use that information to affect operation of one or more assets within the disinfection network. For example, social media content may be analyzed to identify content relevant to infections or the spread of infection and, upon identification of sufficient content, to direct one or more of the UV disinfection devices in the network to perform supplemental disinfection cycles, to increase UV source intensity and/or to increase UV disinfection cycle time. As noted above, FIG. 18 shows the social engine of one embodiment of this system. Patterns of use and training events can be programmed and this system can push training content and scores for learning and behavior modification. Various preprogrammed actions are configured and the ones that are not preprogrammed enable the user to better understand other tips and tails of the operational distributions and who is performing within these areas. This enables workflow testing and experimentation to better the disinfection process throughout. An example of this is tracking touch frequencies. As frequencies increase infections will increase. With this system and monitoring across the network we can initiate global cleanings by adding additional cleaning cycles. This can be driven by an actual outbreak, cold and flu seasons, employee sickness and many more social and actual data sets. It should be known that at any given time administration can send a command and the UV disinfection network can provide a "global" disinfection on demand or timed. As more information is captured and analyzed, the UV disinfection network will get better in tracking these data sets. During use in realtime, these precautionary or reactionary events will be initiated by ongoing trends and actual data that may be obtained by the UV disinfection network tracking capabilities or from external systems. It would seem like common sense to do an extra disinfection cycle after each infection is identified but this is not possible today without physically cleaning equipment and this process would augment the physical cleaning nicely.

Using web crawlers for regional news articles, Twitter firehose and Facebook API interfaces we can watch and search for terms relating to health, disease types (flu, cold season, out breaks etc.) and accumulate incident rates. When these events increase or elevate we can push additional health protocols forcing additional cleanings based on the severity and type of the recorded event. These can be suggested events or automated with specific preset protocols or timing. The timing is based on time of year where some of these are expected based on historical data. Severity of the response may be proportional to the severity of the outbreak and increase the time and frequency of cleaning.

F. Disinfection Network

Figure 19A:
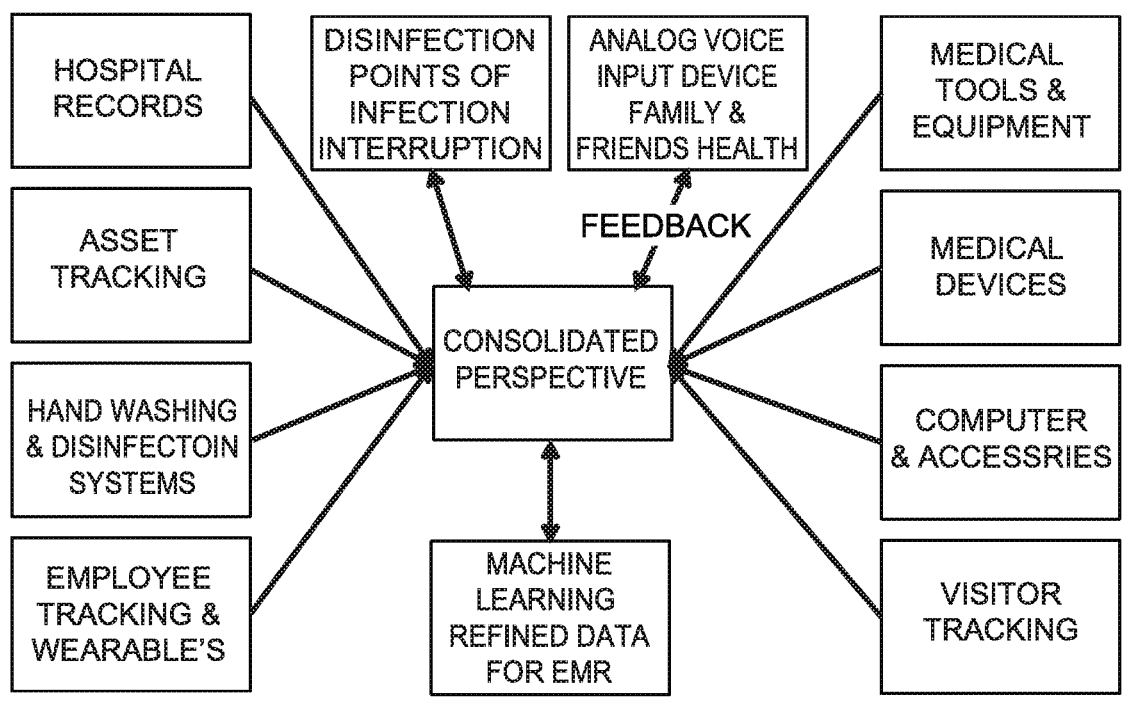
FIG. 19A shows a combination of the workflows for the disinfection process and system.

The UV disinfection network may be configured to collect essentially any data or information that might contribute to the networks ability to understand, track and disinfect against infections. This data may be collected by UV disinfection enabled devices or be obtained from sources outside the UV disinfection network. FIG. 19A shows some typical workflows that a UV disinfection network in accordance with the present invention might span to enhance the data and information about the infection process and probabilities. Opportunities to interface with existing asset management systems, nurse call and identification systems may enhance the process of disinfection and enable a better view of the infection probabilities. Enabling an overview of this information with machine business learning will enhance the understanding and may help to draw unexpected conclusions. An example of these interactions is shown below. FIG. 19B illustrates the type of data that might be collected from a room over a short duration. The data may be collected periodically and/or at interactions with each device. Each data record may include a time stamp field, a device ID field, a device type field, a status field, a life remaining field, a consumable type field, an associated room field and a patent ID field. This record format is merely exemplary and the system may be configured to collect and store essentially any data, including any data that might be relevant to or useful in tracking or analyzing enabled device, tagged individuals, infections and disinfection activity.

In an ideal world, each device will have a unique identifier that tracks touches and uploads that information into the cloud for analysis. The present invention may involve integration in essentially all hospital equipment and staff, like asset tracking for equipment, hand washing and teaching systems and other unexpected systems. The system may have an open API framework to import additional information for these systems in order to make a more complete record of touches and interactions. Each data set may provide status, ID, consumable percentage and function as seen above for association and comparison statistically. UTC time stamps allow universal alignment to time.

In one embodiment, the UV disinfection network may be configured to track UV exposure on an individual-by-individual basis. For example, the UV disinfection network may use individual ID tags to track movement of individuals through the network, for example, from room to room within a hospital, and to store data indicative of interactions between each user and a UV disinfection device. To illustrate, the UV disinfection network may use individual ID tags to identify a user that has come into proximity of a UV disinfection device during a UV disinfection cycle. For example, when a proximity sensor for a UV disinfection cycle is triggered, the individual triggering the sensor may be identified using the individual ID tag. Upon triggering of the proximity sensor, the UV disinfection system may terminate or interrupt the UV disinfection cycle (e.g. turn off the UV source) and a communication may be sent to the network server identifying the individual that triggered the proximity sensor. In the context of an RFID ID tag, the presence of an ID tag may be identified using an RFID reader integrated into or associated with the UV disinfection device. The communication regarding the individual triggering the proximity sensor may be sent by essentially any network devise, such as the UV disinfection device or the RFID reader. In some applications, the network server may combine a communication from the UV disinfection device and the RFID reader to track UV exposure by individual ID tag. Upon a determination of the individual triggering the proximity sensor, the UV disinfection device may send a communication identifying UV source intensity and the amount of time it took for the UV source to be turned off. In some applications, the UV disinfection device may measure the actual time required to turn off the UV source. In other applications, that time may be an estimate (e.g. based on average turn-off time, plus a safety margin, if desired). The UV disinfection network may maintain accumulated UV exposure data for each individual and use that information to affect operation of UV disinfection devices or other assets within the network. For example, the network may maintain data representative of the accumulated UV-C exposure taking into account UV source intensity and UV source turn-off time for each exposure event. This information may be accumulated and watched to ensure that no individual is exposed to more than a desired amount of UV energy in a given timeframe (e.g. no more than predetermined amount of UV-C energy in a 24 hour period). In some applications, the network may collect individual event exposure data and maintain accumulated exposure data by individual to facilitate confirmation of compliance with exposure limits. In some applications, the network may take action to help prevent overexposure. For example, if an individual approaching the periodic exposure limit (e.g. daily exposure limit) enters a room, the network may instruct the assets to vary operation to protect the individual from further exposure. For example, when an individual ID tag enters a room, the ID tag reader may send a communication to the server providing notice that the user has entered the room. The network server may then evaluate accumulated exposure for that individual and determine whether action is desired to protect the user from further exposure. If so, the network server may instruct the UV disinfection devices or other assets in that room to take any desired action. With regard to UV disinfection devices, this may include reducing UV intensity, reducing UV cycle time, terminating any UV disinfection cycle in process and/or preventing start of any UV disinfection cycles while that individual remains in the room.

G. Integrated UV Disinfection System

Figure 20:
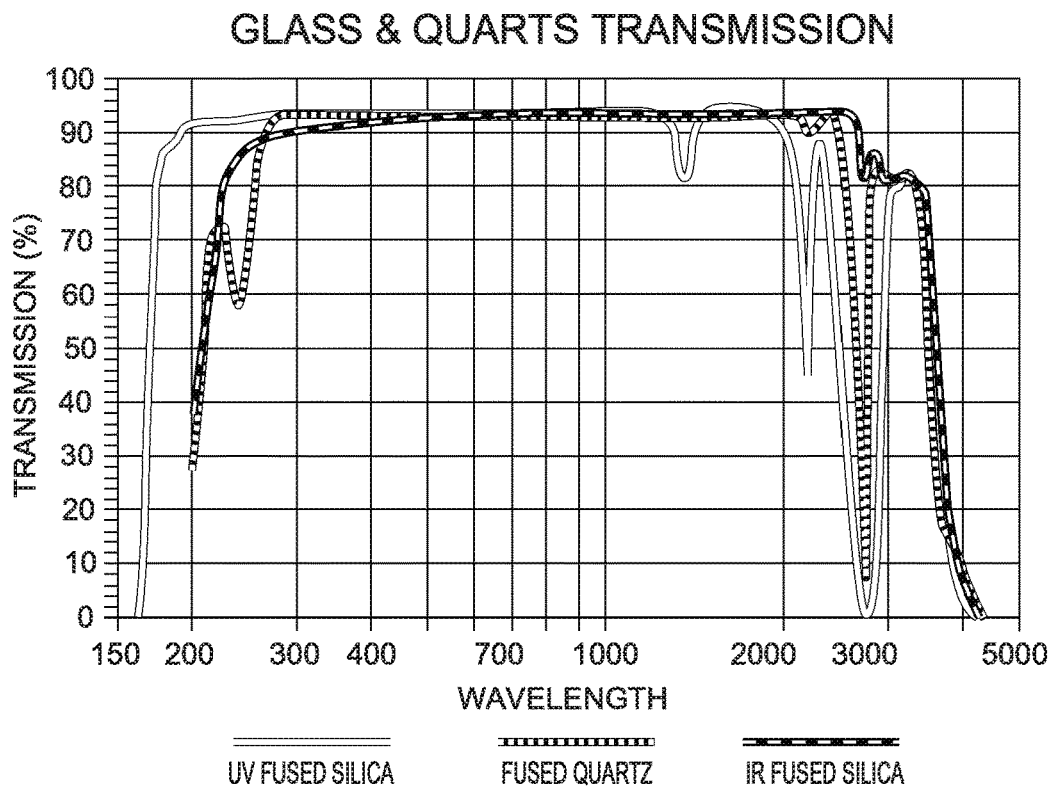
FIG. 20 shows the transmission of UV-C 254 nm through quartz.
Figure 21:
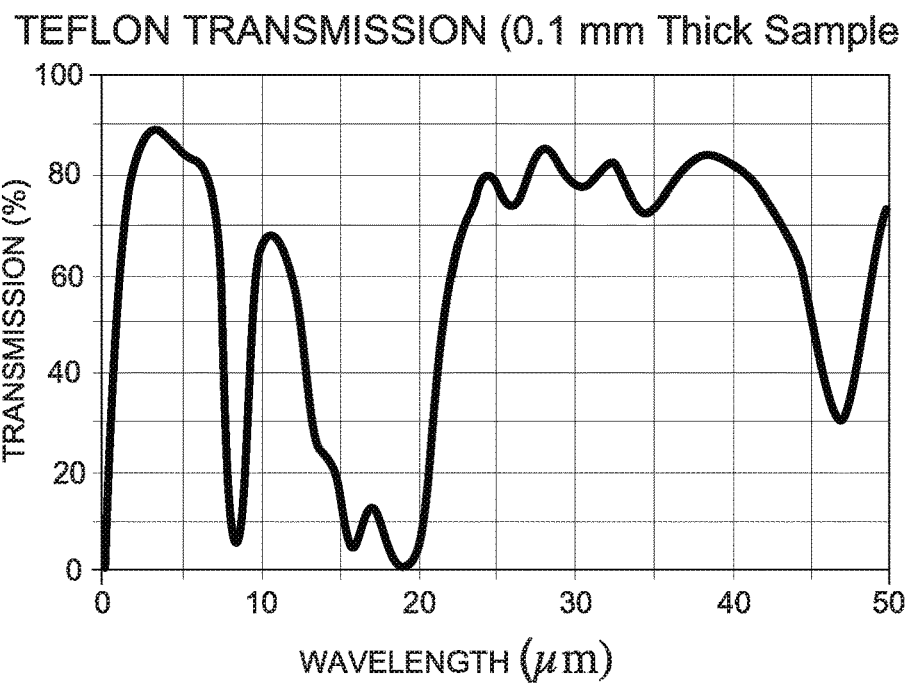
FIG. 21 shows the UV-C transmission through Teflon through a 1 mm thick layer.
Figure 22:
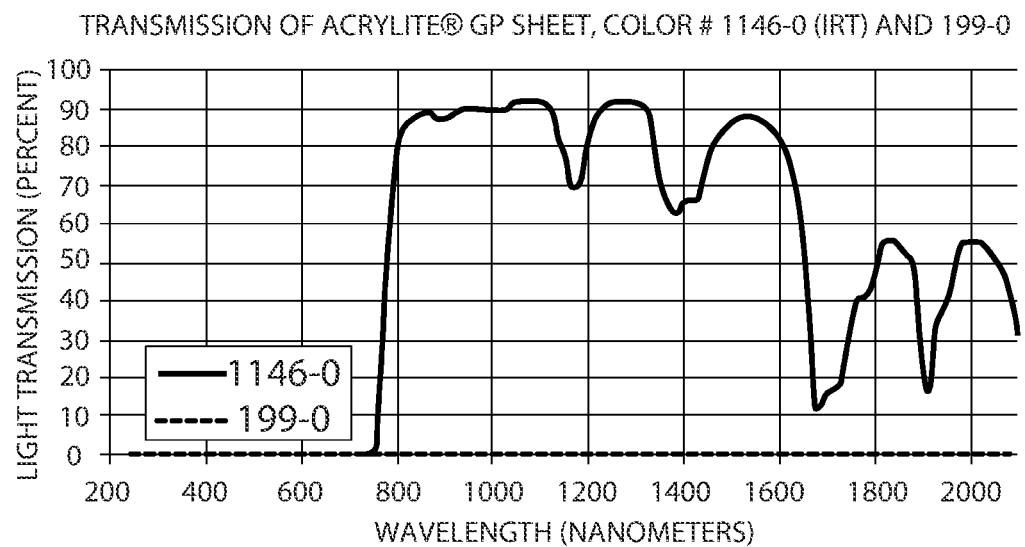
FIG. 22 shows that UV-C 254 will not have transmission through common clear plastics.

In another aspect, the present invention provides a UV disinfection system that can be incorporated directly into a devices to provide UV disinfection for the device from within. To facilitate these types of constructions, the devices to be treated may incorporate UV transmissive materials at the touch surfaces to direct UV-C energy generated inside the device to pass outwardly to the touch surfaces. FIGS. 20 through 22 show the UV-C transmission properties of various materials. UV-C typically includes light in the wavelength range of 100 nm to 290 nm. In embodiments of the present invention, the UV light source may be configured to produce UV light at a wavelength of about 254 nm. Materials with good UV-C transmission properties at 254 nm allow the UV-C 254 nm disinfection system to be built internally within products rather than externally by allowing surface materials to radiate UV-C. In one embodiment, the present invention utilizes a UV-C transmissive material having a transmission percentage of at least 60 percent at 254 nm. In another embodiment, the UV transmissive material of the present invention has a transmission percentage of at least 65 percent at 254 nm. In yet another embodiment, the UV transmissive material has a transmission percentage of at least 70 percent or at least about 72 percent. As shown, UV fused silica, fused quartz and PFA provide adequate UV-C transmission at 254 nm. Many typical materials, such as Acrylite material shown in FIG. 22, do not pass sufficient UV-C to be suitable for typical applications.

Figure 32:
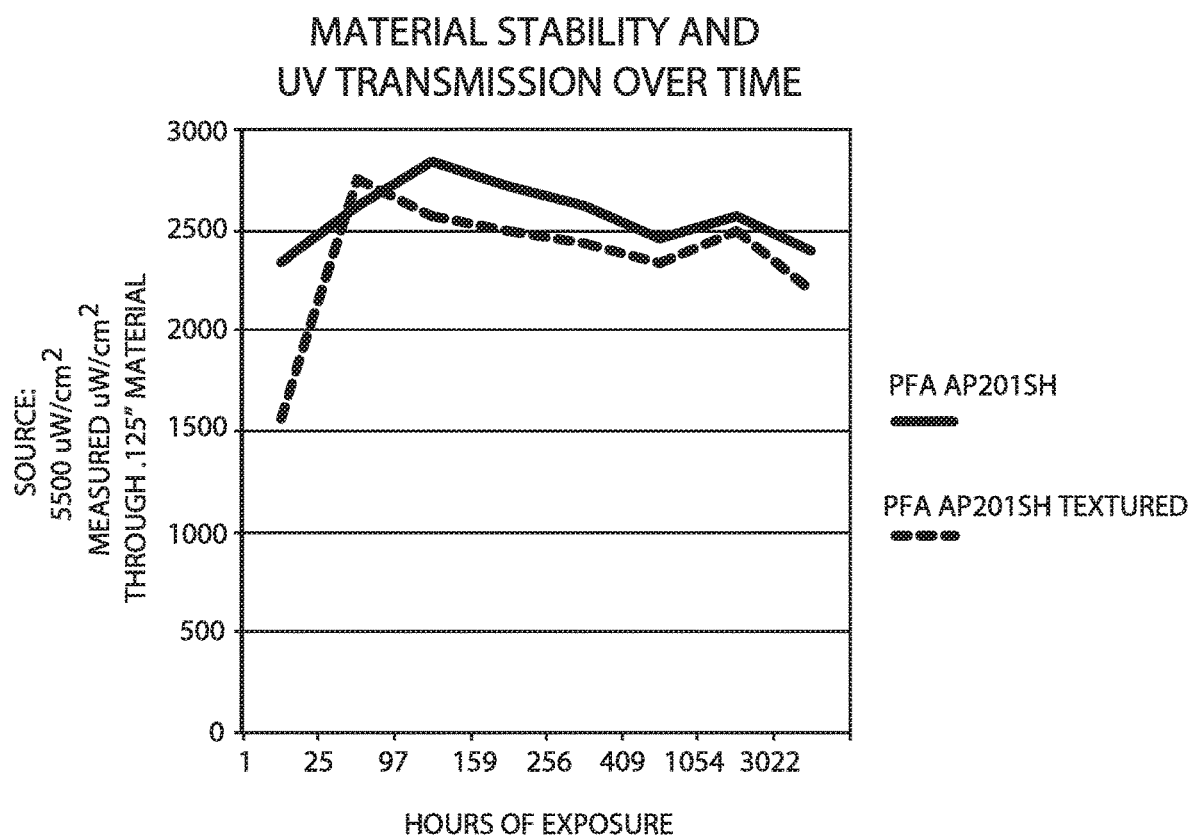
FIG. 32 shows a comparison of transmission over exposure to UV-C at a given dose of 5500 uW/cm2. It is clear that the PFA material was more stable and had a better transmission percentage.

Optically, the use of texture on the source side provides a better piping and performance by creating multiple light paths. The substrate may include have a structural thickness for strength and reduced the thickness to provide better UV transfer will less losses. Thickness is directly proportional to UV-C losses with materials with lower transmissivity. In one embodiment, the substrate has structural ribs where needed to make the PFA a viable "A surface" part. Because the substrate is semi-transparent, the substrate material enables customization using an RGB LED to select any color the user wants and also using these color for connection status, battery life, click status, and other feedback. As noted above, PFA provide UV transmissive characteristics that are suitable for use with the present invention. FIG. 32 shows the transmission characteristics of PFA material with intensity on the vertical axis and time on the horizontal axis. The graph shows the transmission and stability of the material (both textured and un-textured). With quartz, Teflon and PFA materials it may be desirable to diffuse the UV light moving out through the material. This can be done on the top or bottom side of the material. Providing scratches, a gradient of prism like surfaces or a simple texture, the system can extract light from the material. Without this modification of the material, light will have a tendency to exit in the directed pattern. An example of this is, when projected through a material, the texturing diffuses the light. To illustrate, when edge light is projected into a piece of quartz, there is great edge to edge transmission but little surface emission. If the quartz is textured or there is a reflector with UV reflectivity, good transmission is achieved. In some applications, the substrate may include textures for indirect source pick up and polished surface for direct source areas. Texturing and polishing a substrate using a flaming process may provide enhanced performance.

Figure 23:
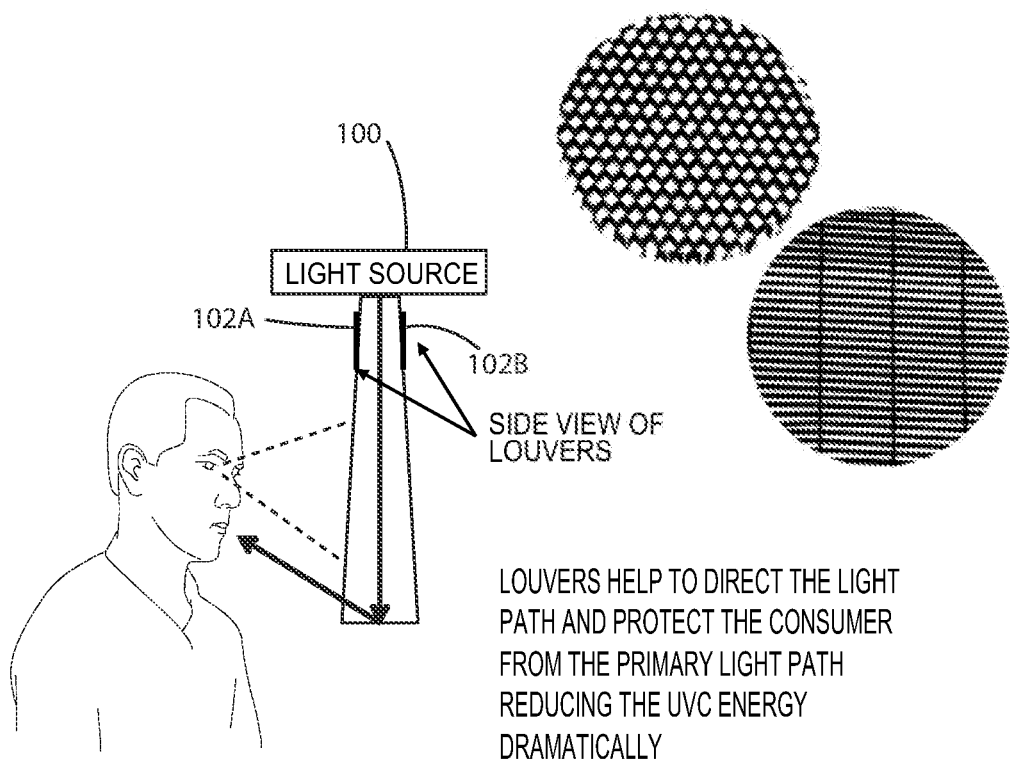
FIG. 23 shows that by using louvers and honeycomb substrates we can limit user exposure of UV-C light in a disinfection control device.

FIG. 23 shows a device with UV light source 100 that is enhanced by louvers 102a-b. The UV-C energy drops off fast over transmission distance and extending the transmission path increases energy loss within the transmission media and results in less UV-C energy reaching a proximate individual. The reduction of UV intensity is dictated by the inverse squared law and is reduced dramatically allowing more dose with less exposure. By using louvers 102a-b, we can increase the distance the UV light needs to travel to get to your eyes in a given application. In the illustrated embodiment, the louvers 102a-b direct the UV-C light to an opposing surface and only the reflection can be seen. As a result, louvers 102a-b help to limit exposure to low dose UV-C. Additionally, louvers 102a-b cause the UV-C energy to travel through the transmission media for a greater distance, thereby providing the opportunity for more energy to be transmitted over the touch surface. Although FIG. 23 shows louvers 102a-b disposed on opposite sides of the UV-C source to direct light through the UV transmissive material, additional or alternative louvers may be added to the system to provide supplemental UV-C light guidance. For example, louvers (not shown) may be added to the inside and outside of the UV transmissive material at the end of the material opposite the UV-C source to assist in redirecting UV-C light that reflects off the far end of the UV transmissive material. The louvers 102a-b may be manufactured from essentially any material that is not transparent to UV-C energy. For example, the louvers may be manufactured from a UV-C reflective metal, a plastic material that is reflective or substantially opaque to UV-C light or a plastic material that is lined with a layer of UV-C reflective or UV-C opaque material.

H. Reflective Substrates

Figure 24:
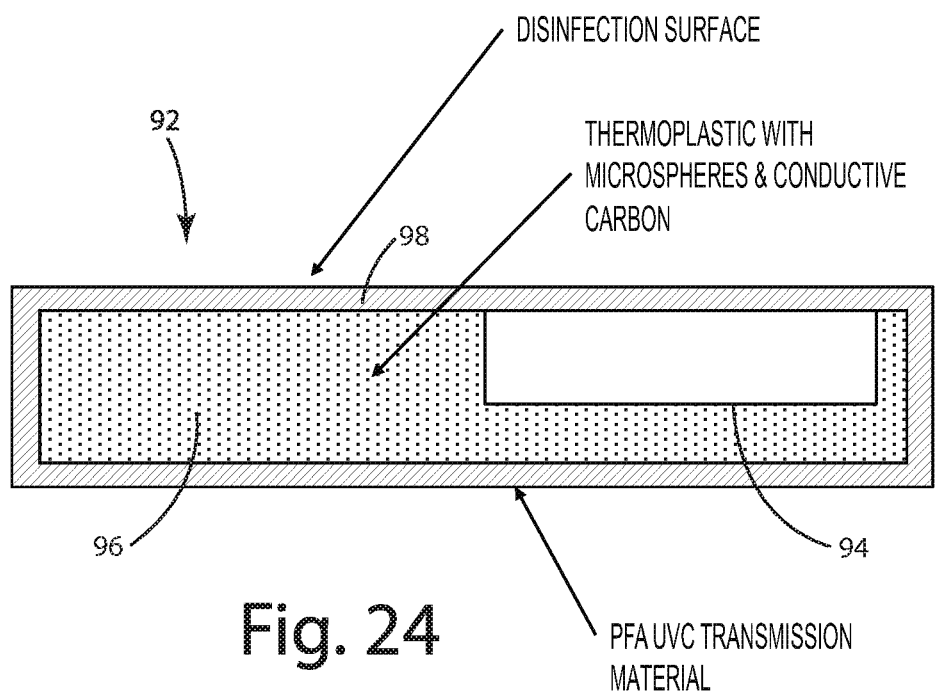
FIG. 24 shows a device made of thermoplastic with metal particles for reflection and an outer layer of Teflon for light piping the UV-C light around that molded device.

In another aspect, the present invention provides an improved device construction utilizing UV reflective materials. In one embodiment, the present invention may include thermoplastics with enhanced reflectivity to UV-C light. FIG. 24 is a cross-sectional illustration showing how thermoplastic materials can be used as reflectors in UV disinfection systems. Flow cells that contain e-PTFE (expanded PolyTetraFluor Ethylen) provide 95% reflectance or more (as shown in the table below) of the UV-C light-making systems constructed of these materials highly transmissive.

| Material | Reflectivity |
| --- | --- |
| e-PTFE | 95% |
| Aluminum-sputtered on glass | 80% |
| Aluminum foil | 73% |
| Stainless steel (various formulas) | 20-28% |

In this embodiment, a device 92 generally includes a disinfection control system 94, a thermoplastic substrate 96 and a UV-C transmissive outer layer 98. The disinfection system may include a UV-C source and a disinfection control system that polished aluminum and chrome metal are good reflectors, but thermoplastics can also use thermoplastic. Thermoplastic compositions that reflect ultraviolet radiation are another source of disinfection efficiencies. In one embodiment, the UV reflectivity of a thermoplastic material may be improved by mixing a thermoplastic compositions including of a suitable thermoplastic material and particles of UV reflective material.

The composition and configuration of the thermoplastic composition and the UV reflective material can be selected to provide a composition with desired levels of UV reflectivity, and transmissivity for a desired application. The composition of the thermoplastic composition may also be selected to be cost-effective, resistant to degradation upon exposure to UV radiation for at least a desired period of time. Utilizing PFA and e-PTFE is a great example of a reflector and UV-C transmissive material.

The level of UV reflectivity is adequate to provide a desired intensity of reflected UV radiation within a surface sample, such as a sample of a surface. For example, a desired intensity of reflected UV radiation from a thermoplastic composition may provide a germicidal intensity of UV light adequate to decontaminate a surface sample, such as 20 to about 40 milliwatt-seconds/cm2, including 20, 25, 30, 35 and 40 milliwatt-seconds/cm2, and any light intensities there between. The desired level of reflectivity of a UV reflective thermoplastic composition can vary depending on the configuration of a reflecting surface that includes the UV reflective thermoplastic composition. UV reflective thermoplastic compositions may be characterized by an initial reflectivity of at least 30% of UV radiation at a wavelength of 254 nm upon initial contact with UV radiation. Other UV reflective thermoplastic compositions are characterized by an initial reflectivity of at least 31%, 32%, 33%, 34%, 35%, 36%, 37%, 38%, 39%, 40%, or more, of UV radiation. The UV reflectance can be measured using a UV spectrophotometer, such as a Cary 500 UVNIS/NIR Spectrophotometer equipped with a DRA-CA-5500 Integrating Sphere, or comparable instrumentation. A thermoplastic composition in one embodiment may maintain an initial reflectivity of at least 30% of UV radiation at a wavelength of 254 nm for a suitable period of time, which may be at least 10 hours of continuous or intermittent UV radiation, and may in some embodiments be up to 20, 30, 40 hours or more of continuous or intermittent UV radiation.

The UV reflective material is selected and configured to provide a thermoplastic composition having desired level of UV reflectivity and a desired level of resistance to UV degradation. The thermoplastic composition may be a metal-polymer composite comprising UV reflective metal microparticles dispersed in a thermoplastic polymer resin. The UV reflective material may be aluminum, although any suitable UV reflective materials can be used. Suitable UV reflective materials can include metal or metal alloys, such as stainless steel particles, or non-metal materials such as UV reflective polymer materials. The UV reflective material may be configured as particles within the thermoplastic material. The size and density of the particles in the thermoplastic composition can be selected to provide desired levels of UV reflectivity, machine processability, and cost-effectiveness. The particles of UV reflective material can have any size suitable to provide the desired level of UV reflectivity, but in one embodiment are microparticles, such as microparticles having an average size of about 1 to 100 µm, or in some embodiments about 15 µm to about 55 µm, including particles having an average size of about 15, 17, 20, 25, 30, 35, 40, 45, 50, 54 or 55 µm.

Any density of particles of UV reflective material can be included in a thermoplastic material that provides a thermoplastic composition with a desired level of UV reflectivity. The density of particles of UV reflective materials may, in some embodiments, be high enough to provide a desired level the UV reflectivity to a thermoplastic composition, without undesirably affecting the machine processibility of a thermoplastic composition. For example, concentrations of abrasive UV reflective materials, such as metallic UV reflective metals, of about 5% or more may cause damage to machining surfaces. Therefore, the density of metallic UV reflective materials in the thermoplastic composition may, in some embodiments, be less than about 5%, 4%, 3% or 2%. To provide adequate levels of UV reflectivity, the density of metallic UV reflective material may, in some embodiments, be at least about 0.25%, 0.50%, 0.75%, 1.00%, 1.25%, or 1.50%. Examples of suitable densities of UV reflective materials include about 1.00%, 1.25%, 1.50%, 1.75% and 2.00%

Various UV reflective compositions having desired levels of UV reflectivity can be formulated using combinations of UV reflective microparticles of different sizes and concentrations. Larger particles and/or higher concentrations of UV reflective material can provide higher levels of UV reflectivity; smaller particles and lower concentrations of UV reflective material can provide lower levels of UV reflectivity. An increase in the surface area to volume ratio of the UV reflective material may account, at least in part, for the increased UV reflectance of the smaller particles. For example, a thermoplastic composition comprising 1.00% aluminum microparticles having an average size of 17 µm in a polypropylene homopolymer thermoplastic material may have a reflectivity of up to about 40%, or higher, of UV radiation at a wavelength of 254 nm. Comparably, a thermoplastic composition comprising 1.50% aluminum microparticles having an average size of 54 µm in a polypropylene homopolymer thermoplastic material may also have a reflectivity of up to about 40%, or higher, of UV radiation at a wavelength of 254 nm. In some embodiments, UV reflective compositions has a UV reflectance at 254 nm of at least about 30%.

The low dose UV-C disinfection applications are identified in FIGS. 3-6, 10-14, 23-31 and 33-41.

The capacitive surface is best as metal mesh like a screen allowing light through while providing a capacitive substrate, metal strips or stampings can also be used for specific coverage areas.

I. Exemplary UV Disinfection Devices

In FIG. 25, an embodiment of a membrane keyboard with low dose UV-C is shown. In this embodiment, the membrane keyboard 110 generally includes a membrane substrate 112, a switch layer 114, a tactile layer 116, a UV transmission layer 118 and a disinfection system 120 with a UV light source 122 and a disinfection control system 124. In this embodiment, the UV transmission layer 118 is manufactured from PFA. By using PFA as the surface transmission layer and light piping the UV-C through that transmission layer the disinfection system provides a good dose of UV light to the touch surface. Although the UV transmission layer 118 of this embodiment is PFA, the UV transmission layer 118 may be manufactured from essentially any material capable of providing the desired level of UV-C transmission. The switch layer 114 includes keys that are used for touch sensing. The switch layer 114 may be essentially any current or future keyboard switch layer. The disinfection control system 124 enables the low dose UV-C method. The tactile layer 116 of this embodiment has the printing of the keys and may also use reflective nanoparticle Aluminum or Titanium Dioxide to reflect the UV to the outer surface of the UV transmission layer 118. In this embodiment, the nanoparticle coating protects the surface from UV-C degradation like an SPF for materials and is reflective to UV-C providing a better surface dose. The tactile layer 116 of this embodiment may provide for physical movement causing tactile feedback. The tactile feedback can also be accommodated by using vibration motors to initiate haptic feedback using vibration, but the physical click in a key may also be accommodated with a spring dome used in membrane keypads. In the illustrated membrane construction, each layer is glued together, although the final UV transmission layer 118 is held by a pressure bezel in this embodiment. Glues may be used that do not change the optics and ones that are not unacceptably susceptible to UV degradation. For example, the components may be joined by an index-matching cement or adhesive. The transmission area may have bulbous and rounded optics on the edges to accept and pipe the UV light from the source into the surface materials.

Figure 26:
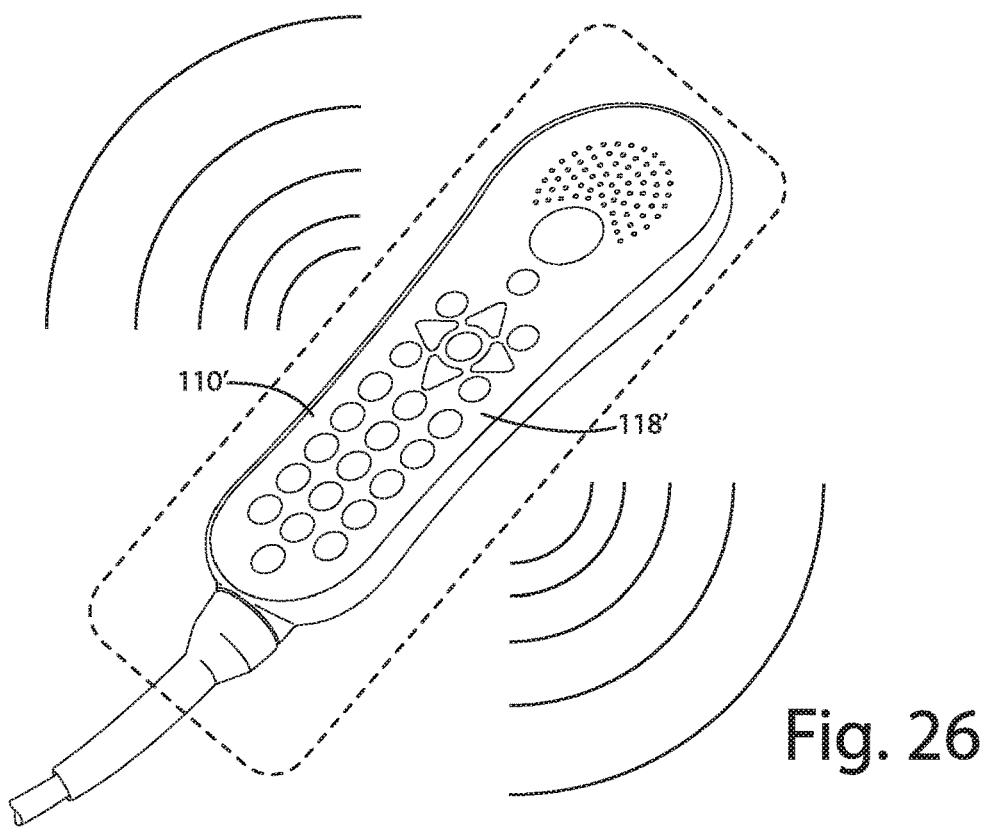
FIG. 26 shows the same keyboard used for a remote control keyboard enabling remote controls with surface disinfection.

The keyboard of FIG. 25 may be integrated into a wide variety of applications and may be customized to provide optimized performance for each application. For example, the keyboard may vary in the design, configuration, number, location and arrangement of keys, as well as the integration of other user interface components, such as a display screen. For example, FIG. 26 shows a keyboard 110' having the general construction of FIG. 25 incorporated into a bedside remote control. In this embodiment, the keyboard 110' is overlaid with a UV transmission layer 118' that may cover the entire remote control (e.g. front, sides and back) or only a portion of the remote control (e.g. front only).

Figure 27:
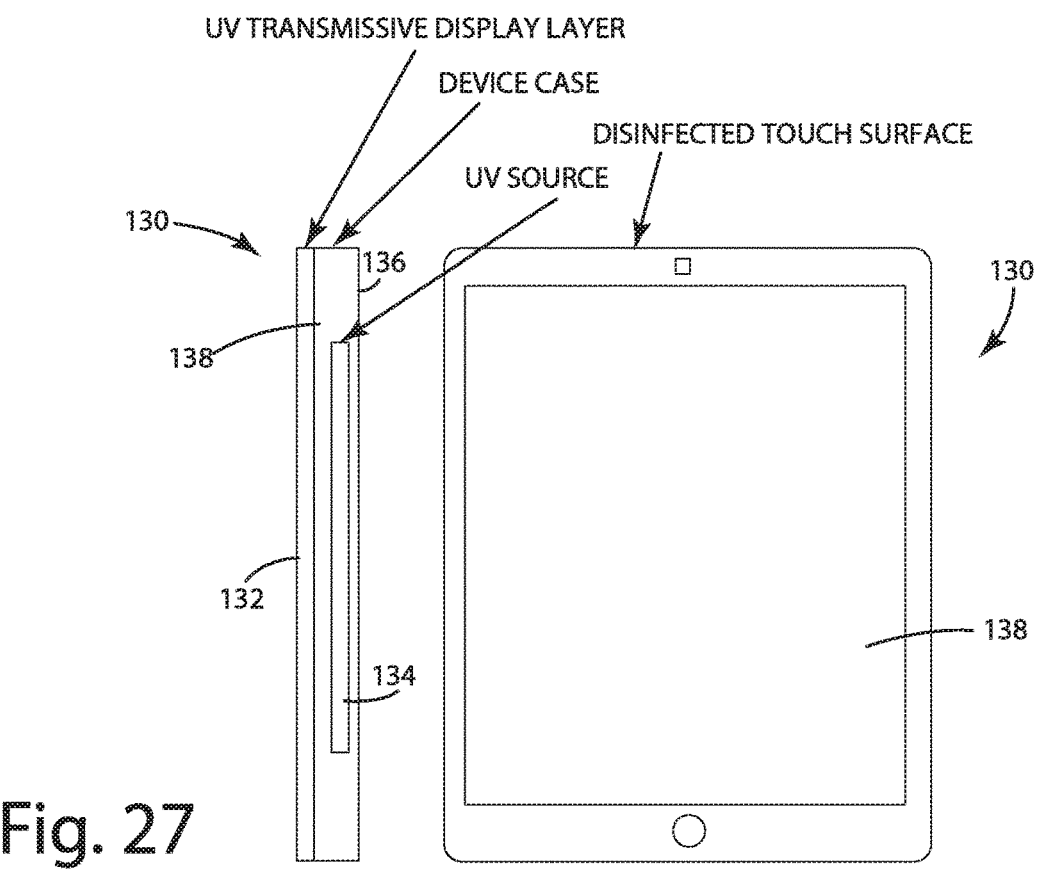
FIG. 27 shows a tough keyboard where the surface disinfection is built into the display wherein the display has a quartz UV-C transmission material for surface disinfection.

In another aspect, the present invention may provide low dose UV-C disinfection in touch screens. For example, FIG. 27 shows a tablet computer 130, such as an iPad, with an integrated UV disinfection system. In FIG. 27, a quartz transmissive layer 132 is used to enable low dose UV-C in a touch display on a tablet computer, such as an iPad. As noted above, quartz is a good transmission substrate for UV-C 254 nm. In FIG. 27, the tablet computer may include a disinfection system having a control system (not shown) and UV light source 134 disposed in a device case 136 combined with a UV transmissive display layer 132 that covers the touch screen 138. Although shown in the context of a tablet computer 130, the present invention may be incorporated into essentially any device with a touch screen, such as monitors, mobile phones and other designs. The PFA material can be used for the connecting and bottom surfaces to enable all surfaces with low dose UV-C. In some applications, the quartz layer (or other UV transmissive layer) may be coated with a UV reflective material to increase the amount of UV-C light that reaches the touch surface and to help prevent UV light from penetrating into the underlying components. As an alternative to a UV reflective coating, a UV reflective sheet may be disposed beneath the UV transmissive layer. E-PTFE is a great coating and can be extruded in sheet or films, spray coated, co-molded, or and is transparent to light but reflective to UV-C. Thinner quartz is less expensive but is more difficult to transfer effective UV-C doses. The edges of the quartz are highly polished and the UV-C source has a reflector that is specifically design to provide the directing optics that provide the best intensities. This means the light needs to go around the lamp where possible as opposed to reflecting the UV light back through the lamps and seeing reduced performance due to the quartz surfaces. In some cases the thickness of the quartz allows the end to be rolled allowing a very nice piping entry for the source. The end of the quartz screen cover or surface is bent to allow the source to have more surface area exposure to the entry point for the light pipe.

Figure 28:
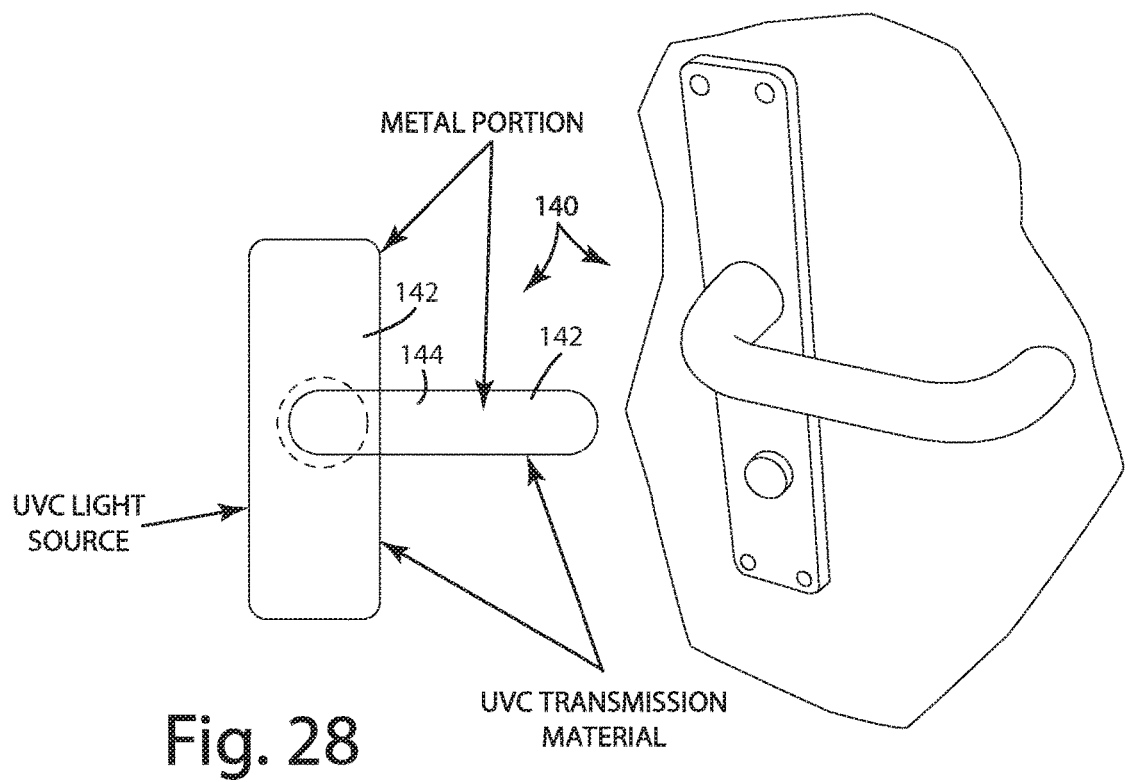
FIG. 28 shows how the disinfection control system would be incorporated into a door knob.

The present invention may be adapted for use in adding an integrated UV disinfection system to a broad range of products. For example, the construction may allow essentially any product that is the subject of frequently touches to be provided with an integrated, internal UV disinfection system. To illustrated, FIG. 28 shows a door handle 140 that has an over layer 142 of PFA and is controlled by the disinfection control system (not shown). In this embodiment, the outer layer 142 is disposed over an underlying metal substrate 144. The metal substrate 144 makes a great surface for the capacitive sensor. In the context of the door handle, it may be desirable to power the disinfection control system using a wireless power supply. For example, the disinfection control system shown in FIG. 5 can be used for the door handle 140 and other devices where wireless power may be beneficial. In the context of the door handle 140, the wireless power system is extended to the door frame and power for the device mounted in the door and power is provided through that wireless connection. More specifically, a primary coil or other wireless power transmitter is mounted in the door frame and a secondary coil or other wireless power receiver is mounted in the door adjacent to the primary coil in the door frame. The wireless power supply may be connected to mains power and may include a wireless power controller that applies the appropriate power signal to the primary coil to generate an electromagnetic field capable of wirelessly conveying power to the secondary coil in the door. With this construction, the power is connected to the mains while the disinfection system remains mobile with no connections. A local battery is optional but allows for better dose control, feedback and behavior functionality. If desired, this system may utilize the same disinfection control system and report touches in the same manor using UTC time and touch accumulators. Because touches and infections are a transfer function these frequencies are a product of statistical probabilities and enable helpful inputs to scoring and global decisions. All behavior feedback and indicators could be the same for consistency. However, they could vary, if desired.

Figure 29:
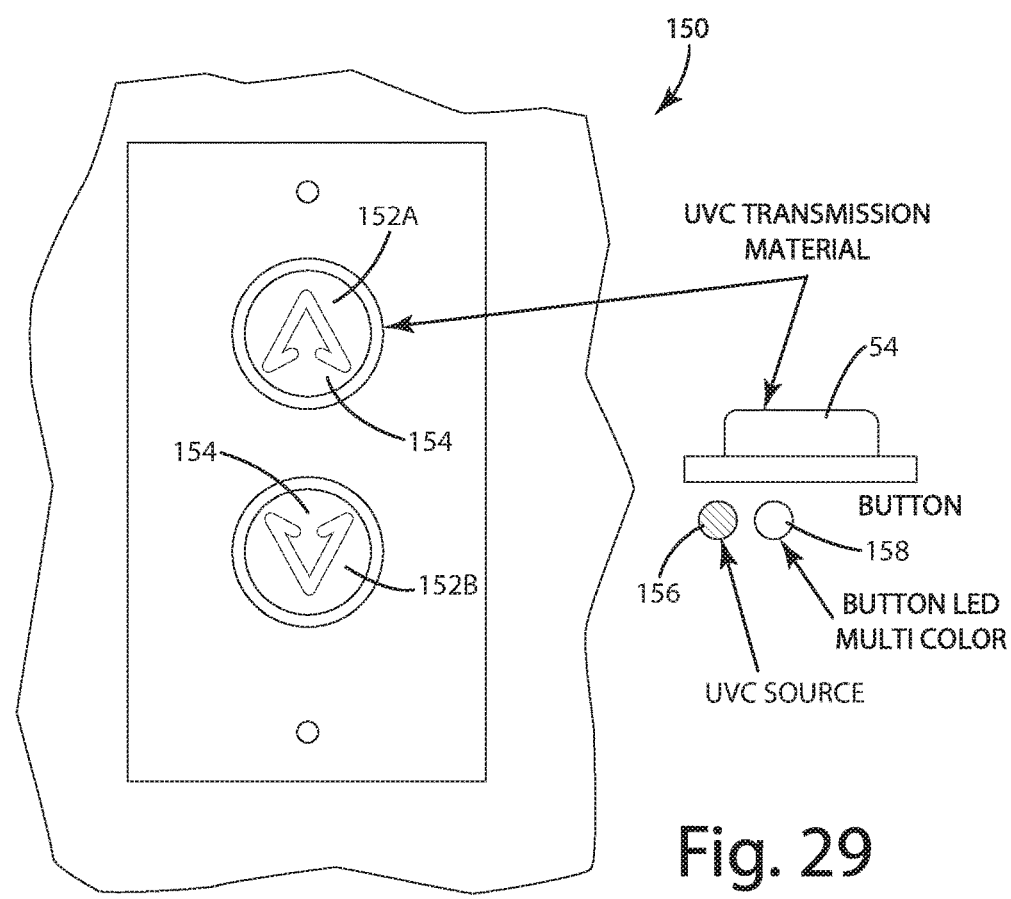
FIG. 29 shows an elevator button with UV-C transmission and with the disinfection language.

In FIG. 29, UV transmissive material, such as PFA, in used in the elevator buttons and enable the same low dose UV-C solution with disinfection status described above. In this embodiment, the elevator control panel 150 includes two button assemblies 152a and 152b. Each button assembly 152a-b may have a UV transmissive cover 154 disposed over an underlying UV-C source 156. Additionally, a multicolor LED 158 may be situated under each button to allow the button cover 154 to be illuminated with the color associated with the disinfection language discussed above. The control system is designed to turn off at touch, wait for a short period indicating an average touch and then turn on the UV to treat the button.

Figure 30:
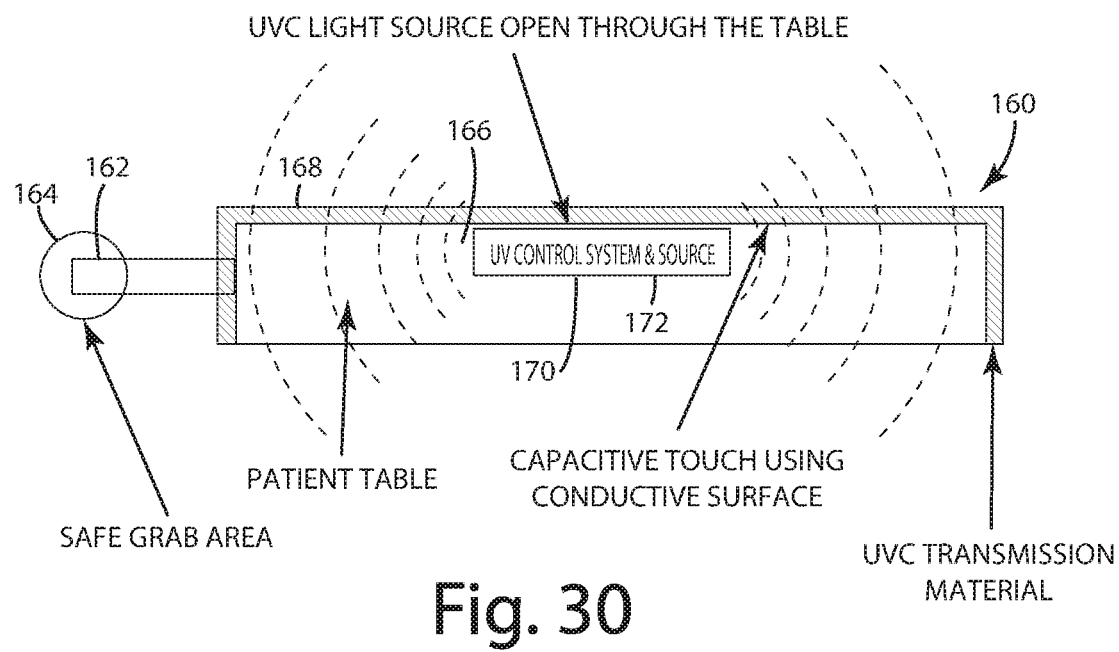
FIG. 30 shows a cart with a grab handle that is enabled with a disinfection control system that protects the grab area and teaches where a safe handling zone is and when to use it.

FIG. 30 shows a table 160 with grab bars 162 and a UV transmissive surface 164, such as PFA. It should be noted that PFA is already used in medical applications and is known for its chemical resistant properties. As shown, the table 160 has a patient support surface 166 that is covered with a PFA UV transmissive layer 168 and grab bars 162 that are covered with PFA UV transmissive layers 164 to enable proper use and handling. The systems also include the disinfection control system 170 and UV light source 172 that are enclosed within the table 160. The disinfection control system 170 may implement any of the various UV treatment and touch tracking processes discussed elsewhere in this disclosure.

Figure 31:
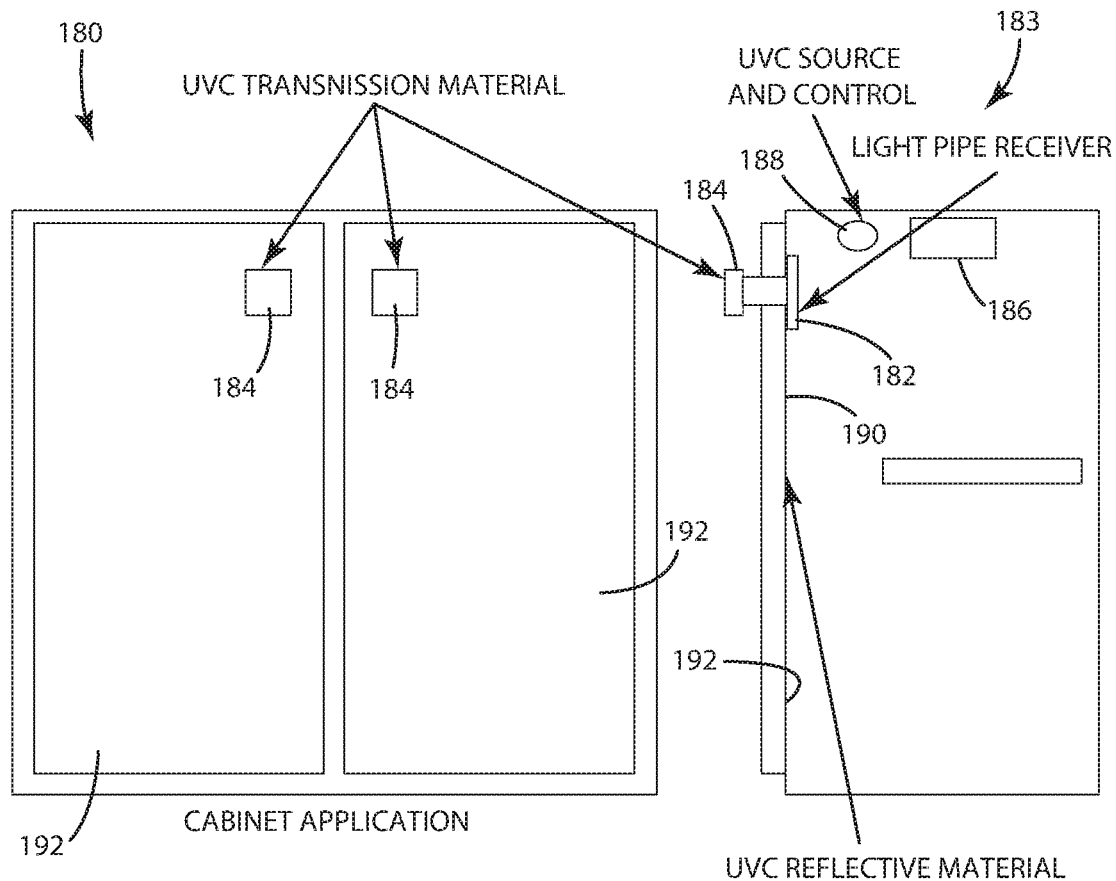
FIG. 31 shows the use of a disinfection control system in a cabinet with UV-C transmission door pulls that light-pipe the UV-C light to enable the door pulls to be disinfected.

Experience has revealed that there can be issues with storage cabinets as they are accessed and may not have required washing or gloving for the user. FIG. 31 shows storage cabinet 180 incorporating an embodiment of the present invention in which an internal UV-C disinfection system 182 light pipes the UV-C to the outside door pull 184. In this embodiment, a small amount of metallic reflector material is used as the capacitive surface indicating touch and enabling the low dose UV-C system. An aluminum reflector can be used behind the material and a progressive and/or textured light pipe like molded surface. The UV disinfection system 183 may include a control system 186 and a UV-C source 188. The door pull 184 may be manufactured from a UV-C transmissive material that allows UV-C light generated inside the cabinet 180 by the UV-C source 188 to be routed to the exposed outer surfaces of the door pull 184 so that the outer surfaces of the door pull 184 can be properly disinfected. A UV reflective layer 190 may line the interior of the doors 192 to reflect the UV-C light back into the storage cabinet to allow disinfection of the interior of the cabinet 180.

Figure 33:
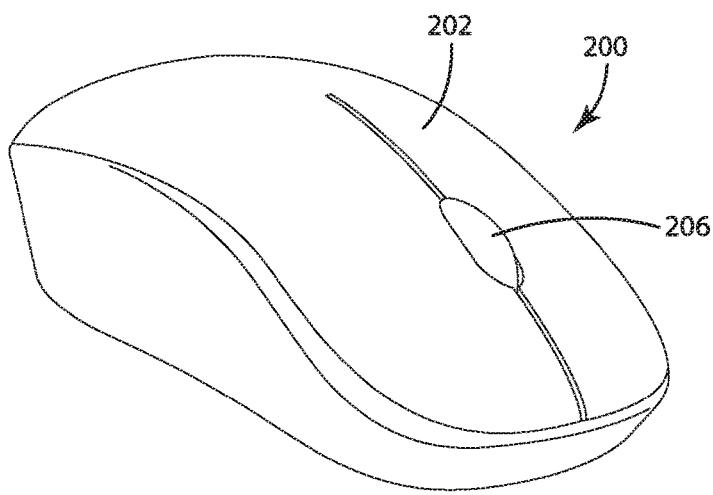
FIG. 33 shows a design of a mouse wherein the plastic parts are molded in PFA allowing UV-C transmission to the surfaces of the mouse.
Figure 34:
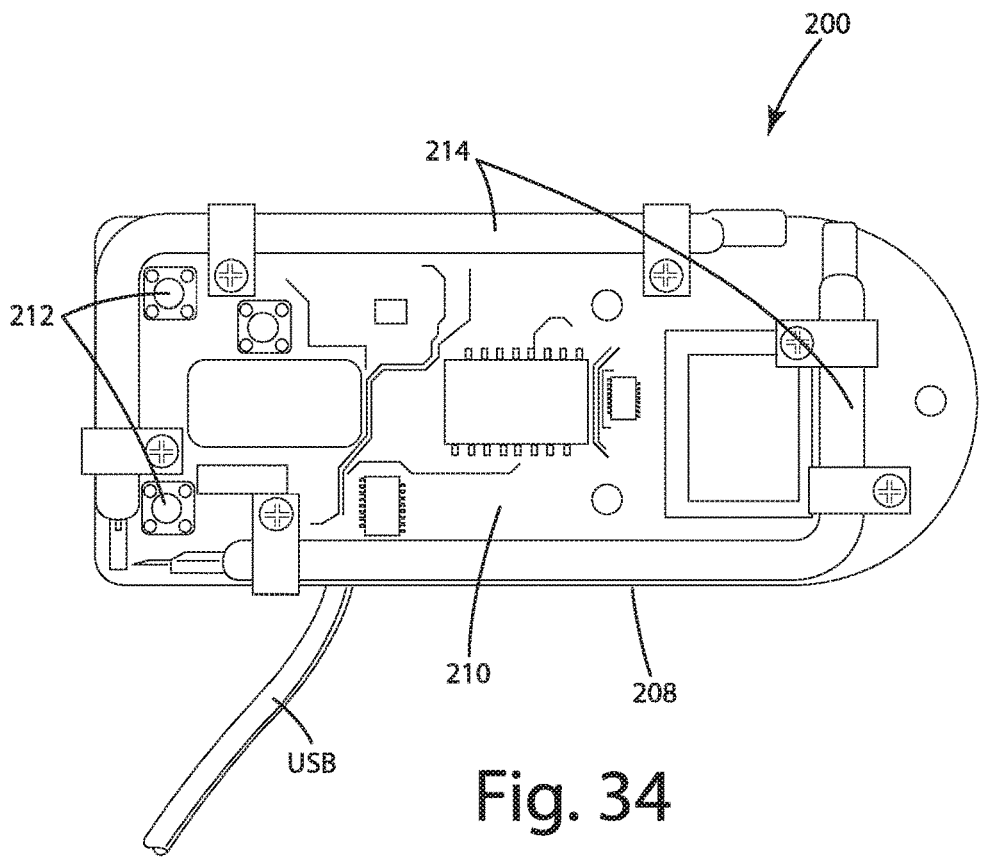
FIG. 34 shows an example of the mouse circuit board and lamp driver wherein the UV-C source is substantially located along the surfaces of the device to be disinfected. The roller is also molded in PFA to enable UV-C transmission and is properly disinfected.
Figure 35:
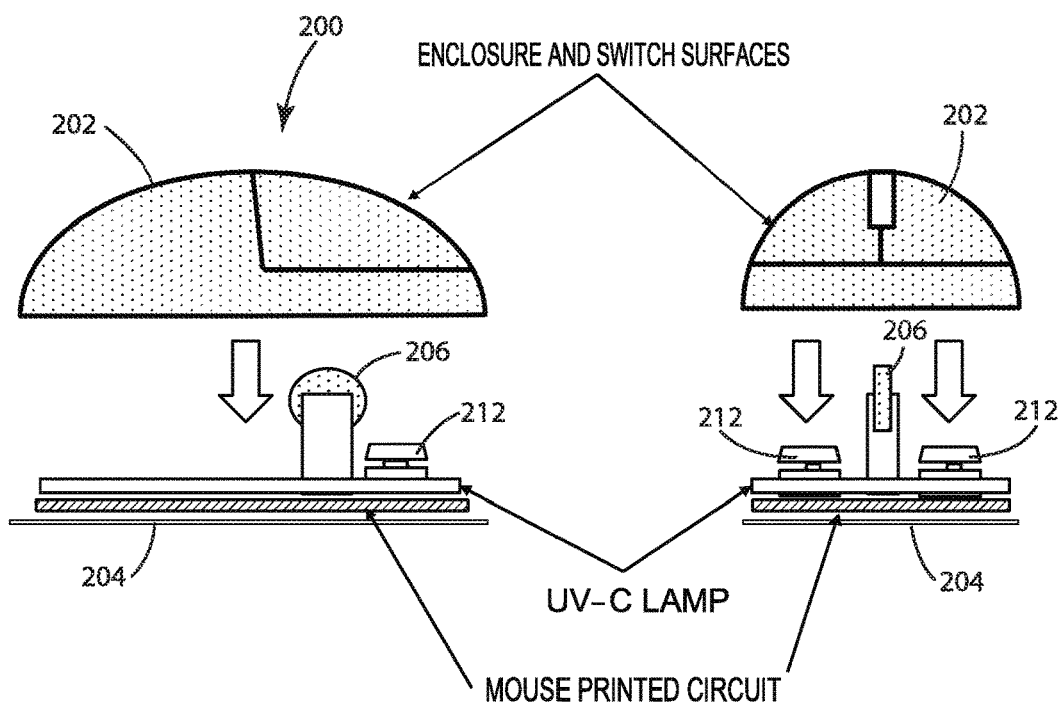
FIG. 35 shows the assembly construction of a disinfection-enabled mouse. The upper housing is a one piece molded construction with a living hinge on both the left and right click buttons. The UV-C source is designed to traverse the whole inner PCBA. This provides enough dose to provide suitable disinfection. When the upper housing and lower housing sandwiches the PCBA with the UV-C source is makes a solid disinfection device. The disinfection control system is then implemented within the mouse control microprocessor to help reduce cost and simplify the design even further.

FIGS. 33-35 are illustrations of a mouse 200 designed to be manufactured at least in part from a UV transmissive material, such as PFA. The mouse 200 of the illustrated embodiment includes a top housing 202 and a bottom housing 204 that cooperatively form the outermost structure of the mouse 200. The top and bottom housings 202, 204 may be molded from PFA or other UV transmissive materials. The illustrated mouse 200 includes a scroll wheel 206, which may also be manufactured from PFA or other UV transmissive materials. Referring now to FIG. 34, the mouse 200 may include electronics that include a printed circuit board assembly 208 having a mouse control circuit 210 and associated components. The mouse circuit board 210 may include micro-switches 212 for the mouse buttons, and may also include a scroll wheel sensor (not shown) to sense rotation of the scroll wheel 206. It should be understood that the illustrated mouse electronics are merely exemplary and the mouse may include essentially any alternative electronics. The mouse circuit board 210 may also include the disinfection circuit and associated components, such as a pair of UV lamps 214 and one or more touch sensors (not shown). As shown, the UV lamps 214 may include two L-shaped UV lamps 214 that extend generally along the periphery of the printed circuit board assembly 208. The disinfection circuit and lamps 214 enable the supply of low dose UV-C and the disinfection control unit to be built into the mouse 200. The UV lamps 214 may be situated over the top surface of the circuit board, which allows the circuit board to function as a UV reflector to reflect UV energy upwardly into the UV transmissive top housing 202. Although not show, a UV reflector may be positioned beneath each UV lamp 214 to reflect UV light toward the desired regions of the top housing 202.

Figure 36:
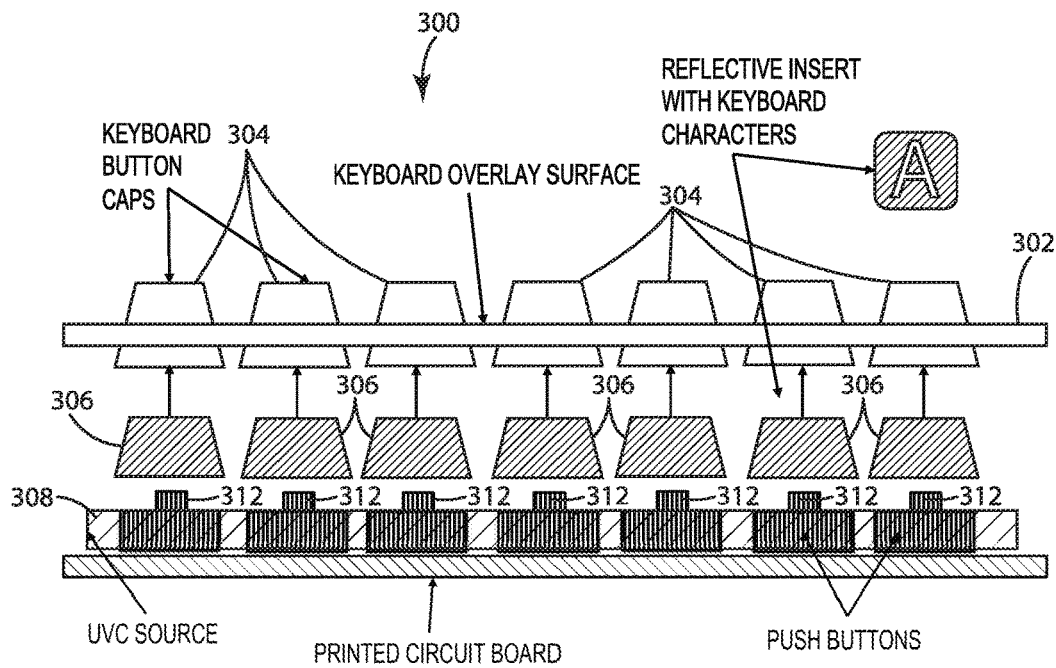
FIG. 36 shows a keyboard wherein the UV-C source is located along the rows of keys and the keys and keyboard surface is molded in PFA to enable UV-C transmission. The reflectors inserted into each key cap has the printed characters and also acts as a reflector. The design allows both treatment of surfaces above and below the keyboard surface.

FIG. 36 shows an embodiment of a keyboard 300 manufactured to enable low dose UV-C disinfection. The key board 300 generally includes a keyboard overlay structure 302 with key caps 304, reflective key inserts 306, a plurality of UV sources 308 and a printed circuit board assembly 310 with buttons 312. The key caps 304 and the remainder of the keyboard overlay structure 302 may be manufactured from PFA or other UV transmissive materials. The printed circuit board assembly 310 has a plurality of UV-C sources 308 that provides enough energy to be light piped through these key caps 302. For example, the UV sources 308 may be a plurality of elongated UV lamps that extend across the keyboard 300 between adjacent rows of keys. In this embodiment, the key cap insert 306 has the printed characters and acts as a reflector for the light pipe for better efficacy to the surface disinfection. For example, the external upper surfaces of the key inserts 306 are coated with a UV reflective material or the key inserts 306 may be a plastic impregnated with a UV reflective additive.

Figure 37:
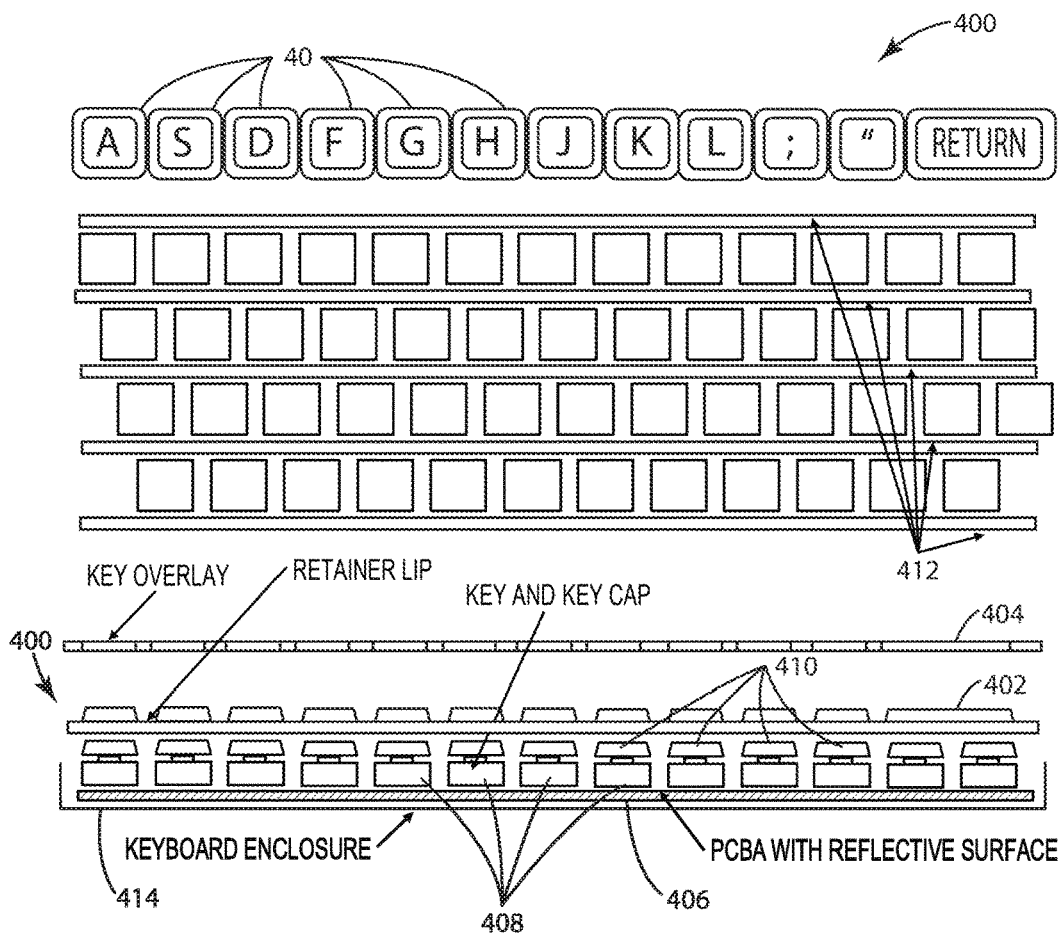
FIG. 37 shows the layers of a disinfection enabled keyboard with standard keys and keycaps. This system is then enabled by using an overlay and PFA bezel to receive the UV-C source for disinfection. The disinfecting source extends along the row of keys. A lower intensity source can be used over a larger surface when implemented this way. The diameter of the UV-C lamp can be much thinner or the LEDs can be lower intensity.

FIG. 37 shows an alternative keyboard incorporating an alternative embodiment of the present invention. In this embodiment, the keyboard 400 generally includes a plurality of keys 402, a key overlay 404, a printed circuit board assembly 406 with a plurality of push buttons 408 and key caps 410, a plurality of UV sources 412 and a keyboard enclosure 414. In this embodiment, the keys 402 and key overlay 404 are manufactured from a UV transmissive material, such as PFA. The UV sources 412 may include a plurality of elongated UV lamps arranged between adjacent rows of keys. The UV sources 412 may be essentially any alternative UV energy sources, such as UV LEDs. The printed circuit board assembly 406 may include a reflective upper surface configured to reflect UV light toward the keys 402 and key overlay 404. Similarly, the key caps 410 may be UV reflective, for example, by application of a UV transmissive coating or impregnating the key caps 410 with UV reflective additives.

Figure 38:
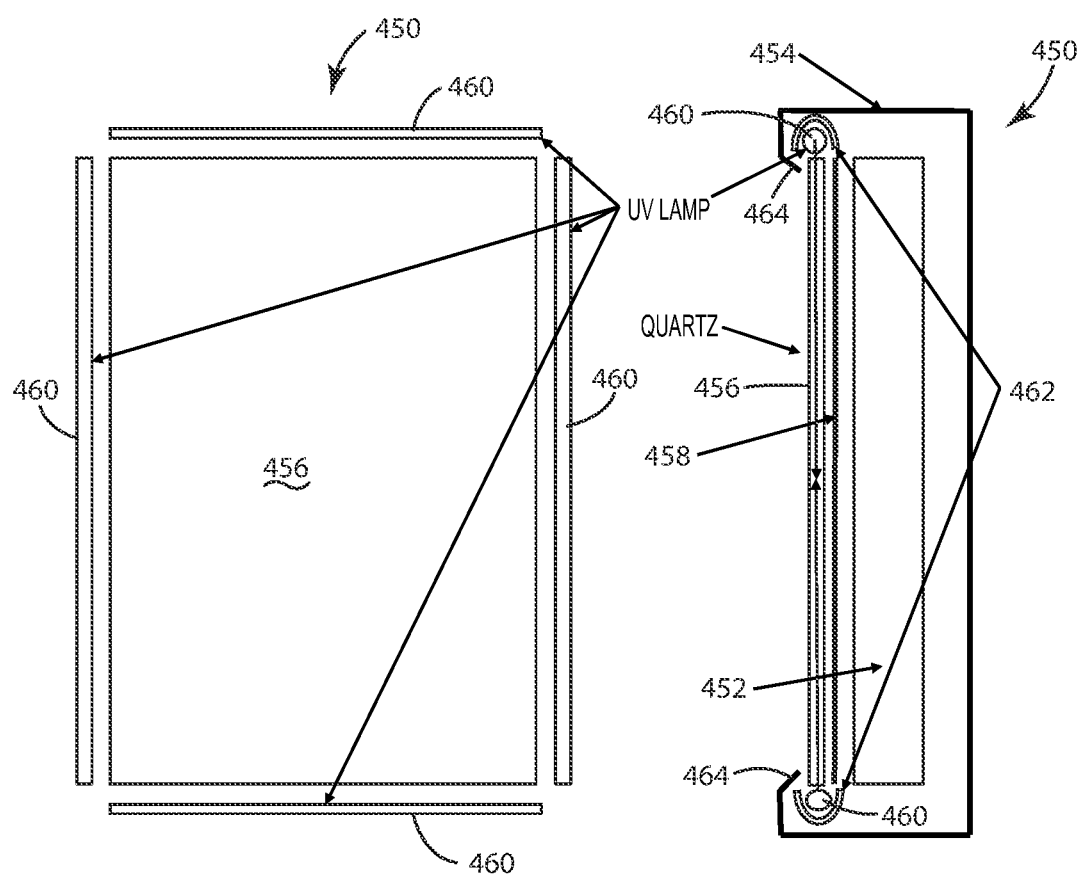
FIG. 38 shows an example of an edge lit kiosk with a disinfection control system. It should be noted that the edge of the quartz can be bent to accept light better for better piping and disinfection. The back side of the quartz can be coated for reflection but it is easier to coat a film that can be placed between the layers for reflecting the UV light out to the surface and have better optical properties.

The present invention is also well-suited for use in connection with kiosks and other similar products with touch screens. For example, FIG. 38 shows an exemplary kiosk with an integrated UV disinfection system. The kiosk 450 generally includes a touch screen 452 enclosed within a kiosk enclosure 454. The kiosk enclosure 454 may be include an edge structure that functions as a louver 464 for directing UV light. The UV disinfection system includes a UV transmissive overlay 456, a reflective sheet 458, UV sources 460 and reflectors 462. The UV transmissive overlay 456 may be manufactured from PFA or other UV transmissive materials. The UV reflective sheet 458 may include a reflective coating on its outward facing surface to reflect UV light emerging from the interior of the UV transmissive overlay 456. In this embodiment, the UV sources 460 include elongated UV lamps arranged along the edges of the UV transmissive overlay 456 to transmit UV energy through the edges of the overlay 456. The reflectors 462 are positioned outwardly of the UV lamps and are configured to reflect light from the UV sources into the edges of the UV transmissive overlay 456.

J. UV Disinfection System Calibration

The present invention may be implemented as a UV treatment device that can be mounted on or adjacent to the surface to be treated. This may, for example, be a keyboard, touchscreen, handle or other surface that may be touched and may benefit from UV treatment. The position of the UV treatment device relative to the surface to be treated, as well as the size, shape and configuration of the surface to be treated, will contribute to the intensity of light that reaches surface to be treated. To ensure that the entire surface is properly disinfected, it is important to set the UV source intensity so that even the portions of the surface that receive the least amount of UV-C energy are properly disinfected.

To achieve this objection, the system may be configured to implement a calibration method in which actual UV intensity measurements are used to set initial intensity of the UV-C source. In one embodiment, the calibration method includes the steps of: a) installing the UV treatment device adjacent to the surface to be treated; b) energizing the UV-C source at a predetermined power level; c) measuring the UV-C intensity at a plurality of locations using a UV intensity meter, d) determining the lowest UV-C intensity measurement, e) determining the UV-C power level required to provide the desired UV-C intensity at the location of the lowest UV-C intensity measurement and f) setting the initial UV-C power level for the UV-C source to correspond with the determined UV-C power level. Additionally or alternatively, the calibration algorithm may adjust exposure time. For example, if the lowest measured intensity is lower than the desired intensity, the UV parameters may be adjusted to extend the initial duration of the UV treatment cycle in addition to or as an alternative to adjusting the initial UV-C power level. After calibration is performed, the UV treatment parameters are accurate for that particular arrangement in that a UV treatment cycle can confidently be expected to disinfect the entire surface to be treated. As can be seen, the calibration measurements provide actual UV intensity measurements immediately adjacent the surface to be treated, and these measurements are used to adjust the UV intensity and/or exposure time, for example, in accordance with the algorithm provided above. In some embodiments, the calibration values (e.g. initial UV-C power level and initial cycle duration) are stored in non-volatile registers. The values may, however, be adjusted over time to compensate for UV-C output degradation over lamp life. Further, the measured calibration number(s) may be stored in a non-volatile register and be set at installation by communicating to a custom calibration tool. For example, the UV disinfection device may communicate wirelessly or by wired connection with a calibration application running on a mobile device, such as a smartphone, tablet, laptop or custom electronic calibration device. Once set, the system has the details for that surface, distance and measured dose and can reference that number for treating and reporting about that surface and employee exposure accordingly.

The calibration method may vary from application to application. In some applications, the calibration process and method for OEM installations can be used as a pass fail criteria for testing. In this context, the process for calibration of dose and exposure may include the following steps: a) set device at installed distance and attitude; b) sequentially set UV-C calibration sensor at each of the four outside corners of the disinfection area; c) measure all corners for intensity and exposure; d) log pass and fail for exposure testing requirements; e) store minimum required values for in UV-C disinfection device for reference; and f) log configuration for serial number.

K. Dynamic UV Disinfection Control

In another aspect, the present invention provide a system and method for tracking and understanding actions and interactions relating to disinfection. For example, an entire network of UV disinfection devices and UV disinfection sensor can be used to collect data and other information relevant to infections and disinfection. The data and other information collected using the system can be combined with data and other information collected outside the network. The data and information can be combined and used in many ways to understand and take action to address infections. For example, the information can be used to dynamically control the UV disinfection systems associated with the network. This can be controlling the UV parameters on a dynamic basis to allow each UV disinfection device to adapt to its environment and associated interactions or to facilitate network wide control functions, such as causing network-wide or sub-group operation of UV disinfection devices in response to collected data and other information. The UV disinfection network may be used to collect essentially any data and information that might be useful to understanding and addressing infections.

In one embodiment, the present invention provides a UV disinfection control system that is configured to dynamically adjust UV treatment duration and/or UV source intensity dynamically in response to a variety of measured data. For example, the control system may be configured to carry out a UV disinfection cycle each time there is a touch event, and to terminate any cycle that is interrupted by a touch. The touch event may be sensed by a capacitive touch sensor or by other types of touch sensors. In the illustrated embodiment, the control system may be determine or be provided with initial UV intensity and initial UV cycle duration values. The control system may store the initial UV intensity and the initial UV cycle duration in memory. These initial values may, for example, be determined using the calibration methodology described elsewhere in this disclosure. For purposes of this disclosure, the initial UV cycle time will be six minutes and the initial UV intensity will be ~559 mm (22")×241 mm (9.5") @ ~1 uW/cm^2. To prevent the system from repeated starting and stopping the UV-C as a result of frequent touch events, the control system may be configured to wait a specified amount of time (e.g. stored as a "touch delay") after the most recent touch before energizing the UV-C source. The time may be offset by a stored distance measurement used by the OEM of installation personnel upon configuration. If the UV disinfection network recognizes additional hardened pathogens, the control system can then adjust dose based on distances and known power levels. This time may vary from application to application depending on the nature of touch interactions for the specific device being treated. In the context of a keyboard, for example, the control system may be configured to wait a period of one minute after the last touch occurs before energizing the UV-C source. In the context of devices that have shorter average touch durations, such as the control panel for an IV pump, the touch delay may be significantly shorter. As another option, the control system may store a "touch delay" value that is roughly equivalent to or a predetermined amount of time longer than the average duration of a touch interaction. For example, if the average length of a touch interaction on the type of device is two minutes, the control system may set a touch delay of three minutes to allow sufficient time for most touch interactions to complete. For this example, the touch delay is about 150% of the average length of a touch interaction, but the touch delay may be a different percentage of the average or selected independently from the average. In this context, when a touch occurs, the control system may wait the length of the touch delay before energizing the UV-C source. The control system may also keep track of cycle interruptions. A cycle interruption occurs when a touch event takes place while the UV source is energized and in the process of implementing a UV disinfection cycle. When a touch interrupts a cycle, the control system turns off the UV source and follows a delay protocol, such as one of the two options described above, before attempting to restart the UV source. If the disinfection cycle is interrupted too many times in a row, the control system may increase the UV source intensity to attempt to complete a UV disinfection cycle in the available time between touches. For example, the control system may look at the average touch interval (e.g. average amount of time that passes between touches) or at actual recent touch intervals (e.g. the amount of time between the most recent touches or number of touches) to determine the increased intensity. For example, if the average touch interval for this device during this time frame (e.g. this time in the day) is four minutes, the control system may scale up the UV source intensity so that it generates sufficient UV-C energy to fully disinfect the touch surface in four minutes rather continuing to attempt to disinfect the surface for six minutes at the initial UV intensity. Once the control system implements an increased UV intensity, it may apply the increased intensity for a predetermined number of UV disinfection cycles before switching back to the initial UV intensity and initial UV cycle time, or it may continue to monitor touch interactions and return to the initial UV intensity and initial UV cycle when the amount of time that passes between sequentially touch interactions is sufficient to accommodate a full UV disinfection cycle at initial UV intensity (e.g. a six minute cycle).

The control system may also be configured to implement supplemental cycles that occur whether or not a touch has taken place. This may include time based cycles (e.g. one disinfection cycle every four hours after the end of the most recent previous disinfection cycle) and/or event based cycles (e.g. an infection has been identified in sufficient proximity to the device). Although these supplemental cycles are likely to take place at the initial UV intensity and for the initial cycle duration, it is possible in some applications for supplemental cycles to occur at modifies parameters, such as a higher intensity, lower intensity, shorter duration or longer duration.

L. System and Method for Tracking Lamp Life

The present invention may include a system and method for accurately tracking lamp life despite variations in UV intensity. In one embodiment, the UV disinfection system may include memory capable of storing actual lamp run time data. This memory may be located in the control system and may be reset each time a new UV source is installed and/or it may be located on the UV source so that it remains with the UV source even if the UV source is removed and replaced or moved from one UV disinfection device to another. In the illustrated embodiment, the UV source may include an RFID chip that can is capable of exchanging communications with the control system. For example, the control system 30 of FIG. 5 includes an RFID reader 26 having a transceiver that is capable of communicating with the RFID tag 38 on board the UV source 34. The RFID tag 38 on the UV source 34 may have a unique identifier and may have resident memory for accumulating lamp "on" time. In operation, the control system 30, for example, controller 36, may have an onboard clock that tracks the time the UV source 34 is energized and accumulates that time in the memory location on the RFID tag 38. For example, the control system may operate by retrieving the accumulated run time from the RFID tag, initiating operation of the UV source, storing the start time of the UV source, allowing the UV source to operate for a period of time (e.g. a cycle), turning off the UV source, determining the amount of time the UV source was on during that cycle, adding the on time for that cycle to the accumulated run time retrieved from the RFID tag and then rewriting the new accumulated run time on the RFID tag. Although this method works well in many applications, the control system may be configured to implement a modified procedure to account for variations in UV source intensity over time. More specifically, the control system may be configured to adjust on time upwardly to compensate for the application of additional power to the UV source during UV disinfection cycles that involve an increase in UV intensity. In one embodiment, the control system may maintain a counter that reflects the amount of time that the UV source is operated at an elevated intensity. After completion of each cycle at an elevated intensity, the control system may increment the accumulated run time on the RFID chip to adjust for the elevated intensity. In one embodiment, the control system may multiply the actual run time for the elevated cycle by a correlation factor or multiplier that reflects the impact of the elevated intensity on UV source life. The correlation factor may be predetermined by lamp life tests conducted on the UV source at different intensity levels. Alternatively, the correlation multiplier may be an approximation based on typical UV lamp characteristics. For example, the control system may be provided with a table of multipliers that provide a conservative estimate of the impact of different elevated intensity on lamp life. As another alternative, the lamp life adjustment may be a linear approximation that varies in proportion with UV source intensity. To illustrate, operating the UV source for a cycle at a 50% increase in lamp intensity could result in a 50% increase in the lamp life accumulation for that cycle. Although this example reflects a one-to-one correlation between intensity and lamp life consumption, the correlation factor may vary from application to application based on actual lamp characteristics.

M. Additional Exemplary UV Disinfection Devices

Figure 40:
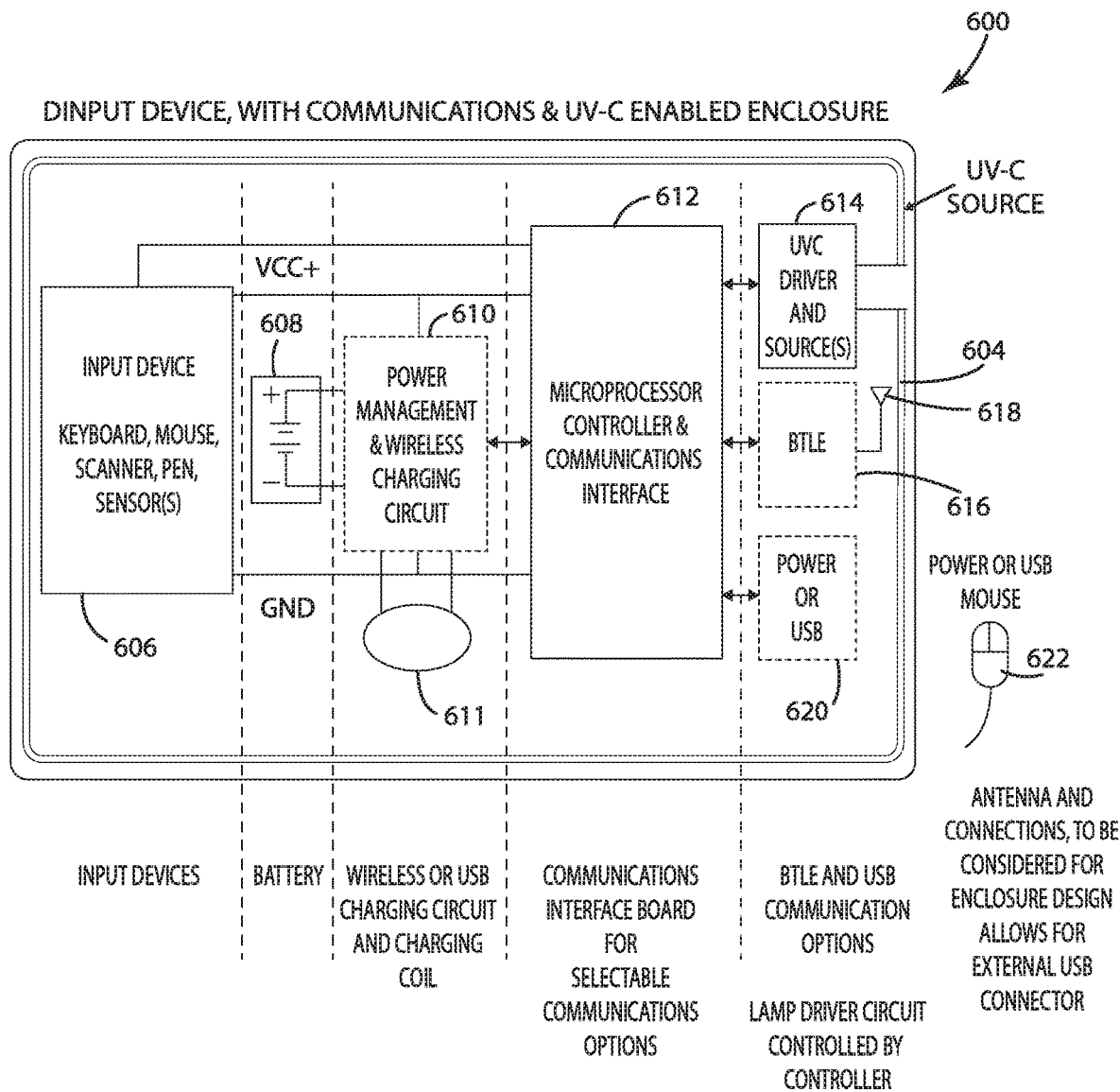
FIG. 40 is a schematic representation of an input device with communications and an internal UV disinfection system.

As noted above, the present invention may provide a UV disinfection system that is integrated into another device to allow UV disinfection of the outer surfaces of the device using an internal UV source. In this aspect, the present invention is well-suited for incorporation into device that are frequently touched or otherwise subject to frequent bioloading, including input devices, such as mouse, keyboards, touch panels, etc. FIG. 40 shows an input device having an internal UV disinfection system in accordance with an embodiment of the present invention. The input device 600 generally includes an enclosure 602, a UV-C source 604, a input device electronics 606, a battery 608, a power management and wireless charging circuit 610, a microprocessor controller and communications interface 612, a UV-C driver 614, a BTLE communication circuit 616, a BTLE antenna 618, a power or USB circuitry 620 and a power or USB cable 622. In this embodiment, the enclosure 602 forms the outer surface(s) of the device 600 and is subject to receive touches and other human interactions. The enclosure 602 of this embodiment includes at least a portion that is UV-C transmissive so that internally generated UV-C energy can be directed to that portion to allow UV disinfection. The enclosure 602 may be manufacture from one or more components. For example, in one embodiment, the portion (s) of the enclosure 602 that are likely to be touched during operation may be manufactured from one or more enclosure portions that are manufactured from UV-C transmissive material, while the portions that are unlikely to be touched may be manufactured from materials that are not UV-C transmissive. In some applications, the UV-C transmissive material may be disposed over a UV-C reflective substrate. The substrate may provide the UV-C transmissive material with structural support and its reflective properties may help to direct UV-C energy onto the outer touch surface(s) of the UV-C transmission enclosure portions. In this embodiment, the UV-C source 604 is illustrated as a single source extending around the perimeter of the enclosure 602. It should be understood that the UV-C source 604 may be essentially any type and any number of UV-C sources. For example, the UV-C source 604 may be one or more gas discharge bulbs and/or one or more UV-C LEDs. Further, the UV-C source 604 need not extend around the perimeter of the enclosure 602, but may be of any configuration that allows the desired level of UV disinfection by virtue of proximity and/or the transmission of light through the UV-C transmissive material. For example, in the context of a mouse, the UV-C source may be a pair of L-shaped UV-C light bulbs that are arranged in a rectangle about the perimeter of the mouse enclosure. The input device electronics 606 may be essentially any suitable electronics for the corresponding type of input device now known or later developed. For example, in the context of an optical mouse, the input device electronics 606 may include a PS/2 mouse controller, a plurality of mouse button switches, and an optical mouse sensor (not shown). In this embodiment, the input device 600 is a wireless electronic device. In this context, the device 60 includes a battery 608 (or any other suitable electrical energy storage device, such as a high capacity capacitor) for storing electrical energy. The power management and wireless charging circuit 610 is configured to wirelessly receive power from a remote wireless power supply and to control the supply of power to the various power consuming components within the device 600. The wireless charging circuit may include an inductive secondary coil 611 that receives power from an inductive wireless power supply, such as a Qi compliant wireless charger, or essentially any other type of wireless power supply capable of delivering adequate power to the input device 600. The device 600 need not, however, incorporate a wireless power supply and may alternatively be powered using a wired connection or a replaceable battery. The microprocessor controller and communications interface 612 may control operation of the UV disinfection system. For example, it may operate the UV-C source 604 to implement UV disinfection cycles. It may also communicate with one or more sensors capable of sensing when a touch event has occurred. The sensors (not shown) may include any sensor or plurality of sensors capable of determining when touch interactions have occurred. This may include motion sensors, capacitive sensors and/or inductive sensors. The microprocessor controller and communications interface 612 may also communicate with the UV disinfection network. For example, it may communicate with a disinfection network hub of the type described elsewhere in this disclosure. Among other things, this allows the UV disinfection system to report relevant data to the UV disinfection network and to receive operation and control commands from the UV disinfection network. In this embodiment, the device 600 also includes a UV-C driver 614 that is capable of energizing and operating the UV-C source(s) 604. The UV-C driver 614 of this embodiment is controlled by the microprocessor controller and communications interface 612 and may be essentially any driver circuit capable of properly supplying power to the UV-C source(s) 604. In this embodiment, the UV disinfection system is configured to communication with the UV disinfection network using conventional Blue Tooth Low Energy ("BTLE") communications. The BTLE circuit 616 of this embodiment includes a BTLE transceiver that is coupled to BTLE antenna 618. The present invention may be implemented with additional or alternative communication systems that operate using additional or alternative communications protocols. In the embodiment of FIG. 43, the device 600 includes power or USB circuitry 620 configured to receive power using a power cable or a USB cable 622. The power or USB circuitry 620 may be essentially any circuitry capable of supplying power to the device 600 or the microprocessor controller and communications interface 612 from a power cord or USB cord 622. The power or USB circuitry 620 may also allow communications between the microprocessor controller and communications interface 612, for example, via a conventional USB cable 622.

Figure 41:
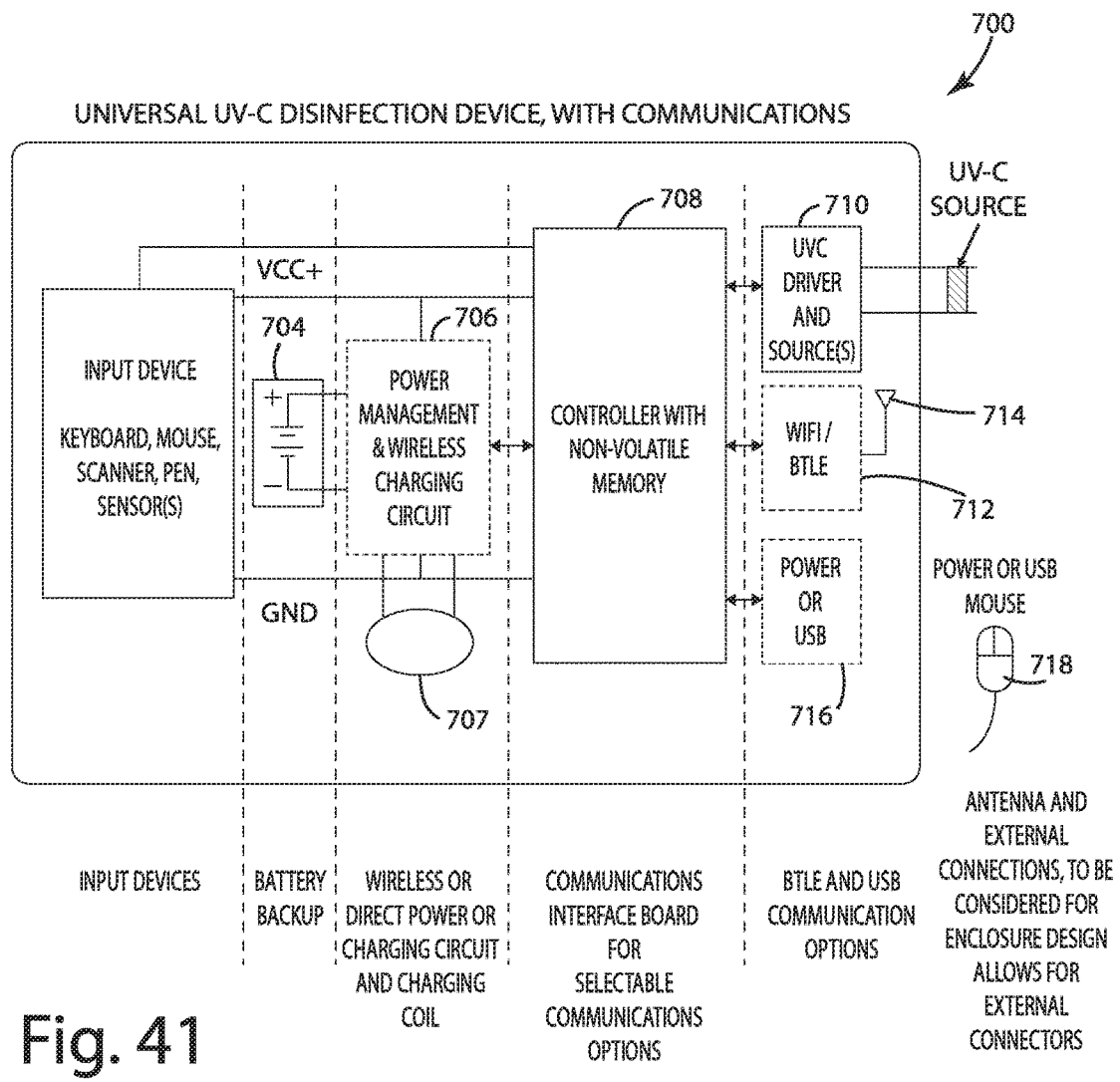
FIG. 41 is a schematic representation of a universal UV disinfection device with communications and an external UV source used for external disinfection procedures.

The present invention may also be implemented as a stand-alone UV disinfection device that is capable of energizing an external UV-C source intended to provide UV disinfection to separate touch surfaces. It is important to note that the input devices can include capacitive and thermal sensing to help in assisting the control of the UV-C source. FIG. 41 is a schematic representation of a stand-alone device 700 with one or more external UV-C source(s) 702. The UV disinfection device 700 generally includes a UV-C source 702, a battery 704, a power management and wireless charging circuit 706, a microprocessor controller and communications interface 708, a UV-C driver 710, a BTLE communication circuit 712, a BTLE antenna 714, a power or USB circuitry 716 and a power or USB cable 718. In this embodiment, the UV-C source 702 is illustrated as a single source, but it should be understood that the UV-C source 702 may be essentially any type and any number of UV-C sources. For example, the UV-C source 702 may be one or more UV-C gas discharge bulbs and/or one or more UV-C LEDs. In this embodiment, the UV disinfection device 700 includes a battery 704 (or any other suitable electrical energy storage device, such as a high capacity capacitor) for storing electrical energy. The power management and wireless charging circuit 706 is configured to wirelessly receive power from a remote wireless power supply (not shown) and to control the supply of power to the various power-consuming components within the device 700. As noted above in connection with device 600, the wireless charging circuit 706 of this embodiment may include an inductive secondary coil 707 that receives power from an inductive wireless power supply, such as a Qi compliant wireless charger, or essentially any other type of wireless power supply capable of delivering adequate power to the UV disinfection device 700. The UV disinfection device 700 need not, however, incorporate a wireless power supply and may alternatively be powered using a wired connection or a replaceable battery. The microprocessor controller and communications interface 708 may control operation of the UV disinfection system. For example, it may operate the UV-C source(s) 702 to implement UV disinfection cycles. It may also communicate with one or more sensors capable of sensing when a touch event has occurred with respect to the touch surface being treated. The sensors (not shown) may include any sensor or plurality of sensors capable of determining when touch interactions have occurred. This may include motion sensors, capacitive sensors and/or inductive sensors. The microprocessor controller and communications interface 706 may also communicate with the UV disinfection network. For example, it may communicate with a disinfection network hub. Among other things, this allows the UV disinfection system to report relevant data to the UV disinfection network and to receive operation and control commands from the UV disinfection network. In this embodiment, the UV disinfection device 700 also includes a UV-C driver 710 that is controlled by the microprocessor controller and communications interface 708 and is capable of energizing and operating the UV-C source(s) 702. The UV-C driver 710 of this embodiment is may be essentially any driver circuit capable of properly supplying power to the UV-C source(s) 702. In this embodiment, the UV disinfection device 700 is configured to communication with the UV disinfection network using conventional Blue Tooth Low Energy ("BTLE") communications. The BTLE circuit 712 of this embodiment includes a BTLE transceiver that is coupled to BTLE antenna 714. The present invention may be implemented with additional or alternative communication systems that operate using additional or alternative communications protocols. The UV disinfection device 700 of this embodiment includes power or USB circuitry 716 configured to receive power using a power cable or a USB cable 718. The power or USB circuitry 716 may also allow communications between the microprocessor controller and communications interface 708, for example, via a conventional USB cable 718.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The invention claimed is:

1. A method of operating a UV disinfection system to disinfect a touch surface, comprising the steps of:
   providing a UV disinfection system with a UV source driver configured to drive operation of a UV source at a plurality of different UV output intensities;
   operating the UV source for a first cycle at a first source intensity for a first duration;
   interrupting operation of the UV source during the first cycle in response to a touch sensed on the touch surface;
   tracking at least one of a frequency of interruptions, a number of interruptions and a number of touches; and
   in response to the at least one of the frequency of interruptions, the number of interruptions and the number of touches, operating the UV source for a second cycle at a second source intensity greater than the first source intensity.

2. The method of claim 1 wherein a first UV output intensity is an effective irradiance of no greater than 0.008 watts per meter squared.

3. The method of claim 2 wherein a second UV output intensity is an effective irradiance of at least 0.016 watts per meter squared.

4. The method of claim 1 wherein a first UV output intensity is an effective irradiance of no greater than 0.005 watts per meter squared.

5. The method of claim 4 wherein a second UV output intensity is an effective irradiance of at least 0.010 watts per meter squared.

6. A method of operating a UV disinfection system to disinfect a touch surface, comprising the steps of:
   providing a UV disinfection system with a UV source driver configured to drive operation of a UV source at a plurality of different UV output intensities;
   operating a UV source for a first cycle at a first source intensity for a first duration;
   interrupting operation of the UV source during the first cycle in response to a touch sensed on the touch surface;
   tracking at least one of a frequency of interruptions, a number of interruptions and a number of touches; and
   in response to the at least one of the frequency of interruptions, the number of interruptions and the number of touches, operating the UV source for a second cycle at a second source intensity for a second duration, wherein at least one of the second source intensity is greater than the first source intensity and the second duration is greater than the first duration.

7. The method of claim 6 wherein a first UV output intensity is an effective irradiance of no greater than 0.008 watts per meter squared.

8. The method of claim 7 wherein a second UV output intensity is an effective irradiance of at least 0.016 watts per meter squared.

9. The method of claim 6 wherein a first UV output intensity is an effective irradiance of no greater than 0.005 watts per meter squared.

10. The method of claim 9 wherein a second UV output intensity is an effective irradiance of at least 0.010 watts per meter squared.

* * * * *